(12) United States Patent
Jung et al.

(10) Patent No.: US 7,927,787 B2
(45) Date of Patent: *Apr. 19, 2011

(54) METHODS AND SYSTEMS FOR ANALYSIS OF NUTRACEUTICAL ASSOCIATED COMPONENTS

(75) Inventors: Edward K. Y. Jung, Bellevue, WA (US);
Eric C. Leuthardt, St. Louis, MO (US);
Royce A. Levien, Lexington, MA (US);
Robert W. Lord, Seattle, WA (US);
Mark A. Malamud, Seattle, WA (US);
John D. Rinaldo, Jr., Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 617 days.

This patent is subject to a terminal disclaimer.

(21) Appl. No.: 11/637,638

(22) Filed: Dec. 11, 2006

(65) Prior Publication Data
US 2008/0003307 A1    Jan. 3, 2008

Related U.S. Application Data

(63) Continuation-in-part of application No. 11/478,296, filed on Jun. 28, 2006.

(51) Int. Cl.
*C12Q 1/00* (2006.01)
(52) U.S. Cl. ....... 435/4; 436/501; 435/287.1; 435/288.5
(58) Field of Classification Search .......... None
See application file for complete search history.

(56) References Cited

U.S. PATENT DOCUMENTS

| | | |
|---|---|---|
| 4,009,078 A | 2/1977 | Wilkins et al. |
| 4,257,041 A | 3/1981 | Masucci |
| 4,436,378 A | 3/1984 | Kirkman |
| 4,567,185 A | 1/1986 | Sackner |
| H201 H | 1/1987 | Yager |
| 4,729,636 A | 3/1988 | Te Velde et al. |
| 4,807,967 A | 2/1989 | Veenvliet et al. |
| 4,847,764 A | 7/1989 | Halvorson |
| 4,857,716 A | 8/1989 | Gombrich et al. |
| 5,006,343 A | 4/1991 | Benson et al. |
| 5,054,493 A | 10/1991 | Cohn et al. |
| 5,093,268 A | 3/1992 | Leventis et al. |
| 5,284,656 A | 2/1994 | Platz et al. |
| 5,300,302 A | 4/1994 | Tachon et al. |
| 5,307,263 A | 4/1994 | Brown |
| 5,354,934 A | 10/1994 | Pitt et al. |
| 5,412,560 A | 5/1995 | Dennison |
| 5,490,962 A | 2/1996 | Cima et al. |
| 5,654,011 A | 8/1997 | Jackson et al. |
| 5,672,154 A | 9/1997 | Sillén et al. |
| 5,686,429 A | 11/1997 | Lin et al. |
| 5,692,502 A | 12/1997 | Alpert |
| 5,704,350 A | 1/1998 | Williams, III |
| 5,719,123 A | 2/1998 | Morley et al. |
| 5,737,539 A | 4/1998 | Edelson et al. |
| 5,747,349 A | 5/1998 | van den Engh et al. |
| 5,758,095 A | 5/1998 | Albaum et al. |
| 5,758,096 A | 5/1998 | Barsky et al. |
| 5,765,606 A | 6/1998 | Takemasa et al. |
| 5,780,014 A | 7/1998 | Eljamal et al. |
| 5,807,579 A | 9/1998 | Vilkov et al. |
| 5,820,876 A | 10/1998 | Hoffmann |
| 5,824,494 A | 10/1998 | Feldberg |
| 5,837,196 A | 11/1998 | Pinkel et al. |
| 5,839,438 A | 11/1998 | Graettinger et al. |
| 5,873,369 A | 2/1999 | Laniado et al. |
| 5,882,931 A | 3/1999 | Petersen |
| 5,907,291 A | 5/1999 | Chen et al. |
| 5,940,801 A | 8/1999 | Brown |
| 5,945,115 A | 8/1999 | Dunn et al. |
| 5,954,640 A | 9/1999 | Szabo |
| 5,955,269 A | 9/1999 | Ghai et al. |
| 5,958,458 A | 9/1999 | Norling et al. |
| 5,972,710 A | 10/1999 | Weigl et al. |
| 5,993,783 A | 11/1999 | Eljamal et al. |
| 5,995,938 A | 11/1999 | Whaley |
| 6,021,202 A | 2/2000 | Anderson et al. |
| 6,023,916 A | 2/2000 | Bouthiette |
| 6,024,699 A | 2/2000 | Surwit et al. |
| 6,035,230 A | 3/2000 | Kang et al. |
| 6,087,090 A | 7/2000 | Mascarenhas |
| 6,090,545 A | 7/2000 | Wohlstadter et al. |
| 6,117,073 A | 9/2000 | Jones et al. |
| 6,128,534 A | 10/2000 | Park et al. |

(Continued)

FOREIGN PATENT DOCUMENTS

JP    61002060 A    1/1986

(Continued)

OTHER PUBLICATIONS

Evans, R. Scott, Ph.D. et al., "A Computer-Assisted Management Program for Antibiotics and Other Antiinfective Agents"; The New England Journal of Medicine; bearing a date of Jan. 22, 1998; pp. 232-238; vol. 338, No. 4; The Departments of Clinical Epidemiology (R.S.E., S.L.P., D.C.C., J.F.L., J.P.B.), Critical Care (T.P.C., L.K.W., J.F.O.), and Medical Informatics (R.S.E.), LDS Hospital, Salt Lake City, UT. U.S. Appl. No. 12/011,008, Jung et al.
U.S. Appl. No. 11/977,174, Jung et al.
PCT International Search Report; International App. No. PCT/US 06/47436; Jan. 30, 2008; pp. 1-2.
U.S. Appl. No. 11/637,606, Jung et al.
U.S. Appl. No. 11/474,109, Jung et al.
U.S. Appl. No. 11/314,945, Jung et al.
U.S. Appl. No. 11/291,482, Jung et al.
U.S. Appl. No. 11/824,604, Jung et al.
U.S. Appl. No. 11/824,529, Jung et al.
Aihara, K; Kajimoto, O; Hirata, H; Takahashi, R; Nakamura, Y; "Effect of powdered fermented milk with *Lactobacillus helveticus* on subjects with high-normal blood pressure or mild hypertension"; J. Am. Coll. Nutr.; Bearing a date of Aug. 2005; pp. 257-265 (pp. 1-2); vol. 24, No. 4; PubMed; at: http://www.ncbi.nlm.nih.gov/sites/entrez?db=pubmed&list_uids=16093403&cmd=Retrieve&indexed=google; printed on Jun. 25, 2007.

(Continued)

*Primary Examiner* — N. Yang

(57) ABSTRACT

The present disclosure relates to methods and systems that may be used for analysis of nutraceutical associated components.

60 Claims, 24 Drawing Sheets

U.S. PATENT DOCUMENTS

| | | | |
|---|---|---|---|
| 6,139,494 A | 10/2000 | Cairnes |
| 6,161,095 A | 12/2000 | Brown |
| 6,169,068 B1 | 1/2001 | Levin et al. |
| 6,188,988 B1 | 2/2001 | Barry et al. |
| 6,194,900 B1 | 2/2001 | Freeman et al. |
| 6,221,677 B1 | 4/2001 | Wu et al. |
| 6,280,771 B1 | 8/2001 | Monkhouse et al. |
| 6,287,595 B1 | 9/2001 | Loewy et al. |
| 6,295,506 B1 | 9/2001 | Heinonen et al. |
| 6,317,719 B1 | 11/2001 | Schrier et al. |
| 6,335,021 B1 | 1/2002 | Cavazza |
| 6,379,929 B1 | 4/2002 | Burns et al. |
| 6,383,136 B1 | 5/2002 | Jordan |
| 6,397,190 B1 | 5/2002 | Goetz |
| 6,421,650 B1 | 7/2002 | Goetz et al. |
| 6,451,286 B1 | 9/2002 | Modi |
| 6,454,945 B1 | 9/2002 | Weigl et al. |
| 6,468,805 B1 | 10/2002 | Smith |
| 6,482,306 B1 | 11/2002 | Yager et al. |
| 6,510,430 B1 | 1/2003 | Oberwager et al. |
| 6,529,446 B1 | 3/2003 | de la Huerga |
| 6,541,213 B1 | 4/2003 | Weigl et al. |
| 6,541,478 B1 | 4/2003 | O'Malley et al. |
| 6,565,841 B1 | 5/2003 | Niven et al. |
| 6,565,874 B1 | 5/2003 | Dunn et al. |
| 6,576,267 B2 | 6/2003 | Gelber et al. |
| 6,582,987 B2 | 6/2003 | Jun et al. |
| 6,589,169 B1 | 7/2003 | Surwit et al. |
| 6,605,454 B2 | 8/2003 | Barenburg et al. |
| 6,616,606 B1 | 9/2003 | Petersen et al. |
| 6,630,155 B1 | 10/2003 | Chandrashekar et al. |
| 6,656,507 B2 | 12/2003 | Petereit et al. |
| 6,671,818 B1 | 12/2003 | Mikurak |
| 6,695,147 B1 | 2/2004 | Yager et al. |
| 6,699,193 B2 | 3/2004 | Crutchfield et al. |
| 6,709,676 B2 | 3/2004 | Cho |
| 6,709,869 B2 | 3/2004 | Mian et al. |
| 6,759,062 B2 | 7/2004 | Gelber et al. |
| 6,764,831 B2 | 7/2004 | Cameron, Sr. et al. |
| 6,773,714 B2 | 8/2004 | Dunn et al. |
| 6,773,721 B1 | 8/2004 | Wong et al. |
| 6,787,164 B2 | 9/2004 | Gelber et al. |
| 6,790,198 B1 | 9/2004 | White et al. |
| 6,793,942 B2 | 9/2004 | Gelber et al. |
| 6,794,196 B2 | 9/2004 | Fonash et al. |
| 6,812,458 B2 | 11/2004 | Gregori et al. |
| 6,818,435 B2 | 11/2004 | Carvalho et al. |
| 6,838,076 B2 | 1/2005 | Patton et al. |
| 6,841,544 B2 | 1/2005 | Gelber et al. |
| 6,849,396 B2 | 2/2005 | Schneider |
| 6,852,206 B2 | 2/2005 | Pawliszyn et al. |
| 6,878,755 B2 | 4/2005 | Singh et al. |
| 6,881,425 B2 | 4/2005 | Pushpangadan et al. |
| 6,888,095 B2 | 5/2005 | Khan |
| 6,921,527 B2 | 7/2005 | Platz et al. |
| 6,946,144 B1 | 9/2005 | Jordan |
| 6,951,545 B2 | 10/2005 | Smith et al. |
| 6,955,873 B1 | 10/2005 | Blum |
| 6,958,216 B2 | 10/2005 | Kelley et al. |
| 6,962,720 B2 | 11/2005 | Haridas et al. |
| 6,979,463 B2 | 12/2005 | Kou |
| 6,979,471 B1 | 12/2005 | Khanuja et al. |
| 6,979,679 B2 | 12/2005 | Marcum |
| 6,980,958 B1 | 12/2005 | Surwit et al. |
| 7,016,752 B1 | 3/2006 | Ruben et al. |
| 7,022,288 B1 | 4/2006 | Boss |
| 7,029,441 B2 | 4/2006 | Dodds |
| 7,030,989 B2 | 4/2006 | Yager et al. |
| 7,041,317 B2 | 5/2006 | Sekiya et al. |
| 7,041,670 B2 | 5/2006 | Boojamra et al. |
| 7,041,840 B2 | 5/2006 | Gandhi |
| 7,045,145 B2 | 5/2006 | Chien |
| 7,045,159 B1 | 5/2006 | Ilic et al. |
| 7,046,357 B2 | 5/2006 | Weinberger et al. |
| 7,048,945 B2 | 5/2006 | Percel et al. |
| 7,049,312 B1 | 5/2006 | Rafferty et al. |
| 7,049,433 B2 | 5/2006 | Fan et al. |
| 7,053,107 B2 | 5/2006 | Borchardt et al. |
| 7,056,951 B2 | 6/2006 | Spireas |
| 7,074,311 B1 | 7/2006 | Cunningham |
| 7,074,583 B2 | 7/2006 | Yoshizato et al. |
| 7,112,444 B2 | 9/2006 | Beebe et al. |
| 7,135,616 B2 | 11/2006 | Heard et al. |
| 7,136,820 B1 * | 11/2006 | Petrus ............... 705/3 |
| 7,151,982 B2 | 12/2006 | Liff et al. |
| 7,169,432 B2 | 1/2007 | Tanaka et al. |
| 7,172,897 B2 | 2/2007 | Blackburn et al. |
| 7,193,128 B2 | 3/2007 | Copenhaver et al. |
| 7,197,492 B2 | 3/2007 | Sullivan |
| 7,206,605 B2 | 4/2007 | Hattori |
| 7,215,887 B2 | 5/2007 | Ternullo et al. |
| 7,216,343 B2 | 5/2007 | Das et al. |
| 7,218,900 B2 | 5/2007 | Suzuki |
| 7,227,956 B1 | 6/2007 | Onishi |
| 7,236,595 B1 | 6/2007 | Bean et al. |
| 7,245,894 B2 | 7/2007 | Sekiguchi et al. |
| RE39,785 E | 8/2007 | Fuse |
| 7,254,160 B2 | 8/2007 | Kawamoto et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B2 | 8/2007 | Matsumoto et al. |
| 7,280,975 B1 | 10/2007 | Donner |
| 7,351,739 B2 | 4/2008 | Ho et al. |
| 7,376,585 B2 | 5/2008 | Haller |
| 7,379,167 B2 | 5/2008 | Mawhirt et al. |
| 7,502,666 B2 | 3/2009 | Siegel et al. |
| 7,635,594 B2 | 12/2009 | Holmes et al. |
| 2001/0003177 A1 | 6/2001 | Schena et al. |
| 2001/0022758 A1 | 9/2001 | Howard |
| 2001/0037220 A1 | 11/2001 | Merry et al. |
| 2002/0004749 A1 | 1/2002 | Froseth et al. |
| 2002/0016719 A1 | 2/2002 | Nemeth et al. |
| 2002/0019784 A1 | 2/2002 | Ritz |
| 2002/0027164 A1 | 3/2002 | Mault et al. |
| 2002/0032580 A1 | 3/2002 | Hopkins |
| 2002/0032582 A1 | 3/2002 | Feeney, Jr. et al. |
| 2002/0032620 A1 | 3/2002 | Benz et al. |
| 2002/0046948 A1 * | 4/2002 | Chow et al. ............... 204/450 |
| 2002/0052763 A1 | 5/2002 | Jung Richardson |
| 2002/0055856 A1 | 5/2002 | Adams |
| 2002/0059030 A1 | 5/2002 | Otworth et al. |
| 2002/0065682 A1 | 5/2002 | Goldenberg |
| 2002/0070226 A1 | 6/2002 | Liff et al. |
| 2002/0077850 A1 | 6/2002 | McMenimen et al. |
| 2002/0091991 A1 | 7/2002 | Castro |
| 2002/0095238 A1 | 7/2002 | Ahlin et al. |
| 2002/0100762 A1 | 8/2002 | Liff et al. |
| 2002/0106429 A1 | 8/2002 | Mudar et al. |
| 2002/0143434 A1 | 10/2002 | Greeven et al. |
| 2002/0147317 A1 | 10/2002 | Bentsen et al. |
| 2002/0156651 A1 | 10/2002 | Florio et al. |
| 2002/0156683 A1 | 10/2002 | Stoutenburg et al. |
| 2002/0173875 A1 | 11/2002 | Wallace et al. |
| 2002/0177763 A1 | 11/2002 | Burns et al. |
| 2002/0194226 A1 | 12/2002 | Sheth et al. |
| 2002/0194502 A1 | 12/2002 | Sheth et al. |
| 2003/0005445 A1 | 1/2003 | Schein et al. |
| 2003/0019165 A1 | 1/2003 | Gallant et al. |
| 2003/0028399 A1 | 2/2003 | Davis et al. |
| 2003/0032868 A1 | 2/2003 | Graskov et al. |
| 2003/0036683 A1 * | 2/2003 | Kehr et al. ............... 600/300 |
| 2003/0055531 A1 | 3/2003 | Liff et al. |
| 2003/0061123 A1 | 3/2003 | McMenimen et al. |
| 2003/0065537 A1 | 4/2003 | Evans |
| 2003/0069757 A1 | 4/2003 | Greenberg |
| 2003/0073931 A1 * | 4/2003 | Boecker et al. ............... 600/573 |
| 2003/0074218 A1 | 4/2003 | Liff et al. |
| 2003/0083685 A1 | 5/2003 | Freeman et al. |
| 2003/0088333 A1 | 5/2003 | Liff et al. |
| 2003/0092039 A1 * | 5/2003 | Olson-Munoz et al. ......... 435/6 |
| 2003/0105552 A1 | 6/2003 | Lunak et al. |
| 2003/0121929 A1 | 7/2003 | Liff et al. |
| 2003/0125837 A1 | 7/2003 | Walace et al. |
| 2003/0135388 A1 | 7/2003 | Martucci et al. |
| 2003/0139655 A1 | 7/2003 | Dodds |

| | | |
|---|---|---|
| 2003/0156724 A1 | 8/2003 | Mariano et al. |
| 2003/0158756 A1 | 8/2003 | Abramson |
| 2003/0171950 A1 | 9/2003 | Kilgannon et al. |
| 2003/0189058 A1 | 10/2003 | Liff et al. |
| 2003/0191670 A1 | 10/2003 | Hatcher et al. |
| 2003/0193185 A1 | 10/2003 | Valley et al. |
| 2003/0204412 A1 | 10/2003 | Brier |
| 2003/0207270 A1 | 11/2003 | Kung et al. |
| 2003/0216831 A1 | 11/2003 | Hart et al. |
| 2003/0219812 A1 | 11/2003 | Quay et al. |
| 2003/0220848 A1 | 11/2003 | Behrendt |
| 2003/0229455 A1 | 12/2003 | Bevilacqua et al. |
| 2003/0233250 A1 | 12/2003 | Joffe et al. |
| 2004/0032330 A1 | 2/2004 | Hoffman |
| 2004/0033553 A1 | 2/2004 | Littarru et al. |
| 2004/0053290 A1 | 3/2004 | Terbrueggen et al. |
| 2004/0064342 A1 | 4/2004 | Browne et al. |
| 2004/0075272 A1 | 4/2004 | Kaufman |
| 2004/0078236 A1 | 4/2004 | Stoodley et al. |
| 2004/0081023 A1 | 4/2004 | Ho |
| 2004/0086872 A1 | 5/2004 | Childers et al. |
| 2004/0107022 A1 | 6/2004 | Gomez |
| 2004/0111298 A1 | 6/2004 | Schoenberg |
| 2004/0121767 A1 | 6/2004 | Simpson et al. |
| 2004/0122707 A1 | 6/2004 | Sabol et al. |
| 2004/0122790 A1 | 6/2004 | Walker et al. |
| 2004/0133705 A1 | 7/2004 | Broussard et al. |
| 2004/0138921 A1 | 7/2004 | Broussard et al. |
| 2004/0138926 A1 | 7/2004 | Ishikawa et al. |
| 2004/0143403 A1 | 7/2004 | Brandon et al. |
| 2004/0151629 A1 | 8/2004 | Pease et al. |
| 2004/0154688 A1 | 8/2004 | Geltser et al. |
| 2004/0158507 A1 | 8/2004 | Meek, Jr. et al. |
| 2004/0176984 A1 | 9/2004 | White et al. |
| 2004/0188523 A1 | 9/2004 | Lunak et al. |
| 2004/0188524 A1 | 9/2004 | Lunak et al. |
| 2004/0193316 A1 | 9/2004 | Lunak et al. |
| 2004/0210341 A1 | 10/2004 | Wallace et al. |
| 2004/0215486 A1 | 10/2004 | Braverman |
| 2004/0220498 A1 | 11/2004 | Li et al. |
| 2004/0224916 A1 | 11/2004 | Dahl et al. |
| 2004/0225203 A1 | 11/2004 | Jemison et al. |
| 2004/0243441 A1 | 12/2004 | Bocionek et al. |
| 2005/0010416 A1 | 1/2005 | Anderson et al. |
| 2005/0013863 A1 | 1/2005 | Lim et al. |
| 2005/0021413 A1 | 1/2005 | Berry et al. |
| 2005/0038558 A1 | 2/2005 | Keene |
| 2005/0053650 A1 | 3/2005 | Chalmers |
| 2005/0060188 A1 | 3/2005 | Valley |
| 2005/0062238 A1 | 3/2005 | Broadfield et al. |
| 2005/0065645 A1 | 3/2005 | Liff et al. |
| 2005/0101841 A9 | 5/2005 | Kaylor et al. |
| 2005/0102159 A1 | 5/2005 | Mondshine |
| 2005/0110268 A1 | 5/2005 | Schone |
| 2005/0118202 A1 | 6/2005 | Yamashita et al. |
| 2005/0147667 A1 | 7/2005 | Rines |
| 2005/0158401 A1 | 7/2005 | Morris |
| 2005/0192487 A1 | 9/2005 | Cosentino et al. |
| 2005/0216313 A1 | 9/2005 | Claud et al. |
| 2005/0218152 A1 | 10/2005 | Simon |
| 2005/0240305 A1 | 10/2005 | Bogash et al. |
| 2005/0260679 A1 | 11/2005 | Kellerman et al. |
| 2005/0261255 A1 | 11/2005 | Serhan et al. |
| 2005/0271596 A1 | 12/2005 | Friedman et al. |
| 2005/0285746 A1 | 12/2005 | Sengupta et al. |
| 2006/0015016 A1 | 1/2006 | Thornton |
| 2006/0028727 A1 | 2/2006 | Moon et al. |
| 2006/0047538 A1 | 3/2006 | Condurso et al. |
| 2006/0064250 A1 | 3/2006 | Goldstein |
| 2006/0073484 A1 | 4/2006 | Mathies et al. |
| 2006/0097516 A1 | 5/2006 | Kozlowski et al. |
| 2006/0099310 A1 | 5/2006 | Koekkoek |
| 2006/0111944 A1 | 5/2006 | Sirmans, Jr. et al. |
| 2006/0129324 A1 | 6/2006 | Rabinoff et al. |
| 2006/0240150 A1 | 10/2006 | Delaney et al. |
| 2006/0260679 A1 | 11/2006 | Aratani et al. |
| 2006/0264780 A1 | 11/2006 | Holmes et al. |
| 2006/0280307 A1 | 12/2006 | Ikushima et al. |
| 2007/0087048 A1 | 4/2007 | Abrams et al. |
| 2007/0136092 A1 | 6/2007 | Jung et al. |
| 2008/0097784 A1 | 4/2008 | Miller et al. |

FOREIGN PATENT DOCUMENTS

| | | |
|---|---|---|
| WO | WO 99/45354 | 9/1999 |
| WO | WO 99/45354 A2 | 9/1999 |
| WO | WO 99/45354 A3 | 9/1999 |
| WO | WO 00/60362 | 10/2000 |
| WO | WO 00/60362 A1 | 10/2000 |
| WO | WO 01/79529 A1 | 10/2001 |
| WO | WO 03/084395 A1 | 10/2003 |
| WO | WO 2004/061085 A3 | 7/2004 |
| WO | WO 2005/041105 A1 | 5/2005 |
| WO | WO 2005/062849 A2 | 7/2005 |
| WO | WO 2006/032044 A3 | 3/2006 |
| WO | WO 2007/061838 A2 | 5/2007 |

OTHER PUBLICATIONS

Bassaganya-Riera, J.; Hontecillas, R.; Wannemuehler, M.; "Nutrition impact of conjugated linoleic acid: A model functional food ingredient"; In Vitro Cellular and Development Biology-Plant; May 2002; pp. 241-246 (pp. 1-2); vol. 38, No. 3; Online ISSN 1475-2689; Springer; at: http://www.ingentaconnect.com/content/klu/ivp/2002/00000038/00000003/02002295?crawler=true; printed on Jun. 25, 2007.

Blum, K; Meshkin, B; Downs, BW; "DNA based customized Nutraceutical 'gene therapy' utilizing a genoscore: a hypothesized paradigm shift of a novel approach to the diagnosis, stratification, prognosis and treatment of inflammatory processes in the human"; Med. Hypotheses; Bearing dates of 2006 and Jan. 5, 2006; pp. 1008-1018 (pp. 1-2); vol. 66, No. 5; PubMed; located at: http://www.ncbi.nlm.nih.gov/sites/entrez?db=pubmed; printed on Jun. 11, 2007.

Chen, ZP; Schell, JB; Ho, CT; Chen, KY; "Green tea epigallocatechin gallate shows a pronounced growth inhibitory effect on cancerous cells but not on their normal counterparts"; Cancer Lett.; Jul. 17, 1998; pp. 173-179 (pp. 1-2); vol. 129, No. 2; PubMed; at: http://www.ncbi.nlm.nih.gov/sites/entrez?db=pubmed; printed on Jun. 22, 2007.

Dumont, Yannick; D'Amours, Martin; Lebel, Marcel; Larivière, Richard; "Original Article: Supplementation with a low dose of L-arginine reduces blood pressure and endothelin-1 production in hypertensive uraemic rats"; Nephrol Dial Transplant; Bearing a date of 2001; pp. 746-754; vol. 16; European Renal Association-European Dialysis and Transplant Association.

Gosslau, A; Chen, M; Ho, Ci-T; Chen, KY; "Translational Therapeutics: A methoxy derivative of resveratrol analogue selectively induced activation of the mitochondrial apoptotic pathway in transformed fibroblasts"; British Journal of Cancer; Bearing dates of 2005 and Jan. 25, 2005; pp. 513-521 (pp. 1-2); vol. 92; Online ISSN: 1532-1827; Cancer Research UK; at: http://www.nature.com/bjc/journal/v92/n3/abs/6602300a.html; printed on Jun. 22, 2007.

Hobbs, Charlotte, A.; Sherman, Stephanie, L.; Yi, Ping; Hopkins, Sarah E.; Torfs, Claudine P.; Hine, R. Jean; Pogribna, Marta; Rozen, Rima; James, S. Jill; "Polymorphisms in Genes Involved in Folate Metabolism as Maternal Risk Factors for Down Syndrome"; Am. J. Hum. Genet.; Bearing a date of 2000; pp. 623-630; vol. 67; The American Society of Human Genetics.

Hodgson, JM; Watts, GF; Playford, DA; Burke, V; Croft, KD; "Original Communication-Coenzyme $Q_{10}$ improves blood pressure and glycaemic control: a controlled trial in subjects with type 2 diabetes"; European Journal of Clinical Nutrition; Bearing a date of 2002; pp. 1137-1142; vol. 56; Nature Publishing Group; at: www.nature.com/ejcn.

James, S. Jill; Pogribna, Marta; Pogribny, Igor P.; Melnyk, Stepan; Hine, R. Jean; Gibson, James B.; Yi, Ping; Tafoya, Dixie L.; Swenson, David H.; Wilson, Vincent L.; Gaylor, David W.; "Abnormal folate metabolism and mutation in the methylenetetrahydrofolate reductase gene may be maternal risk factors for Down syndrome"; The American Journal of Clinical Nutrition; Bearing a date of 1999; pp. 495-501; vol. 70; American Society for Clinical Nutrition; at: www.ajcn.org; printed on Jun. 11, 2007.

Kanauchi, O; Igarashi, K; Ogata, R; Mitsuyama, K; Andoh, A; "A yeast extract high in bioactive peptides has a blood-pressure lowering effect in hypertensive model"; Curr. Med. Chem.; Bearing a date of 2005; pp. 3085-3090 (p. 1); vol. 12, No. 26; PubMed; at: http://www.ncbi.nlm.nih.gov/sites/entrez?db=pubmed; printed on May 17, 2007.

Katan, Martijn B.; "Editorial: Health claims for functional foods"; BMJ; Bearing a date of Jan. 24, 2004; pp. 180-181 (pp. 1-3); vol. 328; BMJ Publishing Group Ltd.; at: http://www.bmj.com/cgi/content/full/328/7433/180; printed on Jun. 11, 2007.

Khosh, Farhang; Khosh, Mehdi; "Natural Approach to Hypertension"; Alternative Medicine Review; Bearing a date of 2001; pp. 590-600; vol. 6, No. 6; Thorne Research, Inc.

Kitajka, Klára; Sinclair, Andrew J.; Weisinger, Richard S.; Weisinger, Harrison S.; Mathai, Michael; Jayasooriya, Anura P.; Halver, John E.; Puskás, László G.; "Biochemistry: Effects of dietary omega-3 polyunsaturated fatty acids on brain gene expression"; PNAS; Bearing a date of Jul. 27, 2004; pp. 10931-10936; vol. 101, No. 30; The National Academy of Sciences of the USA; at: www.pnas.org/cgi/doi/10.1073/pnas.0402342101.

Lu, Jiebo; Ho, Chi-Tang; Ghai, Geetha; Chen, Kuang Yu; "Differential Effects of Theaflavin Monogallates on Cell Growth, Apoptosis, and Cox-2 Gene Expression in Cancerous versus Normal Cells"; Cancer Research; Bearing a date of Nov. 15, 2000; pp. 6465-6471; vol. 60.

Lu, Jiebo; Ho, Chi-Tang; Ghai, Geetha; Chen, Kuang Yu; "Resveratrol analog, 3,4,5,4',-tetrahydroxystilbene, differentially induces pro-apoptotic p53/Bax gene expression and inhibits the growth of transformed cells but not their normal counterparts"; Carcinogenesis; Bearing a date of 2001; pp. 321-328; vol. 22, No, 2; Oxford University Press.

Lucock, Mark; "Clinical Review: Science, Medicine, and the future—Is folic acid the ultimate functional food component for disease prevention?" BMJ; Bearing a date of Jan. 24, 2004; pp. 211-214 (pp. 1-9); vol. 328; BMJ Publishing Group Ltd.; at: http://www.bmj.com/cgi/content/full/328/7433/211; printed on Jun. 22, 2007.

Ma, Jing; Stampfer, Meir J.; Giovannucci, Edward; Artigas, Carmen; Hunter, David J.; Fuchs, Charles; Willett, Walter C.; Selhub, Jacob; Hennekens, Charles H.; Rozen, Rima; "Methylenetetrahydrofolate Reductase Polymorphism, Dietary Interactions, and Risk of Colorectal Cancer"; Cancer Research; Bearing a date of Mar. 15, 1997; pp. 1098-1102; vol. 57.

Malnick, Stephen; Goland, Sorel; "Folic acid as ultimate in disease prevention Beware of vitamin B12 deficiency"; BMJ; Bearing a date of Mar. 27, 2004; pp. 1-2; vol. 328, No. 769; BMJ Publishing Group Ltd.; at: http://www.bmj.com/cgi/content/full/328/7442/769; printed on Jun. 25, 2007.

Mills, JL; Kirke, PN; Molloy AM; Burke, H; Conley, MR; Lee, YJ; Mayne, PD; Weir, DG; Scott, JM; "Methylenetetrahydrofolate reductase thermolabile variant and oral clefts"; Am. J. Med. Genet.; Bearing a date of Sep. 3, 1999; pp. 71-74 (p. 1); vol. 86, No. 1; PubMed; at: http://www.ncbi.nlm.nih.gov/sites/entrez; printed on Jun. 25, 2007.

Mullan, Brian A.; Young, Ian S.; Fee, Howard; McCance, David R.; "Ascorbic Acid Reduces Blood Pressure and Arterial Stiffness in Type 2 Diabetes"; Hypertension—Journal of the American Heart Association; Bearing dates of Oct. 21, 2002 and 2002; pp. 804-809 (pp. 1-7); vol. 40; Online ISSN 1524-4563; American Heart Association, Inc.; at: http://hyper.ahajournals.org/cgi/content/full/40/6/804; printed on May 17, 2007.

Park, YK; Kim, JS; Kang, MH; "Concord grape juice supplementation reduces blood pressure in Korean hypertensive men: double-blind, placebo controlled intervention trial"; Biofactors; Bearing a date of 2004; pp. 145-147 (p. 1); vol. 22, Nos. 1-4; PubMed; at: http://www.ncbi.nlm.nih.gov/sites/entrez?cmd=Retrieve&db=PubMed&dopt=Citation&list_uids=15630270; printed on May 17, 2007.

Shizuka, F; Kido, Y; Nakazawa, T; Kitajima, H; Aizawa, C; Kayamura, H; Ichijo, N; "Antihypertensive effect of gamma-amino butyric acid enriched soy products in spontaneously hypertensive rats"; Biofactors; Bearing a date of 2004; pp. 165-167 (p. 1); vol. 22, Nos. 1-4; PubMed; at: http://www.ncbi.nlm.nih.gov/sites/entrez?cmd=Retrieve&db=PubMed&list_uids=15630275&dopt=Abstract; printed on May 17, 2007.

Steenge, Gery R.; Verhoef, Petra; Katan, Martijn B.; "Human Nutrition and Metabolism—Betaine Supplementation Lowers Plasma Homocysteine in Healthy Men and Women"; The Journal of Nutrition; Bearing a date of 2003; pp. 1291-1295; vol. 133; American Society for Nutritional Sciences; at: jn.nutrition.org; printed on May 17, 2007.

Subbiah, MT; "Nutrigenetics and Nutraceuticals: the next wave riding on personalized medicine"; Transl Res.; Bearing a date of Feb. 2007; pp. 55-61 (pp. 1-2); vol. 149, No. 2; PubMed; at: http://www.ncbi.nlm.nih.gov/sites/entrez; printed on Jun. 25, 2007.

Vieira Da Costa, VA; Vianna, LM; "Effect of alpha-tocopherol supplementation on blood pressure and lipidic profile in streptozotocin-induced diabetes mellitus in spontaneously hypertensive rats"; Clin. Chim. Acta.; Bearing a date of Jan. 2005; pp. 101-104 (p. 1); vol. 351, Nos. 1-2; PubMed; at: http://www.ncbi.nlm.nih.gov/sites/entrez; printed on May 17, 2007.

Wan, Ruiqian; Camandola, Simonetta; Mattson, Mark P.; "Dietary supplementation with 2-deoxy-d-glucose improves cardiovascular and neuroendocrine stress adaptation in rats"; Am. J. Physiol Heart Circ. Physiol; Bearing dates of Oct. 10, 2003 and Apr. 26, 2004; pp. 1-13; vol. 287; American Physiological Society; at: http://ajpheart.physiology.org/cgi/content/full/287/3/H1186; printed on May 17, 2007.

West, SG; Likos-Krick, A; Brown, P; Mariotti, F; "Oral L-arginine improves hemodynamic responses to stress and reduces plasma homocysteine in hypercholesterolemic men"; J. Nutr.; Bearing a date of Feb. 2005; pp. 212-217 (p. 1-2); vol. 135, No. 2; PubMed; at: http://www.ncbi.nlm.nih.gov/sites/entrez?cmd=Retrieve&db=pubmed&dopt=Abstract&list_uids=15671215; printed on Jun. 25, 2007.

Wilson, A; Platt, R; Wu, Q; LeClerc, D; Christensen, B; Yang, H; Gravel, RA; Rozen, R; "A common variant in methionine synthase reductase combined with low cobalamin (vitamin B12) increases risk for spina bifida"; Mol. Genet. Metab.; Bearing a date of Aug. 1999; pp. 317-323 (p. 1); vol. 67, No. 4; PubMed; at: http://www.ncbi.nlm.nih.gov/sites/entrez; printed on Jun. 25, 2007.

PCT International Search Report; International App. No. PCT/US07/25379; May 13, 2008; 1-2.

PCT International Search Report; International App. No. PCT/US07/25417; May 14, 2008; pp. 1-3.

PCT International Search Report; International App. No. PCT/US07/25417; May 19, 2008; pp. 1-2.

PCT International Search Report; International App. No. PCT/US2007/025450; May 23, 2008; pp. 1-2.

PCT International Search Report; International App. No. PCT/US06/47835; Jul. 14, 2008; pp. 1-2.

U.S. Appl. No. 11/900,660, Jung et al.
U.S. Appl. No. 11/900,649, Jung et al.
U.S. Appl. No. 11/900,637, Jung et al.
U.S. Appl. No. 11/893,608, Jung et al.
U.S. Appl. No. 11/893,606, Jung et al.
U.S. Appl. No. 11/893,605, Jung et al.
U.S. Appl. No. 11/888,627, Jung et al.
U.S. Appl. No. 11/888,614, Jung et al.
U.S. Appl. No. 11/888,613, Jung et al.

Brüssow, Harald; "Phage Therapy: the *Escherichia coli* experience"; Microbiology; 2005; pp. 2133-2140; vol. 151.

Merril, Carl R.; Biswas, Biswajit; Carlton, Richard; Jensen, Nicole C.; Creed, G. Joseph; Zullo, Steve; Adhya, Sankar; "Long-circulating bacteriophage as antibacterial agents"; Proc. Natl. Acad. Sci.; Apr. 1996; pp. 3188-3192; vol. 93.

PCT International Search Report; International App. No. PCT/US2005/033347; Aug. 23, 2006; 4 pages.

PCT International Search Report; International App. No. PCT/US03/41466; Aug. 26, 2004; 2 pages.

PCT International Search Report; International App. No. PCT/US01/09745; Aug. 2, 2001; 1 page.

PCT International Search Report; International App. No. PCT/IL99/00122; Aug. 30, 1999; 2 pages.

"Smart Pillbox Goes Direct to Consumer"; Health Data Management; Bearing dates of Aug. 28, 2007 and Aug. 29, 2007; pp. 1-2; Health Data Management and SourceMedia, Inc.; at: http://healthdatamanagement.com/html/news/NewsStory.cfm?articleId=15652; printed on Aug. 29, 2007.

Woolley, AT et al.; "Functional integration of PCR amplification and capillary electrophoresis in a microfabricated DNA analysis device"; Anal Chem; Bearing a date of Dec. 1, 1996; pp. 4081-4086 (p. 1); vol. 68, No. 23; PubMed; at: http://www.ncbi.nlm.nih.gov; printed on Aug. 2, 2007.

Smith, Stevie; "New Chip Identifies Bird Flu in Humans"; The Tech Herald.com, WOTR Limited; 2008; at: www.thetechherald.com/article/php200813/520/new-chip-identifies-bird-flu-in-humans; Bearing a date of Mar. 25, 2008; printed on Sep. 8, 2008; pp. 1-6.

PCT International Search Report; International App. No. PCT/US07/25451; Sep. 15, 2008; pp. 1-2.

PCT International Search Report; International App. No. PCT/US07/20272; Sep. 15, 2008; pp. 1-2.

PCT International Search Report; International App. No. PCT/US07/20305; Sep. 11, 2008; pp. 1-2.

PCT International Search Report; International App. No. PCT/US07/20283; Sep. 11, 2008; pp. 1-2.

PCT International Search Report; International App. No. PCT/US07/14994; Sep. 9, 2008; pp. 1-2.

PCT International Search Report; International App. No. PCT/US08/07993; Sep. 8, 2008; pp. 1-3.

PCT International Search Report; International App. No. PCT/US06/47451; Sep. 5, 2008; pp. 1-2.

PCT International Search Report; International App. No. PCT/US06/44658; Aug. 29, 2008; pp. 1-2.

PCT International Search Report; International App. No. PCT/US06/44279; Aug. 19, 2008; pp. 1-3.

PCT International Search Report; International App. No. PCT/US06/44283; Aug. 18, 2008; pp. 1-2.

PCT International Search Report; International App. No. PCT/US07/14266; Jul. 21, 2008; pp. 1-2.

U.S. Appl. No. 11/518,540, Jung et al.
U.S. Appl. No. 11/486,998, Jung et al.
U.S. Appl. No. 11/486,973, Jung et al.
U.S. Appl. No. 11/453,571, Jung et al.

"A1C At-Home Test Kit—Introductory Offer (1 per customer, first time buyers Only)"; Amazon.com; Bearing dates of 1996-2006; pp. 1-4; Amazon.com, Inc.; at: http://www.amazon.com/gp/product/B0006JMPRG/ref=sr_11_1/103-2429377-9250503?ie=UTF8; printed on Jul. 10, 2006.

Abrams, Bernard; "Standing Rx packaging on its head"; Packagingdigest.com; Bearing a date of Jun. 2005; pp. 1-3; at http://www.packagingdigest.com/articles/200506/38.php; printed on Jun. 21, 2006.

Actis-Goretta, Lucas; Ottaviani, Javier I.; Fraga, Cesar G.; "Inhibition of Angiotensin Converting Enzyme Activity by Flavanol-Rich Foods"; Journal of Agricultural and Food Chemistry; Bearing a date of 2006; pp. 229-234; vol. 54; American Chemical Society.

"Anemia Tests"; Home Health Testing; Bearing dates of Dec. 1, 2005 and 2000; pp. 1-3; AbDiagnostics, Inc.; at: http://www.homehealthtesting.com/anemia-tests.htm; printed on Jul. 24, 2006.

"Antioxidant Tests"; Home Health Testing; Bearing dates of Dec. 1, 2005 and 2000; pp. 1-2; AbDiagnostics, Inc.; at: http://www.homehealthtesting.com/antioxidant-tests.htm; printed on Jul. 24, 2006.

Appleton, David; Lockwood, Brian; "Building Bones with Nutraceuticals"; The Pharmaceutical Journal; Bearing a date of Jul. 15, 2006; pp. 78-83; vol. 277; at: http://www.pjonline.com/pdf/articles/pj_20060715_bones.pdf; printed on Aug. 22, 2006.

"Blood Testing and Sampling Kits"; BloodBook.com; Bearing dates of Nov. 19, 2005 and 2000-2005; pp. 1-2; at: http://www.bloodbook.com/test-kits.html; printed on Jul. 10, 2006.

"Body Balance: AntiOxidant Check"; Health HomeTest.com; Bearing dates of 2003-2005; pp. 1-4; B Scientific, Inc.; at: http://www.healthhometest.com/product_info.php?products_id=39; printed on Jul. 24, 2006.

"Body Balance: FemaleCheck / Estradiol, Progesterone & Testosterone"; Health HomeTest.com; Bearing dates of 2003-2005; pp. 1-5; B Scientific, Inc.; at: http://www.healthhometest.com/product_info.php?products_id=36; printed on Jul. 24, 2006.

"Body Balance: MaleCheck / Testosterone & DHEA"; Health HomeTest.com; Bearing dates of 2003-2005; pp. 1-4; B Scientific, Inc.; at: http://www.healthhometest.com/product_info.php?manufacturers_id=10&products_id=40; printed on Jul. 24, 2006.

"Body Balance: Mineral Check"; Health HomeTest.com; Bearing dates of 2003-2005; pp. 1-8; B Scientific, Inc.; at: http://www.healthhometest.com/product_info.php?products_id=35; printed on Jul. 24, 2006.

"Body Balance: Performance Check"; Health HomeTest.com; Bearing dates of 2003-2005; pp. 1-7; B Scientific, Inc.; at: http://www.healthhometest.com/product_info.php?products_id=82; printed on Jul. 24, 2006.

"Body Balance: Sleep Check / Melatonin"; Health HomeTest.com; Bearing dates of 2003-2005; pp. 1-4; B Scientific, Inc.; at: http://www.healthhometest.com/product_info.php?products_id=46; printed on Jul. 24, 2006.

"Body Balance: Stress Check / DHEA & Cortisol"; Health HomeTest.com; Bearing dates of 2003-2005; pp. 1-6; B Scientific, Inc.; at: http://www.healthhometest.com/product_info.php-?products_id=43; printed on Jul. 24, 2006.

"Body Building Hormone Tests"; Home Health Testing; Bearing dates of Dec. 1, 2005 and 2000; pp. 1-3; AbDiagnostics, Inc.; at: http://www.homehealthtesting.com/performance-hormone-tests.htm; printed on Jul. 24, 2006.

Bridges, Andrew; "HIV/AIDS patients get 1st once-daily pill"; Associated Press; Bearing a date of 2006; pp. 1-3; Yahoo! Inc.; at http://news.yahoo.com/s/ap/20060712/ap_on_he_me/hiv_one_pill; printed on Jul. 12, 2006.

"Browse by: Product Category"; Hach.com; Bearing a date of 2006; pp. 1-2; Hach Company; at: http://www.hach.com/hc/browse.exploded.product.category/PREVIOUS_BREADCRUMB_ID=/SESSIONID|BzFOVFUzTnpZME1URTBOQ1puZFdWemRFMU-NTZz09QTFOVU1URQ==|; printed on Jul. 14, 2006.

Chen, Haibin; Sholl, David S.; "Predictions of Selectivity and Flux for $CH_4/H_2$ Separations Using Single Walled Carbon Nanotubes as Membranes"; Journal of Membrane Science; Bearing dates of 2005 and 2006; pp. 152-160; vol. 269; Elsevier B.V.; at: www.sciencedirect.com and www.elsevier.com/locate/memsci.

Chiu, KM; Keller, ET; Crenshaw, TD; Gravenstein, S.; "Carnitine and dehydroepiandrosterone sulfate induce protein synthesis in porcine primary osteoblast-like cells"; Calcified Tissue International; Bearing a date of Jun. 1999; pp. 527-533 (pp. 1-2); vol. 64, Issue 6; PubMed; at: http://www.ncbi.nlm.nih.gov/entrez/query.fcgi?cmd=Retrieve&db=PubMed&list_uids=10341026&dopt=Abstract; printed on Aug. 22, 2006.

"Clearrx System: Body"; pp. 1-4; at http://www.index2005.dk/Members/tenamikesy/bodyObject; printed on Jun. 21, 2006.

"Clinical Laboratory: Beckman Coulter clinical systems help to simplify and automate laboratory processes"; Beckman Coulter.com; Bearing dates of 1998-2006; p. 1; Beckman Coulter, Inc.; at: http://www.beckmancoulter.com/products/pr_clinical_lab.asp; printed on Jul. 14, 2006.

Colucci, S; Mori, G; Vaira, S; Brunetti, G; Greco, G; Mancini, L; Simone, GM; Sardelli, F; Koverech, A; Zallone, A; Grano, M; "L-carnitine and isovaleryl L-carnitine fumarate positively affect human osteoblast proliferation and differentiation in vitro"; Calcified Tissue International; Bearing a date of Jun. 2005; pp. 458-465 (pp. 1-2); vol. 76, Issue 6; PubMed; at: http://www.ncbi.nlm.nih.gov/entrez/query.fcgi?cmd=Retrieve&db=PubMed&list_uids = 15906015&dopt=Abstract; printed on Aug. 22, 2006.

"Confidential Home DNA Infidelity Testing, Infidelity Test Kit"; Gtldna.com; Bearing dates of Jul. 10, 2006 and 2002-2005; pp. 1-3; The Genetic Testing Laboratories, Inc.; at: http://www.gtldna.com/infidelity.html; printed on Jul. 10, 2006.

Davidow, Julie; "Surge in home diagnostic kits provides doctor in a box"; Seattlepi.com; Bearing dates of Mar. 29, 2006 and 1996-2006; pp. 1-4; Seattle Post-Intelligencer; at: http://seattlepi.nwsource.com/health/264716_hometesting29.html; printed on Jul. 10, 2006.

Demello, Andrew J.; "Microfluidics: DNA Amplification Moves On"; Nature; Bearing dates of Mar. 6, 2003 and 2003; pp. 28-29; vol. 422; Nature Publishing Group; at: www.nature.com/nature.

"Direct to Consumer Blood Test Index"; PreventiveLabs.com; Bearing a date of 2004; pp. 1-6; Preventive Services, LLC; at: http://www.preventivelabs.com/lab_test/blood_test.cfm; printed on Jul. 10, 2006.

"DR / 2400 Portable Spectrophotometer, 115 Vac"; Hach.com; Bearing a date of 2006; p. 1; Hach Company; at: http://www.hach.com/hc/search.product.details.invoker/PackagingCode=5940000/NewLinkLabel=DR%26frasl%3B2400+Portable+Spectrophotometer%2C+115+Vac/PREVIOUS_BREADCRUMB_ID=HC_SEARCH_KEYWORD/SESSIONID|BzFOVFUzTnpFMk56WXINU1puZFdWemRFTk-9Vdz09QTFsTk1URQ==|; printed on Jul. 14, 2006.

"DR 5000 UV-VIS Spectrophotometer (115 Vac)"; Hach.com; Bearing a date of 2006; p. 1; Hach Company; at: http://www.hach.com/hc/search.product.details.invoker/PackagingCode=DR5000-01/NewLinkLabel=DR+5000+UV-Vis+Spectrophotometer%2C+115+Vac/PREVIOUS_BREADCRUMB_ID=HC_SEARCH_BROWSE_PRODUCTSpectrophotometersColorimeters/SESSIONID|B3hOVFUxTnpjeE5qYzJNakVtWjNWbGMzUkR-UZz09QWxOWIRURO==|; printed on Jul. 14, 2006.

"Drugstore.com—online pharmacy & drugstore, prescriptions filled"; drugstore.com; Bearing dates of 1999-2006; pp. 1 (Sheets 1-3), pp. 2 (Sheets 1-4), pp. 3 (Sheets 1-2) (pp. total 1-9); drugstore.com, inc.; at: http://www.drugstore.com/search/search.asp?searchtype=1&trx=28198&trxpl=60&ipp=20&srchtree=1&search=home+test+kit&Go.x=17&Go.y=16; printed on Jul. 10, 2006.

Duffy, SJ; Vita, JA; "Effects of phenolics on vascular endothelial function"; Current Opinion in Lipidology; Bearing a date of Feb. 2003; pp. 21-27 (p. 1); vol. 14, Issue 1; PubMed; at: http://www.ncbi.nlm.nih.gov/entrez/query.fcgi?cmd=Retrieve&db=PubMed&list_uids=12544657&dopt=Abstract; printed on Aug. 22, 2006.

Eskin, N.A. Michael; Dictionary of Nutraceuticals and Functional Foods (Functional Foods and Nutraceuticals); Bearing a date of Dec. 19, 2005; 520 pages; ISBN No. 0849315727; CRC Press.

"Family Age Groups"; testsymptomsathome.com; pp. 1-4; at: http://www.testsymptomsathome.com/family_age_groups.asp; printed on Jul. 10, 2006.

Fan, Chunhai; Plaxco, Kevin W.; Heeger, Alan J.; "Electrochemical interrogation of conformational changes as a reagentless method for the sequence-specific detection of DNA"; PNAS; Bearing a date of Aug. 5, 2003; pp. 9134-9137; vol. 100, No. 16; at: www.pnas.org/cgi/doi/10.1073/pnas.1633515100.

"FDA OKs 3-Drug Combo Pill to Treat HIV"; Bearing a date of Jun. 30, 2006; pp. 1-2; FoxNews.com; at http://www.foxnews.com/wires/2006Jun30/0,4670,AIDSRelief,00.html; printed on Jun. 30, 2006.

Felkey, Bill G.; Berger, Bruce A.; Krueger, Kem P.; "The Pharmacist's Role in Treatment Adherence—Part 5: The Impact of Pharmacy-Specific Technology"; U.S. Pharmacist; Bearing dates of 2005, 2000-2005; and a posted date of Aug. 18, 2005; pp. 36-39 (pp. 1-6); vol. 30:08; Jobson Publishing, L.L.C.; at: http://www.uspharmacist.com/index.asp?show=article&page=8_1547.htm; printed on Nov. 13, 2005.

"Female Hormone Tests"; Home Health Testing; Bearing dates of Dec. 1, 2005 and 2000; pp. 1-3; AbDiagnostics, Inc.; at: http://www.homehealthtesting.com/female-hormone-tests.htm; printed on Jul. 24, 2006.

Fitzgerald, Katherine A.; O'Neill, Luke A.J.; Gearing, Andy J.H.; Callard, Robin E.; "The Cytokine Factsbook"; Bearing a date of Sep. 2001; 515 pages; 2nd Edition; ISBN No. 0121551423; Academic Press; San Francisco, CA.

Gao, Huajian; Kong, Yong; "Simulation of DNA-Nanotube Interactions"; Annual Review of Materials Research.; Bearing a date of 2004; pp. 123-150 (33 total pages); vol. 34; Annual Reviews.

Gennaro, Alfonso R. (Ed); Remington: The Science and Practice of Pharmacy; Bearing a date of Dec. 15, 2000; 2077 pages; 20$^{th}$ Edition; ISBN No. 0683306472; Lippincott Williams and Wilkins; Philadelphia, PA.

Gruenewald, Tara L.; Seeman, Teresa E.; Ryff, Carol D.; Karlamangla, Arun S.; Singer, Burton H.; "Combinations of biomarkers predictive of later life mortality"; PNAS; Bearing dates of Sep. 19, 2006 and 2006; pp. 14158-14163; vol. 103, No. 38; The National Academy of Sciences of the USA; at http://www.pnas.org/cgi/doi/10.1073/pnas.0606215103.

"Heart-Help's Handbook . . . Living with CM & CHF (Cardiomyopathy & Congestive Heart Failure)"; Bearing a date of Sep. 23, 2001; pp. 1-5; at: http://www.heart-help.net/handbook.html; printed on Nov. 13, 2005.

Heller, Daniel A.; Jeng, Esther S.; Yeung, Tsun-Kwan; Martinez, Brittany M.; Moll, Anthonie E.; Gastala, Joseph B.; Strano, Michael S.; "Optical Detection of DNA Conformational Polymorphism on Single-Walled Carbon Nanotubes"; Science; Bearing a date of Jan. 27, 2006; pp. 508-511; vol. 311; at: www.sciencemag.org.

Holt, Jason K.; Park, Hyung Gyu; Wang, Yinmin; Stadermann, Michael; Artyukhin, Alexander B.; Grigoropoulos, Costas P.; Noy, Aleksandr; Bakajin, Olgica; "Fast Mass Transport Through Sub-2-Nanometer Carbon Nanotubes"; Science; Bearing a date of May 19, 2006; pp. 1034-1037; vol. 312; at: www.sciencemag.org.

"Home Allergy Tests"; Home Health Testing; Bearing dates of Dec. 1, 2005 and 2000; pp. 1-3; AbDiagnostics, Inc.; at: http://www.homehealthtesting.com/allergy-tests.htm; printed on Jul. 24, 2006.

"Home DNA Maternity Testing, Test Kit, Blood Paternity Testing"; Gtldna.com; Bearing dates of 2002-2005; pp. 2-5; The Genetic Testing Laboratories, Inc.; at: http://www.gtldna.com/maternitytest.html; printed on Jul. 10, 2006.

"Home DNA Prenatal Paternity, Maternity, Siblingship Test, Twin Zygosity, Kinship, Immigration DNA Testing"; Gtldna.com; Bearing dates of Jul. 10, 2006 and 2002-2005; pp. 1-5; The Genetic Testing Laboratories, Inc.; at: http://www.gtldna.com/dnatests.html; printed on Jul. 10, 2006.

"Home Test Kits, Blood Groups, Diabetes, Menopause, Prostate, Osteoporosis"; WorldWideShoppingMall.co.uk; pp. 1-2; World Wide Shopping Mall (WWSM); at: http://www.worldwideshoppingmall.co.uk/Body-Soul/shelves/home...; printed on Jul. 10, 2006.

"Home Test Kits, Hepatitis Test, HIV Test, Blood Type Test"; Quick Medical: Professional and Home Health Products; Bearing a date of 2006; pp. 1-2; at: http://www.quickmedical.com/monitors/blood_testing/; printed on Jul. 10, 2006.

"Home Test Kits"; PriceGrabber.com; pp. 1 (Sheets 1-5), pp. 2 (Sheets 1-4), pp. 3 (1-5), pp. 4 (Sheets 1-3) (pp. total 1-17); PriceGrabber.com, Inc.; at: http://www.pricegrabber.com/search_attrib.php/page_id=1970; printed on Jul. 10, 2006.

"Hormone Tests"; Home Health Testing; Bearing dates of Dec. 1, 2005 and 2000; pp. 1-2; AbDiagnostics, Inc.; at: http://www.homehealthtesting.com/hormone-tests.htm?gcnd-civ; printed on Jul. 24, 2006.

"Hormone Test Kit-Blood"; The Official Web Site of John R. Lee, MD: Your Information Source for Natural Hormone Balance and Natural HRT; pp. 1-3; Hormones Etc.; at: http://www.johnleemd.com/store/prod_btest.html; printed on Jul. 10, 2006.

"Instant Anemia Test"; Health HomeTest.com; Bearing dates of 2003-2005; pp. 1-9; B Scientific, Inc.; at: http://www.health-hometest.com/product_info.php?products_id=81; printed on Jul. 24, 2006.

"Introducing Integrated Instrument + Reagent Analysis: Hach DR 5000™ UV-VIS Spectrophotometer and DR 2800™ Portable Spectrophotometer + new Hach TNTplus™ Vial Reagents"; Hach.com; Bearing a date of 2006; pp. 1-3; Hach Company; at: http://www.hach.com/photometry; printed on Jul. 14, 2006.

Jain, KK; "Conference Scene: Lab-on-a-Chip and Microarrays: Discovery and Development"; Pharmacogenomics; Bearing a date of 2003; pp. 123-125; vol. 4, No. 2; Ashley Publications Ltd; at: www.pharmaco-genomics.com.

Jarvius, Jonas; DNA Tools and Microfluidic Systems for Molecular Analysis; Digital Comprehensive Summaries of Uppsala Dissertations from the Faculty of Medicine 161; Bearing a date of 2006; pp. 1-66; ISBN 91-554-6616-8; Acta Universitatis Upsaliensis Uppsala.

Keung, WM; "Anti-dipsotropic isoflavones: the potential therapeutic agents for alcohol dependence"; Medicinal Research Reviews; Bearing a date of Nov. 2003; pp. 669-696 (pp. 1-2); vol. 23, Issue 6; PubMed; at: http://www.ncbi.nlm.nih.gov/entrez/query.fcgi?cmd=Retrieve&db=PubMed&list_uids=12939789&dopt=Abstract; printed on Aug. 22, 2006.

Klinge, CM; Blankenship, KA; Risinger, KE; Bhatnagar, S; Noisin, EL; Sumanasekera, WK; Zhao, L; Brey, DM; Keynton, RS;

"Resveratrol and estradiol rapidly activate MAPK signaling through estrogen receptors alpha and beta in endothelial cells"; The Journal of Biological Chemistry; Bearing a date of Mar. 4, 2005; pp. 7460-7468 (pp. 1-2); vol. 280, Issue 9; PubMed; at: http://www.ncbi.nlm.nih.gov/entrez/query.fcgi?cmd=Retrieve&db=PubMed&list_uids=15615701&dopt=Abstract; printed on Aug. 22, 2006.

Li, JX; Xue, B; Chai, Q; Liu, ZX; Zhao, AP; Chen, LB; "Antihypertensive effect of total flavonoid fraction of *Astragalus complanatus* in hypertensive rats"; The Chinese Journal of Physiology; Bearing a date of Jun. 30, 2005; pp. 101-106 (pp. 1-2); vol. 48, Issue 2; PubMed; at: http://www.ncbi.nlm.nih.gov/entrez/query.fcgi?cmd=Retrieve&db=PubMed&list_uids=16201455&dopt=Abstract; printed on Aug. 22, 2006.

Lin, RC; Guthrie, S; Xie, CY; Mai, K; Lee, DY; Lumeng, L; Li, TK; "Isoflavonoid compounds extracted from *Pueraria lobata* suppress alcohol preference in a pharmacogenetic rat model of alcoholism"; Alcoholism, Clinical & Experimental Research; Bearing a date of Jun. 1996; pp. 659-663 (pp. 1-2); vol. 20, Issue 4; PubMed; at: http://www.ncbi.nlm.nih.gov/entrez/query.fcgi?CMD=Display&DB=pubmed; printed on Aug. 22, 2006.

Machha, A; Mustafa, MR; "Chronic treatment with flavonoids prevents endothelial dysfunction in spontaneously hypertensive rat aorta"; Journal of Cardiovascular Pharmacology; Bearing a date of Jul. 2005; pp. 36-40 (p. 1); vol. 46, Issue 1; PubMed; at: http://www.ncbi.nlm.nih.gov/entrez/query.fcgi?CMD=Display&DB=pubmed; printed on Aug. 22, 2006.

"Male Hormone Tests"; Home Health Testing; Bearing dates of Dec. 1, 2005 and 2000; pp. 1-2; AbDiagnostics, Inc.; at: http://www.homehealthtesting.com/male-hormone-tests.htm; printed on Jul. 24, 2006.

Mangels, Reed; "Vitamin B12 in the Vegan Diet"; The Vegetarian Resource Group: Nutrition; Bearing dates of 1996-2003 and Jun. 20, 2006; pp. 1-3; The Vegetarian Resource Group; at http://www.vrg.org/nutrition/b12.htm; printed on Jul. 7, 2006.

McClatchey, Kenneth D.; "Clinical Laboratory Medicine"; Bearing a date of Jan. 15, 2002; 1693 pages; 2nd Edition; ISBN No. 0683307517; Lippincott Williams & Wilkins; Philadelphia, PA.

"Mineral & Toxic Element Tests"; Home Health Testing; Bearing dates of Dec. 1, 2005 and 2000; pp. 1-3; AbDiagnostics, Inc.; at: http://www.homehealthtesting.com/mineral-tests.htm; printed on Jul. 24, 2006.

Morrow, Daniel G.; Leirer, Von O.; Andrassy, Jill M.; "Using icons to convey medication schedule information"; Abstract; Science Direct; Bearing dates of Aug. 1996, May 3, 1999 and 2000; pp. 1-2; vol. 27, Issue 4; Elsevier Ltd.; at http://www.sciencedirect.com/science?_ob=ArticleURL&_udi=B6V1W-3WCSSG5-5&_coverDate=08%2F31%2F1996&_alid=413837048&_rdoc=1&_fmt=&_orig=search&_qd=1&_cdi=5685&_sort=d&view=c&_acct=C000050221&_version=1&_urlVersion=0&_userid=10&md5=8a92d091167ef0d84c80fe26ae9fdbae; printed on Jun. 7, 2006.

Morrow, Daniel G.; Weiner, Michael; Young, James; Steinley, Douglas; Deer, Melissa; Murray, Michael D.; "Improving Medication Knowledge Among Older Adults with Heart Failure: A Patient-Centered Approach to Instruction Design"; The Gerontologist; Bearing a date of 2005; pp. 545-552; vol. 45, No. 4; Practice Concepts; The Gerontological Society of America.

"Nano World: Fast Flow Through Nanotube Membranes (Update)"; Physorg.com; Bearing a date of 2006; pp. 1-2; United Press International; at: www.physorg.com/news67262683.html.

Nissen, David (Ed); Mosby's Drug Guide; Bearing a date of 2004; ISBN No. 0-323-02872-1; Mosby, Inc: Elsevier; St. Louis, MO.

"Occult Blood (stool)—Take-Home Test Kit—$25"; St. Vincent Healthcare; Bearing a date of 2006; p. 1; at: http://www.svh-mt.org/services/all_health/labcheck.occult_blood.htm; printed on Jul. 10, 2006.

"OnTime-RX Medication Reminders"; Bearing dates of 2000-2004; pp. 1-4; AmeliaPlex, Inc.; Orlando, FL; at: http://www.ontimerx.com/PDA/index.asp; printed on Nov. 13, 2005.

"Ovulation Predictor: Home Testing Kits"; Pharm.uky.edu; pp. 1-2; at: http://www.pharm.uky.edu/hometest/Ovulate/OHP.html; printed on Jul. 10, 2006.

"Pain Relief / Injuries / Home Test Kits"; Round-Earth.com; pp. 1-2; Round Earth Publishing; at: http://roundearth.stores.yahoo.net/relaxers.html; printed on Jul. 10, 2006.

"Personal Test Kits: Hormone Saliva Test, Home Hormone Test Kit"; Womenshealth.com; Bearing a date of 2005; pp. 1-3; Women's Health America, Inc.; at: http://www.womenshealth.com/personaltestkit.html; printed on Jul. 10, 2006.

Physicians' Desk Reference; The PDR Family Guide to Nutritional Supplements: An Authoritative A-to-Z Resource on the 100 Most Popular Nutritional Therapies and Nutraceuticals; Bearing a date of Nov. 2003; 3000 pages; 58$^{th}$ Edition; ISBN No. 1563634724; Thomson PDR; Montvale, NJ.

Physicians' Desk Reference; The PDR Family Guide to Nutritional Supplements: An Authoritative A-to-Z Resource on the 100 Most Popular Nutritional Therapies and Nutraceuticals; Bearing a date of Nov. 27, 2001; 352 pages; 1$^{st}$ Edition; ISBN No. 0345433769; Ballantine Books.

Pregnancy Test, Ovulation Test, Drug Test by Medimpex; Bearing a date of 2002; pp. 1-3; Medimpex United Inc.; at: http://www.meditests.com/; printed on Jul. 10, 2006.

"Probiotics Basics"; Bearing a date of 2004; pp. 1-11; CDRF, Dairy & Food Culture Technologies; at: http://www.usprobiotics.org/basics/; printed on Jul. 7, 2006.

"Quality Standards Issued for Testing Herbal Products"; ScienceDaily; Bearing dates of Apr. 18, 2006 and 1995-2006; pp. 1-2; ScienceDaily LLC; at: http://www.sciencedaily.com/releases/2006/04/060418011332.htm; printed on Jul. 14, 2006.

Rapport, Lisa; Lockwood, Brian; Nutraceuticals; Bearing a date of Dec. 2001; 184 pages; 1$^{st}$ Edition; ISBN No. 0 85369 503 2; Pharmaceutical Press.

Roberts, Arthur J.; Subak-Sharpe, Genelle; O'Brien, Mary E.; Nutraceuticals: The Complete Encyclopedia of Supplements, Herbs, Vitamins, and Healing Foods; Bearing a date of Jan. 9, 2001; 669 pages; 1$^{st}$ Edition; ISBN No. 0399526323; Perigee Trade.

Sambrook, Joseph; Russell, David W.; "Molecular Cloning: A Laboratory Manual"; Bearing a date of Jan. 15, 2001; 2,344 pages; 3 Edition; ISBN 0-87969-577-3; Cold Spring Harbor Laboratory Press.

Samuel, Buck S.; Gordon, Jeffrey I.; "A Humanized Gnotobiotic Mouse Model of Host-Archaeal-Bacterial Mutualism"; PNAS; Bearing dates of 2006, Mar. 16, 2006, May 17, 2006 and Jun. 27, 2006; pp. 10011-10016; vol. 103, No. 26; The National Academy of Sciences of the USA; at: www.pnas.org/cgi/doi/10.1073/pnas.0602187103.

Sarkar, FH; Adsule, S; Padhye, S; Kulkarni, S; Li, Y; "The role of genistein and synthetic derivatives of isoflavone in cancer prevention and therapy"; Mini Reviews in Medicinal Chemistry; Bearing a date of Apr. 2006; pp. 401-407 (pp. 1-2); vol. 6, Issue 4; PubMed; at: http://www.ncbi.nlm.nih.gov/entrez/query.fcgi?CMD=Display&DB=pubmed; printed on Aug. 22, 2006.

"Search Results"; Health HomeTest.com; Bearing dates of 2003-2005; pp. 1-2; B Scientific, Inc.; at: http://www.healthhometest.com/index.php?cPath=40; printed on Jul. 24, 2006.

Sholl, David S.; Johnson, J. Karl; "Materials Science: Making High-Flux Membranes with Carbon Nanotubes"; Science; Bearing a date of May 19, 2006; pp. 1003-1004; vol. 312; AAAS; at: www.sciencemag.org.

"Single Parameter Test Kits"; Hach.com; Bearing a date of 2006; pp. 1-9; Hach Company; at: http://www.hach.com/hc/browse.exploded.product.category.catalog/PRODCAT0033/NewLinkLabel=Single+Parameter+Test+Kits/PREVIOUS_BREADCRUMB_ID=HC_SEARCH_BROWSE/SESSIONID|BkUxTIRVM05UQ-TVPVFEzT0NabmRXVnpkRTVEVWc9PUEwdFhNVA==|; printed on Jul. 14, 2006.

Singh-Zocchi, Mukta; Dixit, Sanhita; Ivanov, Vassili; Zocchi, Giovanni; "Single-Molecule Detection of DNA Hybridization"; Bearing a date of Jun. 24, 2003; pp. 7605-7610; vol. 100, No. 13; at: www.pnas.org/cgi/doi/10.1073/pnas.1337215100.

"Sleep Hormone Tests"; Home Health Testing; Bearing dates of Dec. 1, 2005 and 2000; pp. 1-3; AbDiagnostics, Inc.; at http://www.homehealthtesting.com/sleep-tests.htm; printed on Jul. 24, 2006.

Smith, Ann; Heckelman, Patricia E.; O'Neil, Maryadele J. (Ed); Budavari, Susan (Ed); The Merck Index: An Encyclopedia of Chemicals, Drugs and Biologicals; Bearing a date of Oct. 2001; 2564 pages;

13th Edition; ISBN No. 091191031; John Wiley and Sons and Merck & Co. Inc.; Whitehouse Station, NJ.

Sojourner, Russell J.; Wogalter, Michael S.; "The Influence of Pictorials on Evaluations of Prescription Medication Instructions"; Drug Information Journal; Bearing a date of 1997; pp. 963-972; vol. 31; Drug Information Association, Inc.

"Spectrophotometers and Colorimeters"; Hach.com; Bearing a date of 2006; pp. 1-2; Hach Company; at: http://www.hach.com/hc/browse.exploded.product.category.catalog/PRODCAT0001/NewLinkLabel=Spectrophotometers+%26+Colorimeters/PREVIOUS_BREADCRUMB_ID=HC_SEARCH_BROWSE/SESSIONID|A3INVE14TnpJeUITWm5kVIZ6ZEZCWIQxZEI-NVEUxTIE9PUNUTQ==|; printed on Jul. 14, 2006.

"Stress Hormone Tests"; Health Testing; Bearing dates of Dec. 1, 2005 and 2000; pp. 1-3; AbDiagnostics; Inc.; at: http://www.homehealthtesting.com/stress-hormone-tests.htm; Jul. 24, 2006.

"Talking Medicine Identifiers"; Bearing a date of Jul. 10, 2003; pp. 1-5.

"UV-Vis-NIR Advantage Note"; Bearing a date of May 2005; No. 1; pp. 1-3; Varian, Inc.; at: www.varianinc.com/image/vimage/docs/applications/apps/uv_an1.pdf: printed on Jul. 14, 2006.

"UV-Vis-IR-Raman Spectrophotometers"; Micro Photonics; Bearing a date of Dec. 7, 2005; pp. 1-2; Micro Photonics, Inc.; at: http://www.microphotonics.com/spectrophotometer.html; printed on Jul. 14, 2006.

Wald, NJ; Law, MR; "A strategy to reduce cardiovascular disease by more than 80%"; BMJ; Jun. 28, 2003; pp. 1-6; vol. 326; at: www.bmj.com.

Wallerath, T; Deckert, G; Ternes, T; Anderson, H; Li, H; Witte, K; Forstermann, U; "Resveratrol, a polyphenolic phytoalexin present in red wine, enhances expression and activity of endothelial nitric oxide synthase"; Circulation; Bearing a date of Sep. 24, 2002; pp. 1652-1658 (pp. 1-2); vol. 106, Issue 13; PubMed; at: http://www.ncbi.nlm.nih.gov/entrez/query.fcgi?cmd=Retrieve&db=PubMed&list_uids=12270858&dopt=Abstract; printed on Aug. 22, 2006.

Walji, Rishma; "*Acidophilus* Effects, Benefits and Other Information"; About: Alternative Medicine; bearing a date of 2006; p. 1; About, Inc., A Part of *The New York Times Company*; at: http://altmedicine.about.com/cs/digestiveproblems/a/Acidophilus.htm; printed on Jul. 7, 2006.

Walji, Rishma; "What are Probiotics?"; About: Alternative Medicine; Bearing a date of 2006; p. 1; About, Inc., A part of *The New York Times Company*; at: http://altmedicine.about.com/cs/digestiveproblems/a/Acidophilus_2.htm; printed on Jul. 7, 2006.

Wang, J.; Li, J.; Baca, AJ.; Hu, J.; Zhou, F.; Yan, W.; Pang, DW.; "Amplified Voltammetric Detection of DNA Hybridization via Oxidation of Ferrocene Caps on Gold Nanoparticle/Streptavidin Conjugates"; Anal. Chem.; Bearing a date of Aug. 1, 2003; pp. 3941-3945 (p. 1); vol. 75, No. 15; PubMED; at: http://www.ncbi.nlm.nih.gov/entrez/query.fcgi?cmd=Retrieve&db=PubMed&list_uids=14572067&dopt=Abstract; printed ON Nov. 29, 2006.

"What are Probiotics?"; USProbiotics; Bearing a date of 2004; 1 page; CDRF, Dairy & Food Culture Technologies; at: http://www.usprobiotics.org/mainpageframe.htm; printed on Jul. 7, 2006.

Widdershoven, J.; Van Munster, P.; De Abreu, R.; Bosman, H.; Van Lith, TH.; Van Der Putten-Van Meyel, M.; Motohara, K.; Matsuda, I.; "Four Methods Compared for Measuring Des-Carboxy-Prothrombin (PIVKA-II)"; Clinical Chemistry; Bearing a date of 1987; pp. 2074-2078; vol. 33, No. 11.

Wildman, Robert E.C.; Handbook of Nutraceuticals and Functional Foods; Bearing a date of Nov. 10, 2000; 568 pages; 1st Edition; ISBN No. 0849387345; CRC Press.

Wynn, Susan G.; Emerging Therapies: Using Herbs and Nutraceuticals for Small Animals; Bearing a date of 1999; 160 pages; 1st Edition; ISBN No. 1583260102; American Animal Hospital Assn Press.

Xiao, Yl; Lubin, Arica A.; Baker, Brian R.; Plaxco, Kevin W.; Heeger, Alan J.; "Single-Step Electronic Detection of Femtomolar DNA by Target-Induced Strand Displacement in an Electrode-Bound Duplex"; PNAS; Bearing a date of Nov. 7, 2006; pp. 16677-16680; vol. 103, No. 45; at: www.pnas.org/cgi/doi/10.1073/pnas.0607693103.

PCT International Search Report; International App. No. PCT/US 06/44664; Apr. 14, 2008; pp. 1-3.

PCT International Search Report; International App. No. PCT/ US 06/44269; Sep. 18, 2007; pp. 1-2.

U.S. Appl. No. 11/524,084, Jung et al.
U.S. Appl. No. 11/904,016, Jung et al.
U.S. Appl. No. 11/906,112, Jung et al.
U.S. Appl. No. 11/355,517, Jung et al.
U.S. Appl. No. 11/339,316, Jung et al.
U.S. Appl. No. 11/314,949, Jung et al.
U.S. Appl. No. 11/314,764, Jung et al.
U.S. Appl. No. 11/291,532, Jung et al.
U.S. Appl. No. 11/285,753, Jung et al.
U.S. Appl. No. 11/285,500, Jung et al.
U.S. Appl. No. 11/283,548, Jung et al.

Lagally, E.T. et al.; "Integrated Portable Genetic Analysis Microsystem for Pathogen/Infectious Disease Detection"; Analytical Chemistry; bearing a date of Jun. 1, 2004; pp. 3162-3170; vol. 76, No. 11; © 2004 American Chemical Society.

Leibovici, Leonard et al.; "A Causal Probabilistic Network for Optimal Treatment of Bacterial Infections"; IEEE Transactions on Knowledge and Data Engineering; bearing a date of Jul./Aug. 2000; pp. 517-528; vol. 12, No. 4; © 2000 IEEE.

Edible Science; bearing dates of 2005-2010; pp. 1-2; at: http://www.ediblescience.com; printed on May 13, 2010.

Fightermins; bearing a date of 2010; 1 page; at: http://www.fightermins.com/index.jsp; printed on May 13, 2010.

Ideal Health; "Custom Essentials"; "The Priva Test"; bearing a date of 2010; total of 5 pages; at: http://www.idealhealth.com; printed on May 13, 2010; The Trump Network.

I-Vita; bearing a date of 2009; 1 page; at: http://www.mynutrapack.com/index.html; printed on May 13, 2010.

LifeScript; bearing dates of 1998-2010; 1 page; at: http://vitamins.lifescript.com/Begin.asp?BID=14971&PROMO=zluswiec; printed on May 13, 2010.

Mindell, Earl, Dr.; Vitaganic "Custom-Made Multivitamins"; bearing dates of 2005-2010; 1 page; at: http://drmindell.vitaganic.com/; printed on May 13, 2010.

My Vitamin Clinic; bearing a date of 2010; 1 page; at: http://www.myvitaminclinic.com/index.jsp; printed on May 13, 2010.

MyNutraPack; 1 page; at: http://www.mynutrapack.com/index.html; printed on May 25, 2010.

MyVitaminRx; bearing a date of 2007; 1 page; at: http://www.myvitaminsrx.com/CustomNutrition/CustomNutrition.aspx?ID=MoonlightSpa; printed on May 13, 2010.

Nature Made; pp. 1-2; at: http://www.naturemade.com/; printed on May 13, 2010.

NutriHerb; bearing dates of 2001-2009; pp. 1-2; Nutri Herb, Inc.; at: http://www.nutriherb.net/custom_made_to_order_herbal_vitamins_supplements.html; printed on May 13, 2010.

Pharmative LLC; 1 page; at: http://www.pharmavite.com/index.asp; printed on May 13, 2010.

"Pharmavite LLC Launches New Direct-to-Consumer Company" Press Release; Pharmavite LLC; bearing a date of Sep. 4, 2009; 1 page; at: http://www.pharmavite.com/MediaCenter/MC_PR.asp?ID=164; printed on May 13, 2010.

Signature Supplements; bearing a date of 2009; pp. 1-2; at: http://www.signaturesupplements.com/jsp/main/index.jsp; printed on May 13, 2010; Signature Supplements.

SOYJOY®; bearing a date of 2010; 1 page; at: http://www.soyjoy.com/index.aspx; printed on May 13, 2010; Pharmavite LLC.

Total Health Nutrients; pp. 1-2; at: http://www.totalhealthnutrients.com/ph/index.html; printed on May 13, 2010.

VitaminID.com; bearing a date of 2010; 1 page; at: http://www.vitaminid.com/webapp/wcs/stores/servlet/StoreView?storeId=201&langId=-1; printed on May 25, 2010; Pharmavite Direct LLC.

Vitamins on Demand; bearing a date of 2010; 1 page; at: http://www.vitaminsondemand.com/?gclid=CNbygPut9aACFRYhDQodyGkivw; printed on May 13, 2010.

VitaXact; bearing a date of 2009; 1 page; at: http://www.vitaxact.com; printed on May 13, 2010.

Weil, Andrew, M.D.; "Dr. Weil's Vitamin Advisor & Complete Program Supplements"; bearing a date of 2010; 1 page; at: https://www.drweilvitaminadvisor.com/drw/ecs/Va2/land_goog_08girl.html?aid=999910&aparam=TSAsGoogleApr10VA_vitamins&refcd=GO000000101882154s$_{13}$_vitamins&tsacr=GO3784957603&gclid=CM3NpLzm9aACFRYhDQodyGkivw; printed on May 13, 2010; Weil Lifestyle Custom Pak.

U.S. Appl. No. 12/924,700, Jung et al.

* cited by examiner

METHODS AND SYSTEMS FOR ANALYSIS OF NUTRACEUTICAL ASSOCIATED COMPONENTS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/478,341, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed Jun. 28, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/478,296, entitled COMPUTATIONAL AND/OR CONTROL SYSTEMS RELATED TO INDIVIDUALIZED NUTRACEUTICAL SELECTION AND PACKAGING, naming Edward K. Y. Jung, Royce A. Levien, Robert W. Lord, Mark A. Malamud, John D. Rinaldo, Jr., and Lowell L. Wood, Jr. as inventors, filed Jun. 28, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/515,357, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed Sep. 1, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/523,766, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed Sep. 18, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/523,809, entitled COMPUTATIONAL AND/OR CONTROL SYSTEMS AND METHODS RELATED TO NUTRACEUTICAL AGENT SELECTION AND DOSING, naming Edward K. Y. Jung, Royce A. Levien, Robert W. Lord, Mark A. Malamud, John D. Rinaldo, Jr., and Lowell L. Wood, Jr. as inventors, filed Sep. 18, 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to methods and systems that may be used for analysis of nutraceutical associated components.

SUMMARY

In some embodiments one or more methods are provided that include processing one or more samples with one or more microfluidic chips that are configured for analysis of one or more nutraceutical associated components and detecting the one or more nutraceutical associated components with one or more detection units. In addition to the foregoing, other aspects are described in the claims, drawings, and text forming a part of the present disclosure.

In some embodiments one or more methods are provided that include processing one or more samples with one or more microfluidic chips that are configured for analysis of one or more nutraceutical associated components, detecting the one or more nutraceutical associated components with one or more detection units, and displaying results of the detecting with one or more display units that are operably coupled with the one or more detection units. In addition to the foregoing, other aspects are described in the claims, drawings, and text forming a part of the present disclosure.

In some embodiments one or more methods are provided that include detecting one or more nutraceutical associated components with one or more detection units and displaying results of the detecting with one or more display units that are operably coupled with the one or more detection units. In addition to the foregoing, other aspects are described in the claims, drawings, and text forming a part of the present disclosure.

In some embodiments one or more methods are provided that include detecting one or more nutraceutical associated components with one or more detection units, displaying results of the detecting with one or more display units that are operably coupled with the one or more detection units, and processing one or more samples with one or more microfluidic chips that are configured for analysis of the one or more nutraceutical associated components. In addition to the foregoing, other aspects are described in the claims, drawings, and text forming a part of the present disclosure.

In some embodiments one or more methods are provided that include processing one or more samples obtained from an individual with one or more microfluidic chips that are configured for analysis of one or more nutraceutical associated components, detecting the one or more nutraceutical associated components with one or more detection units, and displaying one or more dosages of one or more nutraceutical agents for supplementation of the individual in response to the detecting. In addition to the foregoing, other aspects are described in the claims, drawings, and text forming a part of the present disclosure.

In some embodiments one or more systems are provided that include one or more detection units configured to detachably connect to one or more microfluidic chips and configured to detect one or more nutraceutical associated components and one or more display units operably associated with the one or more detection units. In addition to the foregoing, other aspects are described in the claims, drawings, and text forming a part of the present disclosure.

In some embodiments one or more systems are provided that include one or more detection units configured to detachably connect to one or more microfluidic chips and configured to detect one or more nutraceutical associated components, one or more display units operably associated with the one or more detection units, and one or more microfluidic chips configured for analysis of the one or more nutraceutical associated components. In addition to the foregoing, other aspects are described in the claims, drawings, and text forming a part of the present disclosure.

In some embodiments one or more systems are provided that include one or more microfluidic chips configured for processing of a single nutraceutical associated component, one or more detection units configured to detachably connect to the one or more microfluidic chips and configured to detect one or more nutraceutical associated components that include the single nutraceutical associated component, and one or more display units operably associated with the one or more detection units that indicate one or more dosages of one or more nutraceutical agents for supplementation of an individual associated with the single nutraceutical associated component. In addition to the foregoing, other aspects are described in the claims, drawings, and text forming a part of the present disclosure.

In some embodiments, means include but are not limited to circuitry and/or programming for effecting the herein-referenced functional aspects; the circuitry and/or programming can be virtually any combination of hardware, software, and/or firmware configured to effect the herein-referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
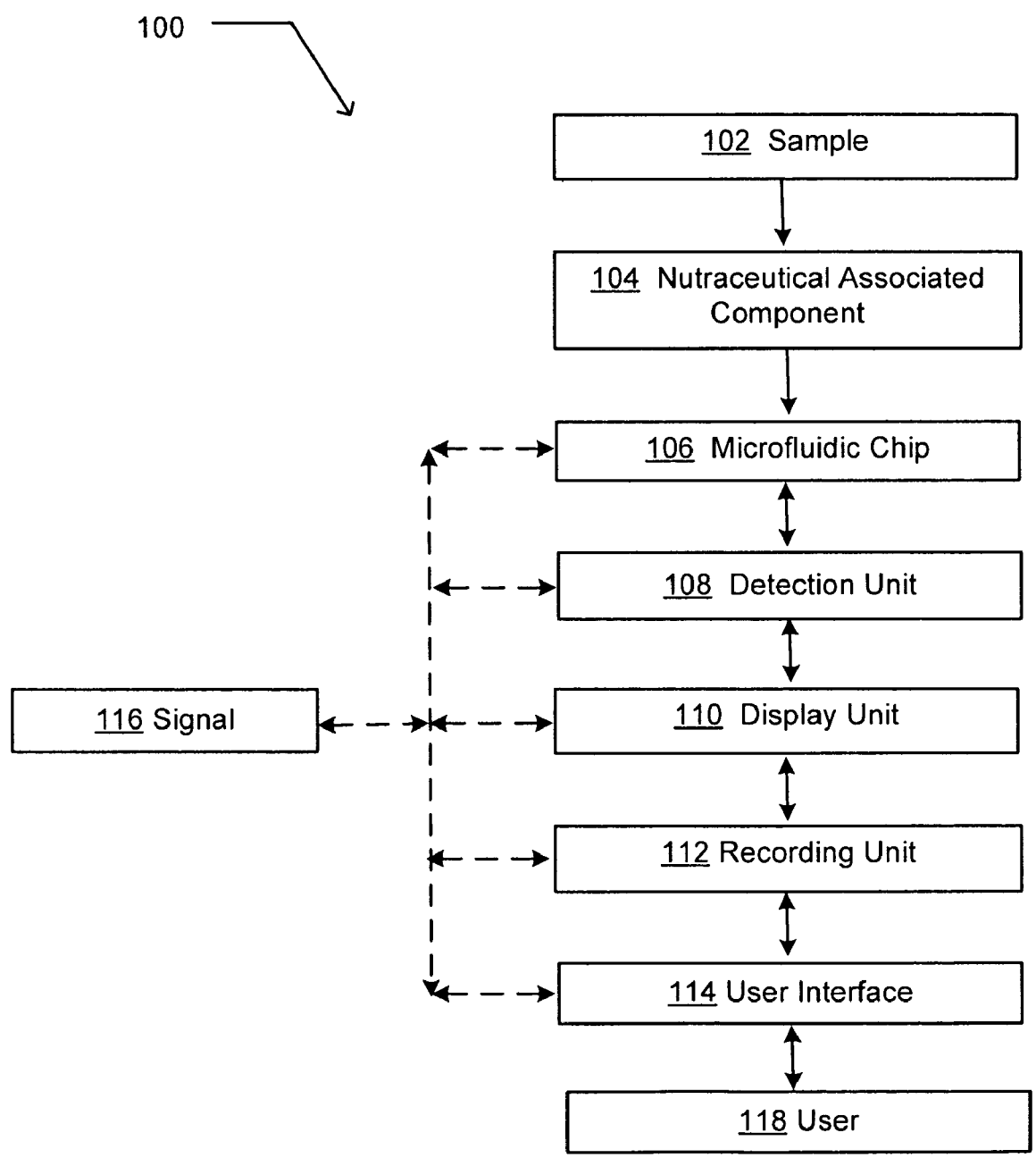
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a method that may be used to analyze one or more nutraceutical associated components 104. In some embodiments, one or more samples 102 may be processed with one or more microfluidic chips 106 that are configured to process one or more nutraceutical associated components 104. In some embodiments, one or more samples 102 associated with an individual may be processed. In some embodiments, one sample 102 associated with an individual may be processed. In some embodiments, one or more microfluidic chips 106 may be used to process one or more samples 102. In some embodiments, one microfluidic chip 106 may be used to process one or more samples 102. In some embodiments, one or more microfluidic chips 106 may be used to process one or more nutraceutical associated components 104. In some embodiments, one or more microfluidic chips 106 may be used to process one nutraceutical associated component 104. In some embodiments, one or more detection units may be used to detect one or more nutraceutical associated components 104. In some embodiments, one detection unit may be used to detect one or more nutraceutical associated components 104. In some embodiments, one or more detection units 108 may be portable detection units 108. In some embodiments, one or more detection units 108 may be non-portable detection units 108. In some embodiments, one or more detection units 108 may be hand-held detection units 108. In some embodiments, one or more detection units 108 may include one or more user interfaces 114. In some embodiments, one or more detection units 108 may include one user interface 114. In some embodiments, one or more detection units 108 may include one or more user interfaces 114 that are directly coupled with the one or more detection units 108. In some embodiments, one or more detection units 108 may include one or more user interfaces 114 that are remotely coupled with the one or more detection units 108. For example, in some embodiments, a user 118 may interact with the one or more detection units 108 through direct physical interaction with the one or more detection units 108. In other embodiments, a user 118 may interact with one or more detection units 108 through remote interaction. In some embodiments, one or more detection units 108 may transmit one or more signals 116. In some embodiments, one or more detection units 108 may include one or more display units 110. In some embodiments, one or more detection units 108 may be directly coupled to one or more display units 110. In some embodiments, one or more detection units 108 may be remotely coupled to one or more display units 110. In some embodiments, one or more detection units 108 may transmit one or more signals 116 that are received by one or more display units 110. In some embodiments, one or more display units 110 may include one or more user interfaces 114. In some embodiments, one or more display units 110 may include one user interface 114. In some embodiments, one or more display units 110 may transmit one or more signals 116. In some embodiments, system 100 may include one or more recording units 112. In some embodiments, one or more recording units 112 may be directly coupled to one or more detection units 108. In some embodiments, one or more recording units 112 may be directly coupled to one or more display units 110. In some embodiments, one or more recording units 112 may be directly coupled to one or more detection units 108 and one or more display units 110. In some embodiments, one or more recording units 112 may include one or more user interfaces 114. In some embodiments, one or more recording units 112 may include one or more directly coupled user interfaces 114. In some embodiments, one or more recording units 112 may include one or more remotely coupled user interfaces 114. In some embodiments, one or more recording units 112 may receive one or more signals 116. In some embodiments, one or more recording units 112 may transmit one or more signals 116.

Sample

Numerous types of samples 102 may be analyzed through use of system 100. In some embodiments, one or more samples 102 may be associated with an individual. In some embodiments, one or more samples 102 may include a liquid. In some embodiments, one or more samples 102 may include a solid. In some embodiments, one or more samples 102 may include a vapor. In some embodiments, one or more samples 102 may include a semi-solid. In some embodiments, one or more samples 102 may include a gas. Examples of such samples 102 include, but are not limited to, blood, urine, sweat, tears, excrement, saliva, skin, hair, mucus, or breath, or substantially any combination thereof.

Microfluidic Chip

Numerous types of microfluidic chips 106 may be utilized within system 100. For example, microfluidic chips 106 may be used that utilize a variety of methods to process one or more nutraceutical associated components 104. Examples of such methods include, but are not limited to, nucleic acid hybridization based methods, immunological based methods, chromatographic based methods, affinity based methods, extraction based methods, separation based methods, isolation based methods, filtration based methods, enzyme based methods, isoelectric focusing methods, and substantially any combination thereof.

Methods to construct microfluidic chips 106 have been described (i.e., U.S. Statutory Invention Registration No. H201; U.S. Pat. Nos. 6,454,945; 6,818,435; 6,812,458; 6,794,196; 6,709,869; 6,582,987; 6,482,306; Jain, *Pharmacogenomics,* 4:123-125 (2003); Jarvius, DNA Tools and Microfluidic Systems for Molecular Analysis, Digital Comprehensive Summaries of Uppsala Dissertations from the Faculty of Medicine 161, Uppsala Universitet, ACTA Universitatis Upsaliensis Uppsala (2006) ISSN 1651-6206/ISBN 91-554-6616-8; herein incorporated by reference). In some embodiments, one or more microfluidic chips 106 may include a lancet. Methods to construct lancets are known and have been described (U.S. Patent Application Nos.: 20020177763 and 20030083685; herein incorporated by reference). In some embodiments, one or more microfluidic chips may include carbon nanotubes. In some embodiments, one or more microfluidic chips may include carbon nanotubes that are configured to provide for transport. For example, in some embodiments, one or more carbon nanotubes may be configured to provide for transport of one or more gases and/or one or more fluids (Holt et al., Science, 312:1034-1037 (2006) and Sholl and Johnson, Science, 312:1003-100 (2006). In some embodiments, one or more microfluidic chips may include one or more carbon nanotubes that are operably coupled to nucleic acid. For example, in some embodiments, one or more carbon nanotubes may be used to immobilize nucleic acid. In some embodiments, one or more carbon nanotubes may be used to provide for detection of one or more nucleic acids (Heller et al., Science, 311:508-511 (2006) and Gao and Kong, Annu. Rev. Mater. Res., 34:123-150 (2004). In some embodiments, one or more microfluidic chips may include one or more carbon nanotubes to provide for separation of two or more components (Chen and Sholl, J. Membrane Science, 269:152-160 (2006). Numerous additional methods may be used to construct microfluidic chips 106 that may be used for analysis of one or more nutraceutical associated components 104.

Microfluidic chips 106 may utilize numerous methods for analysis of one or more nutraceutical associated components 104. For example, in some embodiments, one or more microfluidic chips 106 may utilize chemiluminescent methods (U.S. Pat. Nos. 6,090,545 and 5,093,268; herein incorporated by reference), plasmon resonance sensors (U.S. Pat. No. 7,030,989; herein incorporated by reference), nuclear magnetic resonance detectors (U.S. Pat. No. 6,194,900; herein incorporated by reference), gradient-based assays (U.S. Pat. No. 7,112,444; herein incorporated by reference), reporter beads (U.S. Pat. No. 5,747,349; herein incorporated by reference), transverse electrophoresis, isoelectric focusing, nucleic acid amplification, and/or diffusion based systems (U.S. Pat. Nos. 6,221,677; 5,972,710; deMello, Nature, 422:28-29 (2003) herein incorporated by reference).

Microfluidic chips 106 may be configured for analysis of numerous nutraceutical associated components 104. For example, in some embodiments, one or more microfluidic chips 106 may be configured for analysis of coenzyme Q10, reduced coenzyme Q10 (ubiquinol-10), and/or oxidized coenzyme Q10 (ubiquinone-10) in one or more samples 102 through use of described assay methods (i.e., U.S. Patent Application No.: 20040033553; herein incorporated by reference). In some embodiments, one or more microfluidic chips 106 may be configured for analysis of glucose (U.S. Pat. No. 6,295,506; herein incorporated by reference). In some embodiments, one or more microfluidic chips 106 may be configured for analysis of one or more polynucleotides (U.S. Pat. No. 6,958,216; herein incorporated by reference). Accordingly, microfluidic chips 106 may be configured for analysis of numerous nutraceutical associated components 104.

Nutraceutical Associated Component

System 100 may be used to analyze numerous types of nutraceutical associated components 104. Generally, a nutraceutical associated component 104 is a bodily component that is affected by the action, presence, absence, and/or deficiency of a nutraceutical agent. For example, the amount, activity, availability, and/or concentration of a nutraceutical associated component 104 may be increased or decreased in a manner that is dependent upon the presence or absence of one or more nutraceutical agents. Nutraceutical associated components 104 may also include one or more components that are indicative of a need for supplementation and/or reduction. For example, in some embodiments, a nutraceutical associated component 104 may be an enzyme and/or an enzyme activity where high or low levels of the enzyme and/or enzyme activity indicate a need for supplementation or reduction in the level of one or more nutraceutical agents (i.e., the activity of an enzyme that produces a stress hormone may indicate a need for supplementation with a stress-reducing vitamin). Numerous types of nutraceutical associated components 104 may be analyzed through use of system 100. Examples of such nutraceutical associated components 104 include, but are not limited to, enzymes, hormone, prohormone, hemoglobin, polynucleotide, proteins, peptides, antioxidant, minerals, vitamins, and substantially any combination thereof. In some embodiments, a nutraceutical associated component 104 includes a nutraceutical agent.

Nutraceutical agents typically include natural, bioactive chemical compounds, vitamins, minerals, or any substance that is a plant, food, an extracted part of a food, that provides medical or health benefits but which generally fall outside regulations controlling pharmaceuticals. In some embodiments, nutraceutical agents may include substances that are regulated as pharmaceuticals when they are formulated in certain regulated combinations and/or quantities but that are not regulated as pharmaceuticals when formulated in combinations and/or quantities that are not regulated. Included in this category of substances may be foods, isolated nutrients, supplements and herbs. Nutraceuticals are often referred to as phytochemicals or functional foods and include dietary supplements. Numerous nutraceuticals have been described (i.e., Roberts et al., Nutraceuticals: The Complete Encyclopedia of Supplements, Herbs, Vitamins, and Healing Foods, 1$^{st}$ Edition, Perigee Trade (2001) and Susan G. Wynn, Emerging Therapies: Using Herbs and Nutraceuticals for Small Animals, American Animal Hospital Assn Press (1999); and Handbook of Nutraceuticals and Functional Foods., edited by Robert E. C. Wildman, CRC Press (2001)). Examples of nutraceutical agents include, but are not limited to, Amino Acids, Terpenoids, Carotenoid Terpenoids (Lycopene, Beta-Carotene, Alpha-Carotene, Lutein, Zeaxanthin, Astaxanthin), Herbal Supplements, Homeopathic Supplements, Glandular Supplements, Non-Carotenoid Terpeniods (Perillyl Alcohol, Saponins, Terpeneol, Terpene Limonoids), Polyphenolics, Flavonoid Polyphenolics (Anthocyanins, Catechins, Isoflavones, Hesperetin, Naringin, Rutin, Quercetin, Silymarin, Tangeretin, Tannins), Phenolic Acids (Ellagic Acid, Chlorogenic Acid, Para-Coumaric Acid, Phytic Acid, Cinnamic Acid), Other Non-Flavonoid Polyphenolics (Curcumin, Resveratrol, Lignans), Glucosinolates, Isothiocyanates (Phenethyl Isothiocyanate, Benzyl Isothiocyanate, Sulforaphane), Indoles (Indole-3-Carbinol (I3C), Thiosulfonates, Phytosterols (Beta-Sitosterol), Anthraquinones (Senna, Barbaloin, Hypericin), Capsaicin, Piperine, Chlorophyll, Betaine, Pectin, Oxalic Acid, Acetyl-L-Carnitine, Allantoin, Androsterondiol, Androsterondione, Betaine (Trimethylglycine), Caffeine, Calcium pyvurate (Pyruvic Acid), Carnitine, Carnosine, Carotene (alpha & beta), Carotenoid (Total for beadlets), Choline, Chlorogenic Acid, Cholic Acid (Ox Bile), Chondroitin Sulfate, Chondroitin Sulfate (Total Mucopolysaccharides), Cholestin, Chrysin, Coenzyme Q10 (Co-Q10), Conjugated Linoleic Acid (CLA), Corosolic Acid, Creatine, Dehydroepiandrosterone (DHEA), Dichlorophen, Diindolymethane (DIM), Dimethyglycine (DMG), Dimercapto Succinic Acid (DMSA), Ebselen, Ellagic Acid, Enzymes, Fisetin, Formonetin, Glucaric Acid (Glucarate), Glucosamine (HCl or Sulfate), Glucosamine (N-Acetyl), Glutathione (Reduced), Hesperidine, Hydroxy-3-Methylbutyric Acid (HMB), 5-Hydroxytryptophan (L-5-HTP), Indole-3-Carbinol, Inositol, Isothiocyanates, Linolenic Acid-Gamma (GLA), Lipoic Acid (alpha), Melatonin, Methylsulfonylmethane (MSM), Minerals, Naringin, Pancreatin, Para-aminobenzoic Acid (PABA), Paraben (methyl or propyl), Phenolics, Phosphatidylcholine (Lecithin), Phosphatidylserine, Phospholipids, Phytosterols, Pregersterone, Pregnenolone, Quercetin, Resveratrol, D-Ribose, Rutin, S-adenosylmethionine (SAM-e), Salicylic Acid, Sulforaphane, Tartaric Acid, Taxifolin, Tetrahydropalmatine, Thephyline, Theobromine, Tigogenin, Troxerutin, Tryptophan, Tocotrienol (alph, beta & gamma), Vitamins, Zeaxanthin, Gingo Biloba, Ginger, Cat's Claw, *Hypericum*, Aloe Vera, Evening Primrose, Garlic, *Capsicum*, Dong Quai, Ginseng, Feverview, Fenugreek, Echinacea, Green Tea, Marshmallow, Saw Palmetto, Tea Tree Oil, Payllium, Kava-Kava, Licorice Root, Manonia Aquifolium, Hawthorne, Hohimbr, Tumeric, Witch Hazel, Valerian, Mistletoe, Bilberry, Bee Pollen, Peppermint Oil, Beta-Carotene, Genistein, Lutein, Lycopene, the Polyphenols (bioflavonoids), and the like.

Nutraceutical agents may also include microbes (i.e., probiotics). Examples of such microbes include, but are not limited to, *Lactobacillus acidophilus, Lactobacillus plantarum, Lactobacillus casei, Bifidobacterium bifidum, Bifidobacterium longum, Saccharomyces boulardii, Saccharomyces cerevisiae*, and the like (i.e., Samuel and Gordon, A humanized gnotobiotic mouse model of host-archaeal-bacterial mutualism, PNAS, 103(26):10011-10016 (2006)). In some embodiments, nutraceutical agents may include non-living microbes. For example, non-living *Saccharomyces cerevisiae* may be used as a source of vitamin B12. In some embodiments, recombinant microbes may be nutraceutical agents. For example, in some embodiments, microbes may be genetically modified to produce, or overexpress, one or more nutraceutical agents.

Detection Unit

Numerous types of detection units 108 may be used within system 100. Accordingly, numerous types of detection methods may be used within system 100. Examples of such detection methods include, but are not limited to, colorimetric methods, spectroscopic methods, resonance based methods, or substantially any combination thereof. In some embodiments, a detection unit 108 may be stationary. For example, in some embodiments, a detection unit 108 may be a laboratory instrument. In some embodiments, a detection unit 108 may be portable. For example, in some embodiments, a detection unit 108 may be a hand-held device.

User Interface/User

Numerous types of users 118 may interact with system 100. In some embodiments, a user 118 may be human. In some embodiments, a user 118 may be non-human. In some embodiments, a user 118 may interact with one or more detection units 108, one or more display units 110, one or more user interfaces 114, one or more recording units 112, and/or substantially any combination thereof. The user 118 can interact through use of numerous types of user interfaces 114. For example, one or more users 118 may interact through use of numerous interfaces that utilize hardwired methods, such as through use of a keyboard, use of wireless methods, use of the internet, and the like. In some embodiments, a user 118 may be a health-care worker. Examples of such health-care workers include, but are not limited to, physicians, nurses, dieticians, pharmacists, and the like. In some embodiments, users 118 may include those persons who work in health-related fields, such as coaches, personal trainers, clerks at food supplement stores, clerks at grocery stores, and the like.

Signal

The system 100 may include one or more signals 116. Numerous types of signals 116 may be transmitted. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Display Unit

The system 100 may include one or more display units 110. Numerous types of display units 110 may be used in association with system 100. Examples of such display units 110 include, but are not limited to, liquid crystal displays, printers, audible displays, cathode ray displays, plasma display panels, Braille displays, and the like. In some embodiments, display units 110 may display information in numerous languages. Examples of such languages include, but are not limited to, English, Spanish, German, Japanese, Chinese, Italian, and the like.

In some embodiments, one or more display units 110 may be physically coupled to one or more detection units 108. In some embodiments, one or more display units 110 may be remotely coupled to one or more detection units 108. For example, in some embodiments, one or more display units 110 may receive one or more signals 116 from one or more detection units 108 that are remotely positioned relative to the detection units 108. Accordingly, one or more display units 110 may be positioned in one or more locations that are remote from the position where analysis of one or more nutraceutical associated components 104 takes place. Examples of such remote locations include, but are not limited to, the offices of physicians, nurses, dieticians, pharmacists, coaches, personal trainers, clerks at food supplement stores, clerks at grocery stores, and the like.

Recording Unit

The system 100 may include one or more recording units 112. In some embodiments, one or more recording units 112 can communicate with one or more detection units 108, one or more display units 110, one or more user interfaces 114, and/or substantially any combination thereof. Many types of recording units 112 may be used within system 100. Examples of such recording devices include those that utilize a recordable medium that includes, but is not limited to, many types of memory, optical disks, magnetic disks, magnetic tape, and the like.

In some embodiments, one or more recording units 112 may be physically coupled to one or more detection units 108. In some embodiments, one or more recording units 112 may be physically coupled to one or more display units 110. In some embodiments, one or more recording units 112 may be remotely coupled to one or more detection units 108 and/or one or more display units 110. For example, in some embodiments, one or more recording units 112 may receive one or more signals 116 from one or more detection units 108 and/or one or more display units 110 that are remotely positioned relative to the one or more recording units 112. Accordingly, one or more recording units 112 may be positioned in one or more locations that are remote from the position where analysis of one or more nutraceutical associated components 104 takes place. Examples of such remote locations include, but are not limited to, the offices of physicians, nurses, dieticians, pharmacists, coaches, personal trainers, clerks at food supplement stores, clerks at grocery stores, and the like.

Dosage

Dosages may be expressed in numerous ways. In some embodiments, a dosage may be expressed as an absolute quantity (i.e., 500 milligrams of a nutraceutical agent). In other embodiments, a dosage may be expressed in accordance with the body weight of an individual (i.e., 10 milligram nutraceutical agent per kilogram body weight). In some embodiments, a dosage may be expressed as a range of quantities (i.e., 10 milligrams to 100 milligrams of a nutraceutical agent). In some embodiments, a dosage may be an amount of a nutraceutical agent that produces a desired response when administered to a specific individual. For example, a dosage of melatonin may be the amount of melatonin that induces sleep in a specific individual. The dosage of a nutraceutical agent may vary according to numerous considerations that include, but are not limited to, the route of administration, the age of the individual, the size of the individual, the metabolic characteristics of the individual, the condition of the individual, and the like. In some embodiments, the dosage of a nutraceutical agent may be determined that produces a measurable effect, such as a physical effect, a psychological effect, a physiological effect, and the like. Accordingly, in some embodiments, a dosage may be expressed as an amount of a nutraceutical agent that produces a mental response in an individual. For example, in some embodiments, a dosage may be the amount of a nutraceutical agent that produces a sensation of well-being when administered to an individual. In other embodiments, a dosage may be the amount of a nutraceutical agent that elevates the mood of an individual to whom the nutraceutical is to be administered. Numerous additional criteria may be used to determine the dosage of a nutraceutical for administration to an individual.

In some embodiments, one or more display units 110 can indicate one or more dosages of one or more nutraceutical agents and one or more formulations of the one or more nutraceutical agents. For example, in some embodiments, one or more display units 110 may indicate a formulation and dosage of chromium. Presently, the most widely available chromium supplements are chromium salts such as chromium polynicotinate, chromium picolinate, and various chromium/amino acid chelates. Such formulations help increase the absorption and availability of chromium when compared to isolated chromium salts such as chromium chloride. The estimated safe and adequate daily dietary intake of chromium is 50-200 micrograms. Natural forms of supplemental chromium, such as chromium-rich yeast, may be absorbed somewhat more efficiently than inorganic forms of chromium, such as chromium chloride, found in some supplements. One ounce of brewer's yeast provides approximately 100-200 micrograms of chromium. Accordingly, in some embodiments, one or more display units 110 may indicate a dosage of chromium and a corresponding formulation of the chromium. In another embodiment, one or more display units 110 may indicate a dosage of vitamin A. For vitamin A deficiency syndromes, vitamin A may be orally supplemented at a dosage 122 of 600 micrograms for children aged 3 years or younger, 900 micrograms for children aged 4-8 years, 1700 micrograms for children aged 9-13 years, 2800 micrograms for persons aged 14-18 years, and 3000 micrograms for all adults. Therapeutic doses for severe diseases include 60,000 micrograms, which has been shown to reduce child mortality rates by 35-70%. One or more display units 110 may indicate dosages for numerous types of nutraceutical agents that may be formulated in numerous ways.

Figure 2:
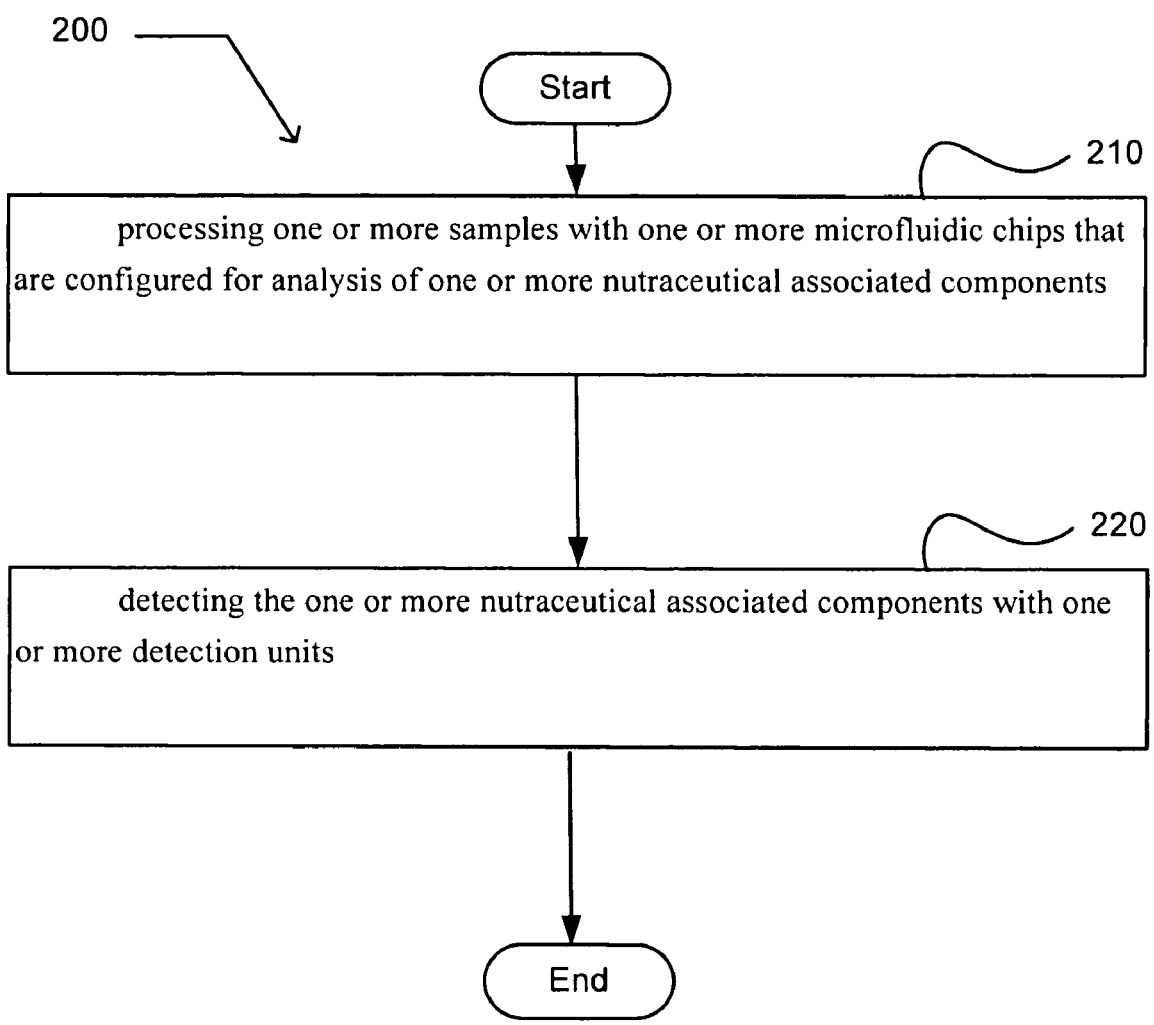
FIG. 2 illustrates an operational flow representing example operations related to methods and systems for analysis of nutraceutical associated components.

FIG. 2 illustrates an operational flow 200 representing examples of operations that are related to the performance of a method for analysis of one or more nutraceutical associated components 104. In FIG. 2 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes a processing operation 210 involving processing one or more samples with one or more microfluidic chips that are configured for analysis of one or more nutraceutical associated components. In some embodiments, one or more microfluidic chips 106 that are configured for analysis of one or more nutraceutical associated components 104 may be used to process one or more samples 102. In some embodiments, one or more microfluidic chips 106 may accept one or more samples 102. In some embodiments, one or more microfluidic chips 106 may accept one or more samples 102 acquired through use of one or more non-invasive techniques. In some embodiments, one or more microfluidic chips 106 may accept one or more samples 102 that include at least one of sweat, tears, urine, breath, skin, hair, saliva, excrement, mucus, or substantially any combination thereof. In some embodiments, one or more microfluidic chips 106 may accept one or more samples 102 that include blood. In some embodiments, one or more microfluidic chips 106 may be used to process one or more samples 102 utilizing polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, one or more microfluidic chips 106 may be used to process one or more samples 102 that include at least one of sweat, tears, urine, breath, skin, hair, saliva, excrement, blood, mucus, or substantially any combination thereof. In some embodiments, one or more microfluidic chips 106 may be used to process one or more samples 102 that include at least one hormone, prohormone, polynucleotide, enzyme, protein, vitamin, mineral, metal, antioxidant, a substantially any combination thereof. In some embodiments, one or more microfluidic chips 106 may be used to process two or more samples 102 that are collected at two or more different times. In some embodiments, one or more microfluidic chips 106 may be used to process one or more samples 102 that are configured for analysis of a single nutraceutical associated component 104. In some embodiments, one or more microfluidic chips 106 may provide for user interaction.

The operational flow 200 includes a detecting operation 220 involving detecting the one or more nutraceutical associated components with one or more detection units. In some embodiments, one or more detection units 108 may be used to detect one or more nutraceutical associated components 104. In some embodiments, one or more detection units 108 may be used to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be used to detect one or more nutraceutical associated components 104 that are associated with two or more samples 102 that were collected at two or more different times. In some embodiments, one or more detection units 108 may provide for user interaction. In some embodiments, one or more detection units 108 may be used to transmit one or more signals 116 to one or more display units 110. In some embodiments, one or more detection units 108 may be used to transmit one or more signals 116 to one or more recording units 112.

Figure 3:
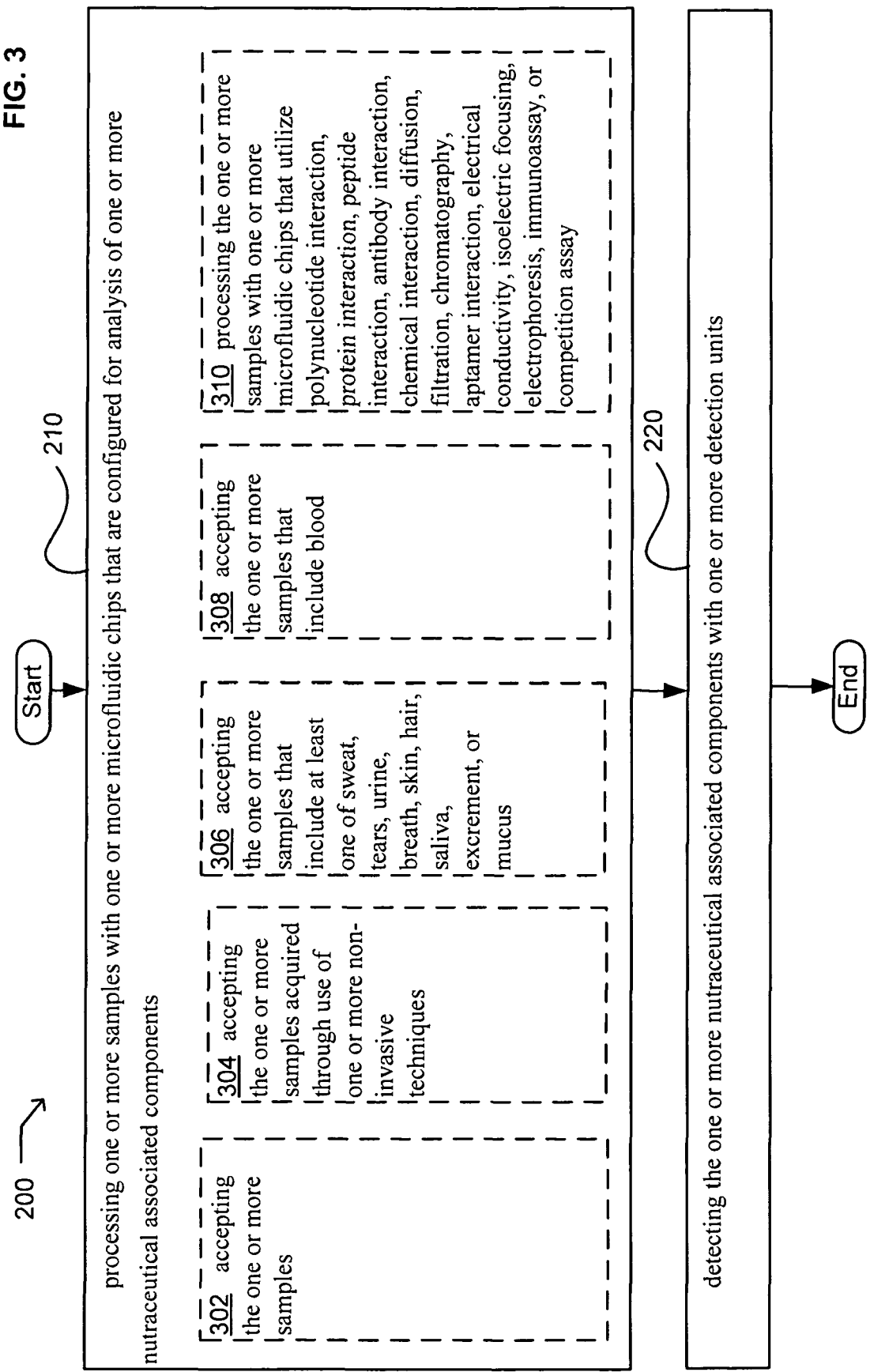
FIG. 3 illustrates alternate embodiments of the example operational flow of FIG. 2.

FIG. 3 illustrates alternative embodiments of the example operational flow 200 of FIG. 2. FIG. 3 illustrates example embodiments where the processing operation 210 may include at least one additional operation. Additional operations may include an operation 302, an operation 304, an operation 306, an operation 308, and/or an operation 310.

At operation 302, the processing operation 210 may include accepting the one or more samples. In some embodiments, one or more microfluidic chips 106 may be configured to accept one or more samples 102. For example, in some embodiments, a microfluidic chip 106 may include a needle to accept one or more blood and/or tissue samples 102. In some embodiments, a microfluidic chip 106 may include a mouthpiece to accept one or more breath and/or saliva samples 102. In some embodiments, a microfluidic chip 106 may include a scraper to accept one or more skin and/or tissue samples 102. Accordingly, in some embodiments, one or more microfluidic chips 106 may accept one or more samples 102. In some embodiments, one or more microfluidic chips 106 may accept one or more samples 102 that are collected through use of invasive techniques. Such techniques include, but are not limited to, drawing blood, obtaining mucus, obtaining tissue samples 102, and the like. In some embodiments, one or more microfluidic chips 106 may accept one or more samples 102 that are collected through use of non-invasive techniques. Such techniques include, but are not limited to, collecting one or more samples 102 that include breath, saliva, hair, sweat, tears, and the like.

In some embodiments, individuals may collect one or more samples 102 from themselves. Accordingly, in some embodiments, system 100 may be used for point-of-care analysis by an individual. In some embodiments, one or more samples 102 may be processed by someone other than the individual from whom the one or more samples 102 were collected. For example, in some embodiments, individuals may collect one or more samples 102 from themselves and then send the one or more samples 102 for analysis by a person other than the individual from whom the samples 102 were collected. In other embodiments, one or more samples 102 may be collected from an individual and analyzed by a person other than the individual. For example, a physician, nurse, coach, nutritionist, personal trainer, or the like may collect one or more samples 102 from an individual and then analyze the one or more samples 102 through use of system 100.

At operation 304, the processing operation 210 may include accepting the one or more samples acquired through use of one or more non-invasive techniques. In some embodiments, one or more microfluidic chips 106 may be configured to accept one or more samples 102 that were collected through use of non-invasive techniques. Such techniques include, but are not limited to, collecting one or more samples 102 from an individual that include breath, saliva, hair, sweat, tears, excrement, and the like. For example, in some embodiments, a microfluidic chip 106 may include a mouthpiece to accept breath and/or saliva samples 102. In some embodiments, a microfluidic chip 106 may include a capillary tube to accept fluid samples 102, such as sweat, tears, urine, saliva, and the like. In some embodiments, individuals may collect one or more samples 102 from themselves. Accordingly, in some embodiments, system 100 may be used for point-of-care analysis by an individual. In some embodiments, one or more samples 102 may be analyzed by someone other than the individual from whom the one or more samples 102 were collected. For example, in some embodiments, individuals may collect one or more samples 102 from themselves and then send the one or more samples 102 for analysis by a person other than the individual from whom the samples 102 were collected. In other embodiments, one or more samples 102 may be collected from an individual and analyzed by a person other than the individual. For example, a physician, nurse, coach, nutritionist, personal trainer, or the like may collect one or more samples 102 from an individual and then analyze the one or more samples 102 through use of system 100.

At operation 306, the processing operation 210 may include accepting the one or more samples that include at least one of sweat, tears, urine, breath, skin, hair, saliva, excrement, or mucus. In some embodiments, one or more microfluidic chips 106 may accept one or more samples 102 that include at least one of sweat, tears, urine, breath, skin, hair, saliva, excrement, or mucus. In some embodiments, individuals may collect one or more samples 102 from themselves. Accordingly, in some embodiments, system 100 may be used for point-of-care analysis by an individual. In some embodiments, one or more samples 102 may be analyzed by someone other than the individual from whom the one or more samples 102 were collected. For example, in some embodiments, individuals may collect one or more samples 102 from themselves and then send the one or more samples 102 for analysis by a person other than the individual from whom the samples 102 were collected. In other embodiments, one or more samples 102 may be collected from an individual and analyzed by a person other than the individual. For example, a physician, nurse, coach, nutritionist, personal trainer, or the like may collect one or more samples 102 from an individual and then analyze the one or more samples 102 through use of system 100.

At operation 308, the processing operation 210 may include accepting the one or more samples that include blood. In some embodiments, one or more microfluidic chips 106 may be configured to accept one or more blood samples 102. For example, in some embodiments, a microfluidic chip 106 may include a needle that may be used to penetrate tissue to accept a blood sample 102. In some embodiments, a microfluidic chip 106 may include a capillary tube that may be used to accept blood for analysis. Such a capillary tube may be used to accept blood for analysis without having to pierce the skin or other tissue of an individual. For example, such a capillary tube may be used to accept a blood sample 102 for analysis by inserting the capillary tube into a blood sample 102 resulting from a finger stick with a lancet.

In some embodiments, individuals may collect one or more blood samples 102 from themselves. Accordingly, in some embodiments, system 100 may be used for point-of-care analysis by an individual. In some embodiments, one or more blood samples 102 may be processed by someone other than the individual from whom the one or more samples 102 were collected. For example, in some embodiments, individuals may collect one or more blood samples 102 from themselves and then send the one or more blood samples 102 for processing by a person other than the individual from whom the samples 102 were collected. In other embodiments, one or more blood samples 102 may be collected from an individual and analyzed by a person other than the individual. For example, a physician, nurse, coach, nutritionist, personal trainer, or the like may collect one or more blood samples 102 from an individual and then analyze the one or more blood samples 102 through use of system 100.

At operation 310, the processing operation 210 may include processing the one or more samples with one or more microfluidic chips that utilize polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, one or more microfluidic chips 106 may process one or more samples 102 with at least one technique that includes processing the one or more samples 102 with one or more microfluidic chips 106 that utilize polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof.

In some embodiments, one or more microfluidic chips 106 may process one or more samples 102 utilizing polynucleotide interaction (Singh-Zocchi et al., Proc. Natl. Acad. Sci., 100:7605-7610 (2003) and Wang et al., Anal. Chem., 75:3941-3945 (2003)). Such polynucleotide interaction may occur through hybridization of deoxyribonucleic acid, ribonucleic acid, derivatives thereof, or substantially any combination thereof. In some embodiments, polynucleotides may be configured as polynucleotide arrays. Methods to construct polynucleotide arrays are known and have been used to construct various polynucleotide arrays (Affymetrix, Santa Clara, Calif.).

In some embodiments, one or more microfluidic chips 106 may be configured to process one or more samples 102 through use of competition assays. In some embodiments, a competition assay may utilize a reaction mixture that may include a first fluorescently labeled component that binds to a second fluorescently labeled component. The presence of one or more unlabeled nutraceutical associated components 104 in the reaction mixture decreases the amount of labeled first component and labeled second component that bind to each other and thereby reduces fluorescence resonance energy transfer. Accordingly, detecting the level of fluorescence resonance energy transfer by a detection unit 108 allows the amount of a nutraceutical associated component 104 in a sample 102 to be determined. Numerous other configurations may be prepared that utilize fluorescence resonance energy transfer by one or more detection units 108. In some embodiments, fluorescence quenching may be used within a competition assay. In some embodiments, one or more microfluidic chips 106 may be configured for competition assays where a sample 102 being tested for one or more nutraceutical associated components 104 is mixed with a reaction mixture that includes one or more labeled components that are being tested. The mixed reaction mixture is then passed over a field and/or array to which moieties that bind to the one or more nutraceutical associated components 104 and labeled components are immobilized. The one or more unlabeled nutraceutical associated components 104 in the sample 102 will compete with the one or more labeled components in the reaction mixture for binding and will thereby decrease the amount of label bound within the field and/or array. Accordingly, the amount of one or more nutraceutical associated components 104 being tested for in the sample 102 may be indicated by a decrease in bound label. In some embodiments, such microfluidic chips 106 may include a control field and/or array. In some embodiments, such microfluidic chips 106 may be calibrated prior to application of the sample 102 and therefore not include a control field and/or array. In some embodiments, such fields and/or arrays may include polynucleotides, proteins, peptides, nucleic acid aptamers, peptide aptamers, antibodies, chemicals, chromatographic media, and other materials that may be used to separate one or more nutraceutical associated components 104 from one or more samples 102. Accordingly, fields and/or arrays may include numerous types of moieties that may be used to detect numerous types of nutraceutical associated components 104. In some embodiments, a microfluidic chip 106 may be configured to process one or more samples 102 for one type of nutraceutical associated component 104. In some embodiments, a microfluidic chip 106 may be configured to process one or more samples 102 for one or more types of nutraceutical associated components 104.

In some embodiments, one or more microfluidic chips 106 may be configured to process one or more samples 102 through use of protein interaction. In some embodiments, such interaction may occur through binding interaction. In some embodiments, such interaction may include enzymatic activity. For example, a microfluidic chip 106 may include one or more enzymes that catalyze a reaction that includes nutraceutical associated components 104 as a substrate or as a product. In some embodiments, a nutraceutical associated component 104 may be assayed based on the ability to stimulate an enzyme. In some embodiments, a nutraceutical associated component 104 may be assayed based on the ability to inhibit an enzyme. In some embodiments, such enzyme assays may be calorimetric assays. Accordingly, numerous types of enzyme assays may be adapted for detection of one or more nutraceutical associated components 104.

One or more microfluidic chips 106 may be configured to utilize electrical conductivity to assay one or more nutraceutical associated components 104. Briefly, in some embodiments, one or more microfluidic chips 106 may include electrodes that may be directly coupled to a processor so that the processor may determine the electrical conductivity between electrodes of a particular sensor (U.S. Pat. Nos. 6,958,216 and 7,022,288; herein incorporated by reference).

In some embodiments, one or more microfluidic chips 106 may be configured to utilize isoelectric focusing to process one or more nutraceutical associated components 104 (i.e., U.S. Pat. Nos. 7,074,583; 7,046,357; 6,852,206; 6,849,396; and 7,074,311; herein incorporated by reference). Briefly, isoelectric focusing may be used to characterize nutraceutical associated components 104, such as proteins, based on differences in their isoelectric points. The nutraceutical associated components 104 may then be separated according to their position within a pH gradient.

Numerous chromatographic methods may be used to process one or more nutraceutical associated components 104.

Examples of such chromatographic methods include, but are not limited to, gel filtration chromatography, ion-exchange chromatography, affinity chromatography, and the like.

In some embodiments, one or more microfluidic chips 106 may be configured to utilize filtration to process one or more nutraceutical associated components 104. For example, one or more nutraceutical associated components 104 may be processed based on their ability and/or inability to pass through a filter. Such filters may separate nutraceutical associated components 104 based on numerous properties. Examples of such properties include, but are not limited to, molecular weight, charge, hydrophobicity, hydrophilicity, and the like. In some embodiments, one or more microfluidic chips 106 may be configured to use an H-filter to separate one or more nutraceutical associated components 104. Such H-filters have been described (U.S. Pat. Nos. 6,221,677; 6,695,147; 6,541,213; herein incorporated by reference).

In some embodiments, one or more microfluidic chips 106 may be configured to utilize electrophoresis to process one or more nutraceutical associated components 104. Such methods are known in the art (Molecular Cloning: A Laboratory Manual, Cold Spring Harbor Laboratory Press; 3rd edition (Jan. 15, 2001)).

In some embodiments, one or more microfluidic chips 106 may be configured to utilize immunoassay to process one or more nutraceutical associated components 104. Such methods are known in the art (Molecular Cloning: A Laboratory Manual, Cold Spring Harbor Laboratory Press; 3rd edition (Jan. 15, 2001)). Combinations of numerous methods may be used to process one or more nutraceutical associated components 104.

Figure 4:
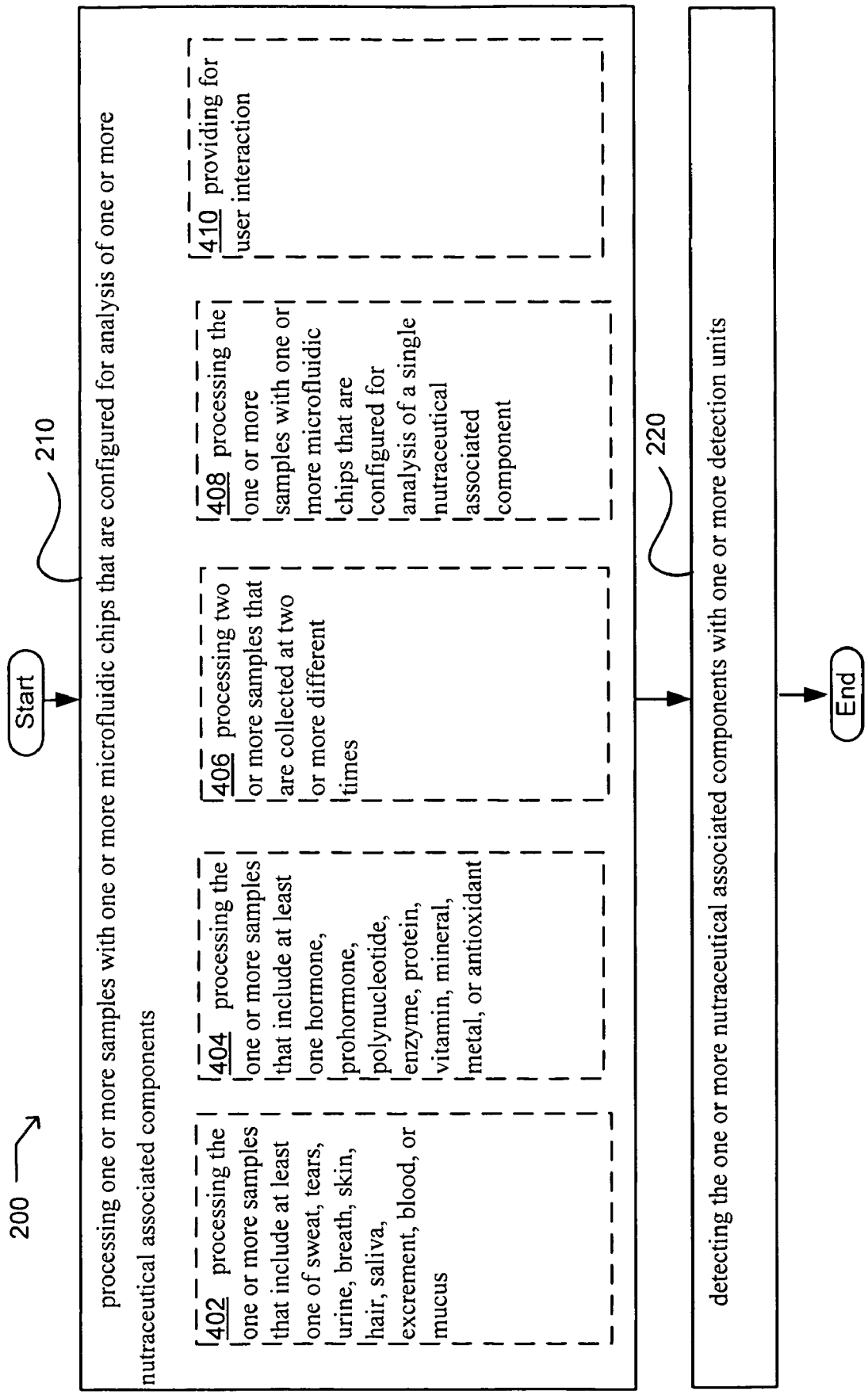
FIG. 4 illustrates alternate embodiments of the example operational flow of FIG. 2.

FIG. 4 illustrates alternative embodiments of the example operational flow 200 of FIG. 2. FIG. 4 illustrates example embodiments where the processing operation 210 may include at least one additional operation. Additional operations may include an operation 402, an operation 404, an operation 406, an operation 408, and/or an operation 410.

At operation 402, the processing operation 210 may include processing the one or more samples that include at least one of sweat, tears, urine, breath, skin, hair, saliva, excrement, blood, or mucus. One or more microfluidic chips 106 may be used to process one or more samples 102 that include at least one of sweat, tears, urine, breath, skin, hair, saliva, excrement, blood, mucus, or substantially any combination thereof. In some embodiments, one or more samples 102 may be processed through use of extraction methods to provide for detection of one or more nutraceutical associated components 104. For example, in some embodiments, nucleic acid may be extracted from a sample 102. In other embodiments, one or more enzymes may be extracted from one or more samples 102. In some embodiments, one or more nutraceutical associated components 104 may be solvent extracted from one or more samples 102. Numerous methods may be used to process one or more samples 102.

At operation 404, the processing operation 210 may include processing the one or more samples that include at least one hormone, prohormone, polynucleotide, enzyme, protein, vitamin, mineral, metal, or antioxidant. In some embodiments, one or more microfluidic chips 106 may be used to process one or more samples 102 that include at least one hormone, prohormone, polynucleotide, enzyme, protein, vitamin, mineral, metal, antioxidant, or substantially any combination thereof.

Examples of hormones that may be processed through use of one or more microfluidic chips 106 include, but are not limited to, testosterone (free and/or bound), estrogen, androgens, estradiol, progesterone, melatonin, serotonin, follicle stimulating hormone, dehydroepiandrosterone (DHEA), 5-HTP, cortisol, thyroid stimulating hormone, human chorionic gonadotropin, prohormones thereof, or substantially any combination thereof.

Examples of polynucleotides that may be processed through use of one or more microfluidic chips 106 include, but are not limited to, those that encode hormones, enzymes involved in oxidative pathways, enzymes involved in metabolic pathways, and the like.

Examples of enzymes that may be processed through use of one or more microfluidic chips 106 include, but are not limited to, enzymes involved in oxidative pathways, enzymes involved in metabolic pathways, or substantially any combination thereof.

Examples of proteins that may be processed through use of one or more microfluidic chips 106 include, but are not limited to, proteins linked to urinary tract infection, prostate specific antigen, microalbumin, hemoglobin, or substantially any combination thereof.

Examples of vitamins that may be processed through use of one or more microfluidic chips 106 include, but are not limited to, vitamin A, B vitamins, C vitamins, vitamin D, E vitamins, vitamin K, or substantially any combination thereof.

Examples of minerals that may be processed through use of one or more microfluidic chips 106 include, but are not limited to, calcium, chromium, cobalt, copper, iodine, magnesium, manganese, selenium, strontium, sulfur, zinc, or substantially any combination thereof.

Examples of metals that may be processed through use of one or more microfluidic chips 106 include, but are not limited to, aluminum, antimony, arsenic, bismuth, cadmium, lead, mercury, nickel, tin, or substantially any combination thereof.

Examples of antioxidants that may be processed through use of one or more microfluidic chips 106 include, but are not limited to, vitamin A, vitamin C, vitamin E, alpha lipoic acid, coenzyme Q-10, or substantially any combination thereof.

At operation 406, the processing operation 210 may include processing two or more samples that are collected at two or more different times. In some embodiments, one or more microfluidic chips 106 may be used to process two or more samples 102 that are collected at two or more different times. For example, a first sample 102 may be processed that was collected at a first time and a second sample 102 may be processed that was collected at a second time. Numerous samples 102 and time points may be processed through use of microfluidic chips 106. Accordingly, in some embodiments, the presence or absence of one or more nutraceutical associated components 104 at two or more times may be determined. In some embodiments, an increase or decrease in a nutraceutical associated component 104 in a time relevant manner may be determined. Such an increase or decrease in a nutraceutical associated component 104 may be determined through detection of concentration, activity, and the like. Accordingly, system 100 may be used to determine dosages of one or more nutraceutical agents for administration to an individual or group of individuals. In some embodiments, system 100 may be used to determine one or more metabolic responses to one or more nutraceutical agents by an individual or group of individuals.

At operation 408, the processing operation 210 may include processing the one or more samples with one or more microfluidic chips that are configured for analysis of a single nutraceutical associated component. In some embodiments, a microfluidic chip 106 may be configured for analysis of a single nutraceutical associated component 104. For example, in some embodiments, a microfluidic chip 106 may be configured for analysis of testosterone in at least one sample 102. In some embodiments, such a microfluidic chip 106 may be configured for analysis of free versus bound testosterone. In some embodiments, a microfluidic chip 106 may be configured for analysis of estrogen in at least one sample 102. Accordingly, microfluidic chips 106 may be configured for analysis of numerous types of nutraceutical associated components 104.

At operation 410, the processing operation 210 may include providing for user interaction. In some embodiments, a microfluidic chip 106 may provide for user interaction. For example, in some embodiments, a microfluidic chip 106 may include a receiver that receives signals 116 that are transmitted in response to a user interface 114. Such signals 116 may direct the microfluidic chip 106 to act in accordance with commands input by a user 118. In some embodiments, a microfluidic chip 106 may include one or more user interfaces 114 that provide for direct interaction with a user 118. Examples of such user interfaces 114 include, but are not limited to, ports for accepting samples 102, ports for accepting reagents, electrical connections, couplings, and the like. In some embodiments, electrical connections may be configured for accepting various devices that may be used for numerous purposes, such as to control or monitor a microfluidic chip 106. In some embodiments, couplings may be configured for attachment to syringes, pumps, sample loops, needles, and the like.

Figure 5:
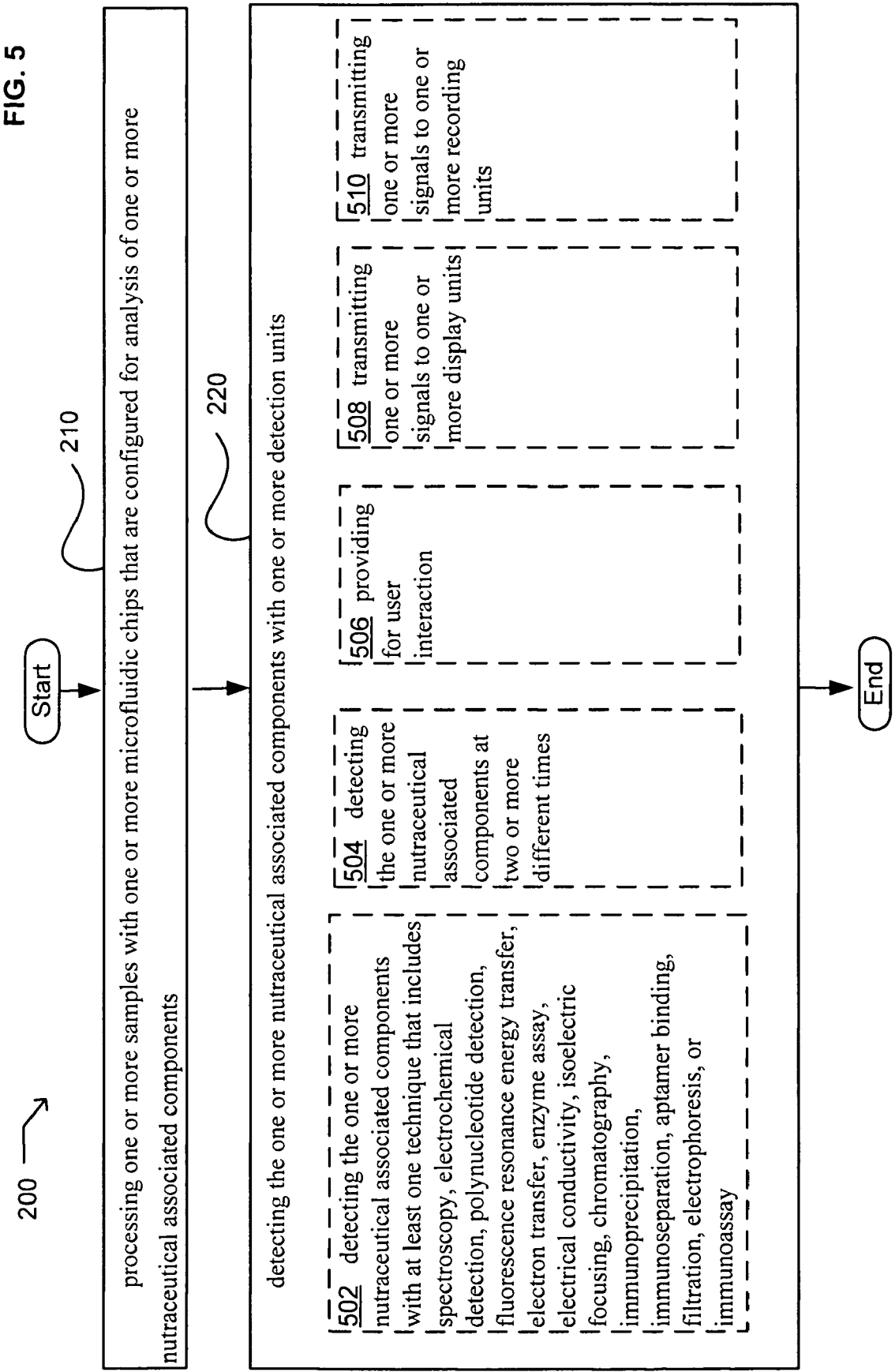
FIG. 5 illustrates alternate embodiments of the example operational flow of FIG. 2.

FIG. 5 illustrates alternative embodiments of the example operational flow 200 of FIG. 2. FIG. 5 illustrates example embodiments where the detecting operation 220 may include at least one additional operation. Additional operations may include an operation 502, an operation 504, an operation 506, an operation 508, and/or an operation 510.

At operation 502, the detecting operation 220 may include detecting the one or more nutraceutical associated components with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, or immunoassay. In some embodiments, one or more detection units 108 may detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, or immunoassay. Numerous spectroscopy based methods may be used by one or more detection units 108. Examples of such spectroscopic methods include, but are not limited to, mass spectroscopy, atomic absorption spectroscopy, nuclear magnetic resonance spectroscopy, fluorescence spectroscopy, light absorbance, light transmittance, infrared spectroscopy, raman spectroscopy, electron spin resonance, plasmon resonance spectroscopy, ultraviolet light spectroscopy, visible light spectroscopy, and the like. Electrochemical detection may be utilized by one or more detection units 108 in some embodiments. For example, in some embodiments, one or more detection units 108 may detect conductivity, electromotive force, oxidation potential, reduction potential, redox current, and the like (i.e., Xiao et al., Proc. Natl. Acad. Sci., 103:16677-16680 (2006) and Fan et al., Proc. Natl. Acad. Sci., 100:9134-9137 (2003)). In some embodiments, one or more microfluidic chips 106 may detect polynucleotide binding (Singh-Zocchi et al., Proc. Natl. Acad. Sci., 100:7605-7610 (2003) and Wang et al., Anal. Chem., 75:3941-3945 (2003)). Such polynucleotide binding may occur through hybridization of deoxyribonucleic acid, ribonucleic acid, and derivatives thereof. In some embodiments, one or more detection units 108 may detect fluorescent resonance energy transfer. For example, one or more microfluidic chips 106 may be configured for analysis of one or more nutraceutical associated components 104 through use of competition assays. Such competition assays may utilize a reaction mixture that may include a first fluorescently labeled component that binds to a second fluorescently labeled component. The presence of unlabeled component in the reaction mixture decreases the amount of labeled first component and labeled second component that bind to each other and thereby reduces fluorescence resonance energy transfer. Accordingly, detecting the level of fluorescence resonance energy transfer by a detection unit 108 allows the amount of a component in a sample 102 to be determined. Numerous other configurations may be prepared that utilize fluorescence resonance energy transfer by one or more detection units 108. Electron transfer may be utilized by one or more detection units 108 (Fan et al., Proc. Natl. Acad. Sci., 100:9134-9137 (2003)). One or more detection units 108 may detect numerous types of enzyme assays. For example, in some embodiments, such enzyme assays may be colorimetric assays. In some embodiments, one or more nutraceutical associated components 104 that stimulate or inhibit the activity of an enzyme may be detected. Accordingly, numerous types of enzyme assays may be adapted for detection of one or more nutraceutical associated components 104. Electrical conductivity may be detected by one or more detection units 108. Briefly, in some embodiments, electrodes may be directly coupled to a processor so that the processor may determine the electrical conductivity between electrodes of a particular sensor (U.S. Pat. Nos. 6,958,216 and 7,022,288; herein incorporated by reference). In some embodiments, isoelectric focusing may be used to detect one or more nutraceutical associated components 104 (i.e., U.S. Pat. Nos. 7,074,583; 7,046,357; 6,852, 206; 6,849,396; and 7,074,311; herein incorporated by reference). Briefly, isoelectric focusing may be used to characterize nutraceutical associated components 104, such as proteins, based on differences in their isoelectric points. The nutraceutical associated components 104 may then be detected according to their position within a pH gradient. Numerous chromatographic methods may be used to detect one or more nutraceutical associated components 104. Examples of such chromatographic methods include, but are not limited to, gel filtration chromatography, ion-exchange chromatography, affinity chromatography, and the like. In some embodiments, immunoseparation may be used to detect one or more nutraceutical associated components 104. Briefly, one or more nutraceutical associated components 104 may be detected upon binding to an antibody or an antibody fragment. In some embodiments, aptamer binding may be used to detect one or more nutraceutical associated components 104. Briefly, one or more nutraceutical associated components 104 may be detected upon binding to an aptamer. Numerous types of aptamers may be utilized to detect nutraceutical associated components 104. Examples of aptamers include, but are not limited to, peptide aptamers and polynucleotide aptamers. In some embodiments, filtration may be used to detect one or more nutraceutical associated components 104. For example, one or more nutraceutical associated components 104 may be detected based on their ability and/or inability to pass through a filter. Such filters may separate nutraceutical associated components 104 based on numerous properties. Examples of such properties include, but are not limited to, molecular weight, charge, hydrophobicity, hydrophilicity, and the like. In some embodiments, electrophoresis may be used to detect one or more nutraceutical associated components 104. Such methods are known in the art (Molecular Cloning: A Laboratory Manual, Cold Spring Harbor Laboratory Press; 3rd edition (Jan. 15, 2001)). In some embodiments, immunoassay may be used to detect one or more nutraceutical associated components 104. Such methods are known in the art (Molecular Cloning: A Laboratory Manual, Cold Spring Harbor Laboratory Press; 3rd edition (Jan. 15, 2001)). Combinations of numerous methods may be used to detect one or more nutraceutical associated components 104. For example, in some embodiments, electrophoresis may be combined with colorimetric methods.

At operation 504, the detecting operation 220 may include detecting the one or more nutraceutical associated components at two or more different times. In some embodiments, one or more detection units 108 may be used to detect one or more nutraceutical associated components 104 at two or more different times. In some embodiments, two or more samples 102 that include one or more nutraceutical associated components 104 may be collected from an individual at two or more different times and analyzed. Accordingly, changes in the one or more nutraceutical associated components 104 may be followed relative to time. Such changes include, but are not limited to, changes in activity, concentration, and the like. In some embodiments, such changes may occur in response to an event. For example, in some embodiments, one or more nutraceutical associated components 104 may change in response to administration of one or more nutraceutical agents to an individual. In some embodiments, a nutraceutical associated component 104 is a nutraceutical agent. Accordingly, in some embodiments, system 100 may be used to determine the concentration of one or more nutraceutical associated components 104 following administration of one or more nutraceutical agents to an individual. In some embodiments, system 100 may be used to determine the concentration of one or more nutraceutical associated components 104 following an event or stimulus to which an individual is exposed. For example, the concentration and/or activity of one or more nutraceutical agents may be determined during and/or following exercise, food intake, pharmaceutical intake, or ingestion of other substances by an individual. Accordingly, in some embodiments, system 100 may be used to monitor nutraceutical associated components 104 that are affected by an individual's metabolism.

At operation 506, the detecting operation 220 may include providing for user interaction. In some embodiments, one or more detection units 108 may provide for user interaction. In some embodiments, one or more detection units 108 may include one or more user interfaces 114. A detection unit 108 may include numerous types of user interfaces 114. Examples of such user interfaces 114 include, but are not limited to, user interfaces 114 that utilize hardwired methods, such as keyboards, touch screens, personal digital assistant interfaces, telephone interfaces, electronic writing pads, voice recognition interfaces, and the like. User interfaces 114 may also include, but are not limited to, user interfaces 114 that utilize numerous wireless methods, such as use of the internet, mobile telephones, personal digital assistants, and the like. In some embodiments, user interaction may include input of parameters associated with an individual. Examples of such parameters include, but are not limited to, one or more individual's height, weight, age, fat percentage, physical fitness level, known allergies, activities, schedule, pharmaceutical ingestion, nutraceutical ingestion, food ingestion, alcohol consumption, and the like.

At operation 508, the detecting operation 220 may include transmitting one or more signals to one or more display units. In some embodiments, one or more detection units 108 may transmit one or more signals 116 to one or more display units 110. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

At operation 510, the detecting operation 220 may include transmitting one or more signals to one or more recording units. In some embodiments, one or more detection units 108 may transmit one or more signals 116 to one or more recording units 112. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 6:
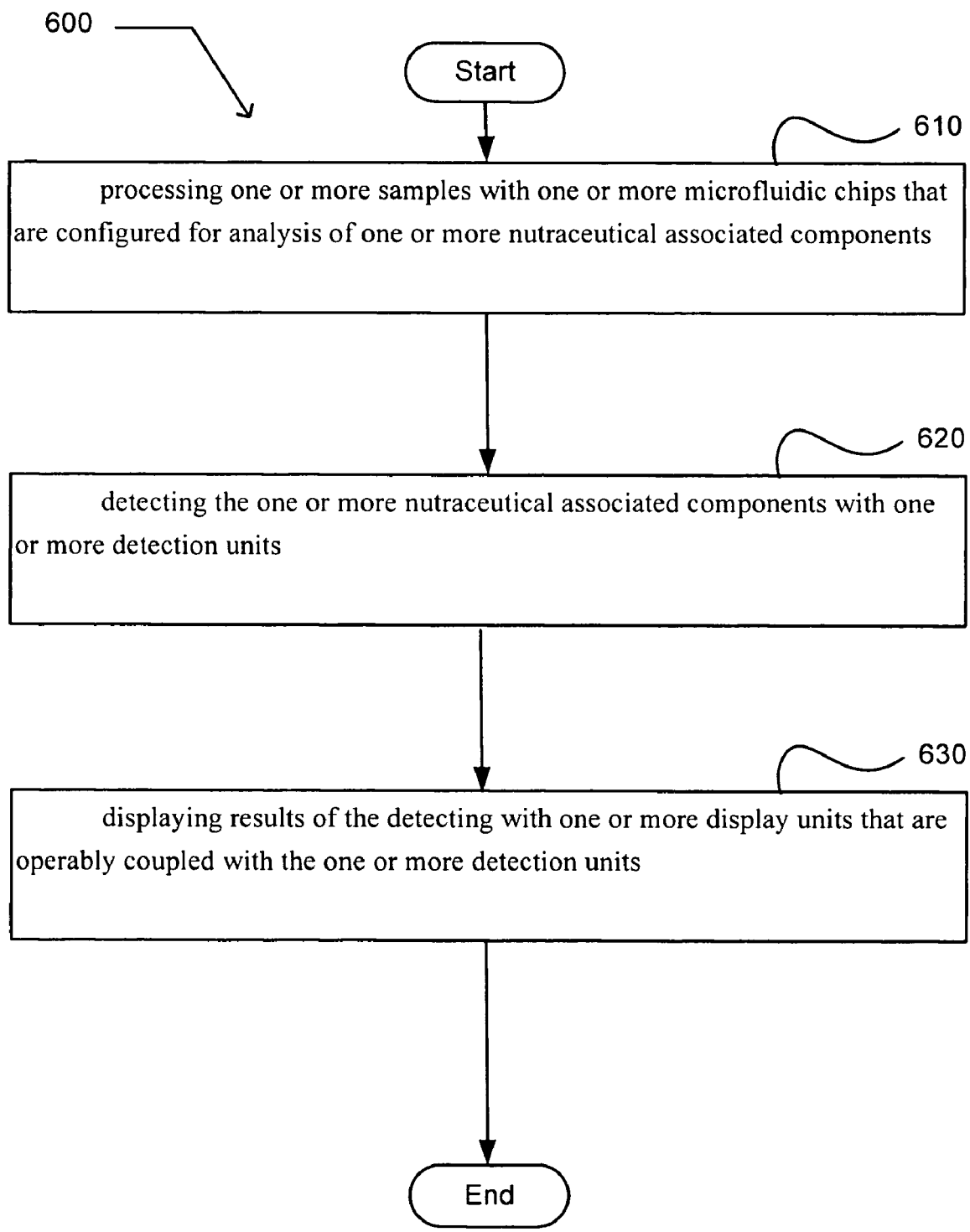
FIG. 6 illustrates an operational flow representing example operations related to methods and systems for analysis of nutraceutical associated components.

FIG. 6 illustrates an operational flow 600 representing examples of operations that are related to the performance of a method for analysis of one or more nutraceutical associated components 104. In FIG. 6 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 600 includes a processing operation 610 involving processing one or more samples with one or more microfluidic chips that are configured for analysis of one or more nutraceutical associated components. In some embodiments, one or more microfluidic chips 106 that are configured for analysis of one or more nutraceutical associated components 104 may be used to process one or more samples 102. In some embodiments, one or more microfluidic chips 106 may accept one or more samples 102. In some embodiments, one or more microfluidic chips 106 may accept one or more samples 102 acquired through use of one or more non-invasive techniques. In some embodiments, one or more microfluidic chips 106 may accept one or more samples 102 that include at least one of sweat, tears, urine, breath, skin, hair, saliva, excrement, mucus, or substantially any combination thereof. In some embodiments, one or more microfluidic chips 106 may accept one or more samples 102 that include blood. In some embodiments, one or more microfluidic chips 106 may be used to process one or more samples 102 utilizing polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, one or more microfluidic chips 106 may be used to process one or more samples 102 that include at least one of sweat, tears, urine, breath, skin, hair, saliva, excrement, blood, mucus, or substantially any combination thereof. In some embodiments, one or more microfluidic chips 106 may be used to process one or more samples 102 that include at least one hormone, prohormone, polynucleotide, enzyme, protein, vitamin, mineral, metal, antioxidant, a substantially any combination thereof. In some embodiments, one or more microfluidic chips 106 may be used to process two or more samples 102 that are collected at two or more different times. In some embodiments, one or more microfluidic chips 106 may be used to process one or more samples 102 that are configured for analysis of a single nutraceutical associated component 104. In some embodiments, one or more microfluidic chips 106 may provide for user interaction.

The operational flow 600 includes a detecting operation 620 involving detecting the one or more nutraceutical associated components with one or more detection units. In some embodiments, one or more detection units 108 may be used to detect one or more nutraceutical associated components 104. In some embodiments, one or more detection units 108 may be used to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be used to detect one or more nutraceutical associated components 104 that are associated with two or more samples 102 that were collected at two or more different times. In some embodiments, one or more detection units 108 may provide for user interaction. In some embodiments, one or more detection units 108 may be used to transmit one or more signals 116 to one or more display units 110. In some embodiments, one or more detection units 108 may be used to transmit one or more signals 116 to one or more recording units 112.

The operational flow 600 includes a displaying operation 630 involving displaying results of the detecting with one or more display units that are operably coupled with the one or more detection units. In some embodiments, one or more display units 110 may be used to display the results of the detecting. In some embodiments, one or more display units 110 may be used to display results in human-readable format. In some embodiments, one or more display units 110 may be used to display results in machine-readable format. In some embodiments, one or more display units 110 may be used to display if one or more nutraceutical associated components are present or absent within one or more samples 102. In some embodiments, one or more display units 110 may be used to display one or more concentrations of one or more nutraceutical associated components 104. In some embodiments, one or more display units 110 may be used to receive one or more signals 116 from one or more detection units 108. In some embodiments, one or more display units 110 may be used to display one or more concentrations of one or more nutraceutical associated components 104 associated with two or more samples 102 that were collected at two or more different times. In some embodiments, one or more display units 110 may be used to display one or more messages indicating one or more dosages of one or more nutraceutical agents for supplementation of an individual. In some embodiments, one or more display units 110 may provide for user interaction. In some embodiments, one or more display units 110 may be used to transmit one or more signals 116 to one or more display units 110. In some embodiments, one or more display units 110 may be used to transmit one or more signals 116 to one or more recording units 112.

Figure 7:
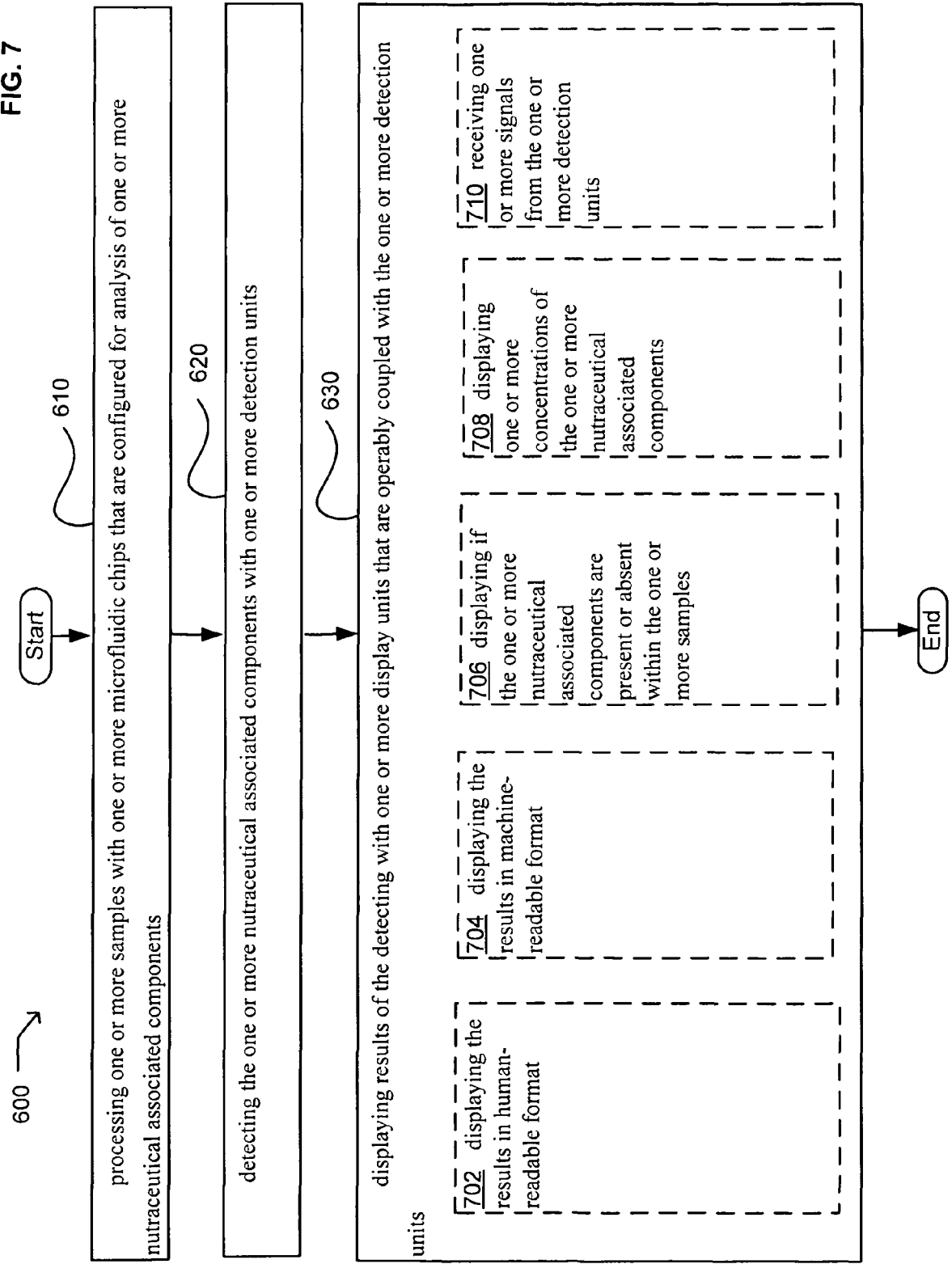
FIG. 7 illustrates alternate embodiments of the example operational flow of FIG. 6.

FIG. 7 illustrates alternative embodiments of the example operational flow 600 of FIG. 6. FIG. 7 illustrates example embodiments where the displaying operation 630 may include at least one additional operation. Additional operations may include an operation 702, an operation 704, an operation 706, an operation 708, and/or an operation 710.

At operation 702, the displaying operation 630 may include displaying the results in human-readable format. In some embodiments, one or more display units 110 may display one or more results in human-readable format. Examples of human-readable formats include, but are not limited to, written language, verbal communications, Braille output, pictographic output, graphical output, colorographic output, and the like.

At operation 704, the displaying operation 630 may include displaying the results in machine-readable format. In some embodiments, one or more display units 110 may display one or more results in machine-readable format. Examples of machine-readable formats include, but are not limited to, electrical signals 116, bar codes, graphical patterns, punch cards, encoding on a computer-readable medium, magnetic encoding, digital coding, optical coding, and the like.

At operation 706, the displaying operation 630 may include displaying if the one or more nutraceutical associated components are present or absent within the one or more samples. In some embodiments, one or more display units 110 may display if one or more nutraceutical associated components 104 that are present or absent within one or more samples 102. In some embodiments, one or more display units 110 may display the identity of one or more nutraceutical associated components 104 that are present or absent within one or more samples 102. For example, in some embodiments, system 100 may be used to determine if one or more nutraceutical associated components 104, such as one or more nutraceutical agents, are present or absent from one or more food supplements, foods, bodily samples 102, and the like.

At operation 708, the displaying operation 630 may include displaying one or more concentrations of the one or more nutraceutical associated components. In some embodiments, one or more display units 110 may display one or more concentrations of one or more nutraceutical associated components 104 that are present or absent within one or more samples 102. Concentrations of one or more nutraceutical associated components 104 may be displayed in numerous formats. For example, in some embodiments, concentration may be expressed in quantity terms that include, but are not limited to, grams, milligrams, nanograms, and the like. In some embodiments, concentrations may be expressed in quantity per volume of sample 102. For example, in some embodiments, concentration may be expressed as molarity, molality, grams per liter, milligrams per liter, milligrams per deciliter, and the like.

At operation 710, the displaying operation 630 may include receiving one or more signals from the one or more detection units. In some embodiments, one or more display units 110 may receive one or more signals 116 from one or more detection units 108. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 8:
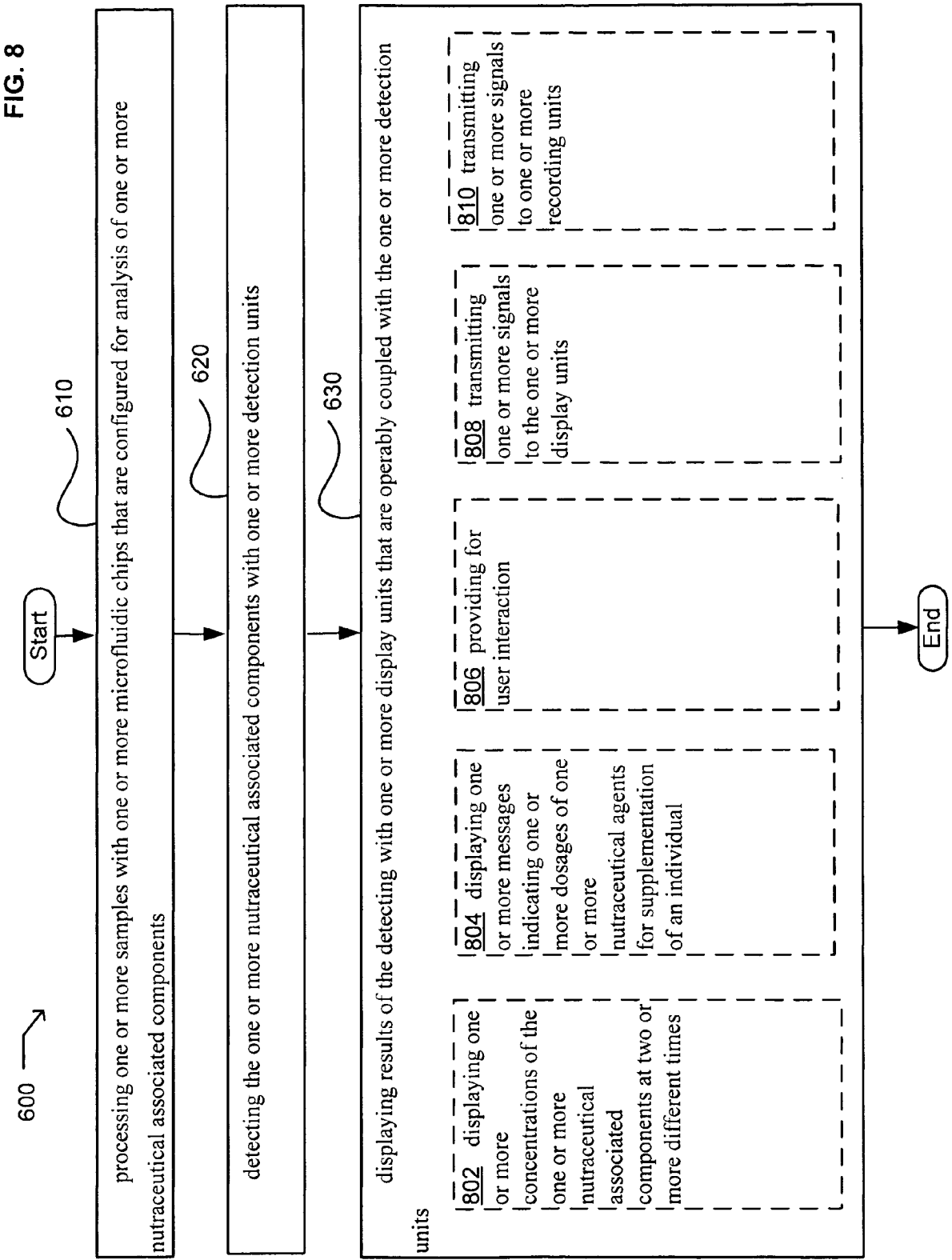
FIG. 8 illustrates alternate embodiments of the example operational flow of FIG. 6.

FIG. 8 illustrates alternative embodiments of the example operational flow 600 of FIG. 6. FIG. 8 illustrates example embodiments where the displaying operation 630 may include at least one additional operation. Additional operations may include an operation 802, an operation 804, an operation 806, an operation 808, and/or an operation 810.

At operation 802, the displaying operation 630 may include displaying one or more concentrations of the one or more nutraceutical associated components at two or more different times. In some embodiments, one or more display units 110 may display one or more concentrations of one or more nutraceutical associated components 104 at two or more different times. In some embodiments, one or more display units 110 may display one or more concentrations of one or more nutraceutical associated components 104 present within two or more samples 102 that were collected at two or more different times. In some embodiments, one or more display units 110 may display two or more concentrations of one or more nutraceutical associated components 104 in graphical form. For example, in some embodiments, concentrations may be displayed as a bar graph, a line graph, a pie chart, and the like. Accordingly, in some embodiments, a user 118 may plot two or more concentrations of one or more nutraceutical associated components 104. Numerous plot formats may be used. Examples of such formats include, but are not limited to, concentration versus time from ingestion of one or more nutraceutical agents, concentration versus time from an event, such as exercise, sleep, injury, and the like. Accordingly, in some embodiments, system 100 may be used to predict the concentration of one or more nutraceutical agents within a sample 102 obtained from an individual at one or more times. For example, in some embodiments, an individual can predict the concentration of one or more nutraceutical associated components 104 in blood samples 102 obtained from an individual following ingestion of one or more nutraceutical agents.

At operation 804, the displaying operation 630 may include displaying one or more messages indicating one or more dosages of one or more nutraceutical agents for supplementation of an individual. In some embodiments, one or more display units 110 may display one or more messages indicating one or more dosages of one or more nutraceutical agents for supplementation of an individual. In some embodiments, system 100 may be used to determine one or more concentrations of one or more nutraceutical associated components 104 included within one or more samples 102 obtained from an individual and then display one or more concentrations of one or more nutraceutical agents for supplementation of the individual. For example, in some embodiments, the concentration of calcium may be determined to be low in a sample 102 obtained from an individual and the display unit 110 may indicate a dosage of a calcium supplement for administration to the individual. Accordingly, one or more display units 110 may display one or more dosages of numerous types of nutraceutical agents for administration to one or more individuals.

At operation 806, the displaying operation 630 may include providing for user interaction. In some embodiments, one or more display units 110 may provide for user interaction. In some embodiments, one or more display units 110 may include one or more user interfaces 114. A display unit 110 may include numerous types of user interfaces 114. Examples of such user interfaces 114 include, but are not limited to, user interfaces 114 that utilize hardwired methods, such as keyboards, touch screens, personal digital assistant interfaces, telephone interfaces, electronic writing pads, voice recognition interfaces, and the like. User interfaces 114 may also include, but are not limited to, user interfaces 114 that utilize numerous wireless methods, such as use of the internet, mobile telephones, personal digital assistants, and the like. In some embodiments, user interaction may include input of parameters associated with an individual. Examples of such parameters include, but are not limited to, one or more individual's height, weight, age, fat percentage, physical fitness level, known allergies, activities, schedule, pharmaceutical ingestion, nutraceutical ingestion, food ingestion, alcohol consumption, and the like.

At operation 808, the displaying operation 630 may include transmitting one or more signals to the one or more display units. In some embodiments, one or more display units 110 may transmit one or more signals 116 to one or more display units 110. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof. In some embodiments, one or more display units 110 may transmit one or more signals 116 to one or more remote display units 110. For example, in some embodiments, one or more display units 110 may transmit one or more signals 116 to one or more remote display units 110 that are located in the office of a physician, nurse, dietician, pharmacist, coach, personal trainer, clerk at a food supplement store, clerk at a grocery store, and the like.

At operation 810, the displaying operation 630 may include transmitting one or more signals to one or more recording units. In some embodiments, one or more display units 110 may transmit one or more signals 116 to one or more recording units 112. In some embodiments, one or more display units 110 may transmit one or more signals 116 to one or more recording units 112. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 9:
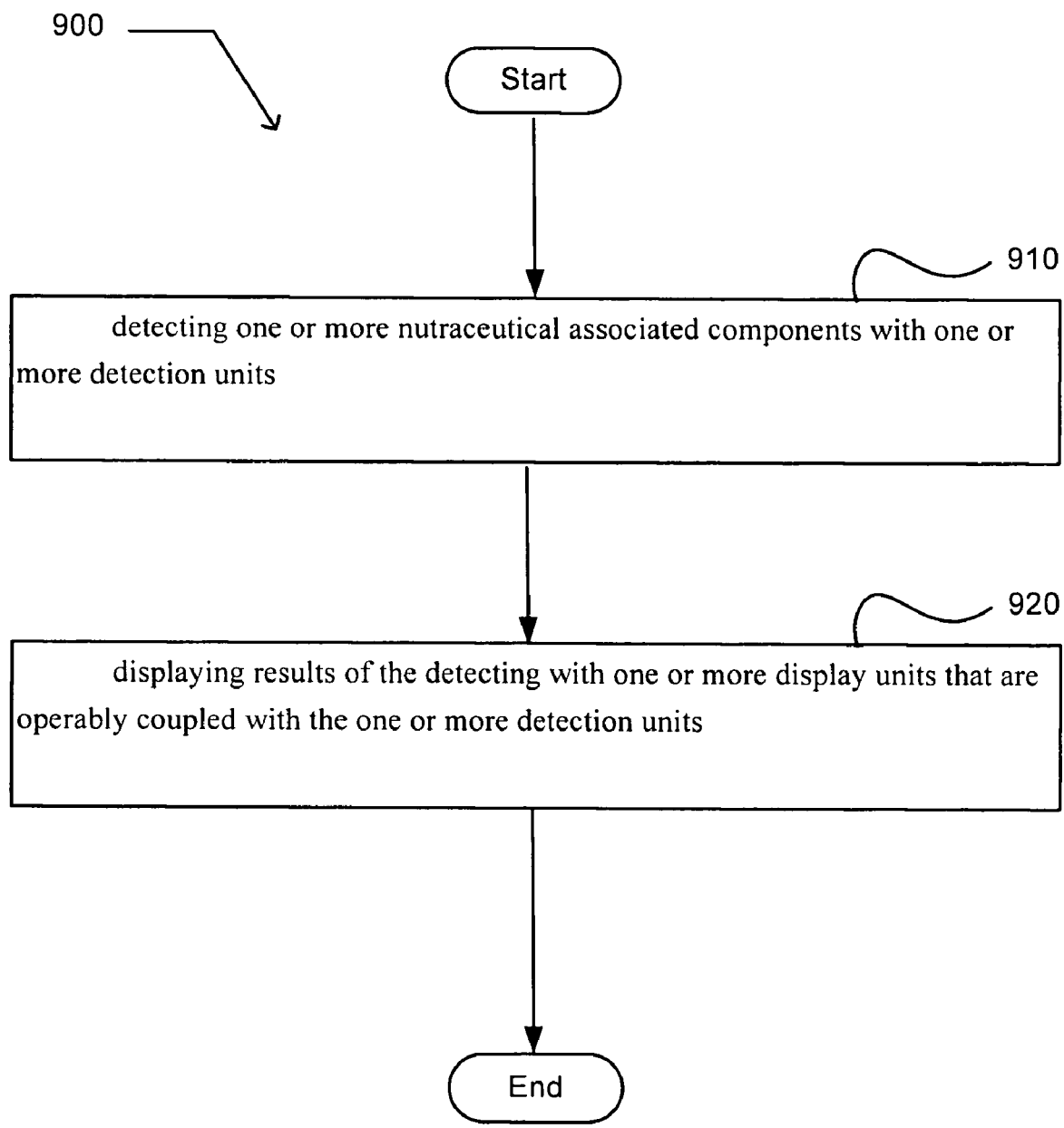
FIG. 9 illustrates an operational flow representing example operations related to methods and systems for analysis of nutraceutical associated components.

FIG. 9 illustrates an operational flow 900 representing examples of operations that are related to the performance of a method for analysis of one or more nutraceutical associated components 104. In FIG. 9 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

The operational flow 900 includes a detecting operation 910 involving detecting one or more nutraceutical associated components with one or more detection units. In some embodiments, one or more detection units 108 may be used to detect one or more nutraceutical associated components 104. In some embodiments, one or more detection units 108 may be used to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be used to detect one or more nutraceutical associated components 104 that are associated with two or more samples 102 that were collected at two or more different times. In some embodiments, one or more detection units 108 may provide for user interaction. In some embodiments, one or more detection units 108 may be used to transmit one or more signals 116 to one or more display units 110. In some embodiments, one or more detection units 108 may be used to transmit one or more signals 116 to one or more recording units 112.

The operational flow 900 includes a displaying operation 920 involving displaying results of the detecting with one or more display units that are operably coupled with the one or more detection units. In some embodiments, one or more display units 110 may be used to display the results of the detecting. In some embodiments, one or more display units 110 may be used to display results in human-readable format. In some embodiments, one or more display units 110 may be used to display results in machine-readable format. In some embodiments, one or more display units 110 may be used to display if one or more nutraceutical associated components are present or absent within one or more samples 102. In some embodiments, one or more display units 110 may be used to display one or more concentrations of one or more nutraceutical associated components 104. In some embodiments, one or more display units 110 may be used to receive one or more signals 116 from one or more detection units 108. In some embodiments, one or more display units 110 may be used to display one or more concentrations of one or more nutraceutical associated components 104 associated with two or more samples 102 that were collected at two or more different times. In some embodiments, one or more display units 110 may be used to display one or more messages indicating one or more dosages of one or more nutraceutical agents for supplementation of an individual. In some embodiments, one or more display units 110 may provide for user interaction. In some embodiments, one or more display units 110 may be used to transmit one or more signals 116 to one or more display units 110. In some embodiments, one or more display units 110 may be used to transmit one or more signals 116 to one or more recording units 112.

Figure 10:
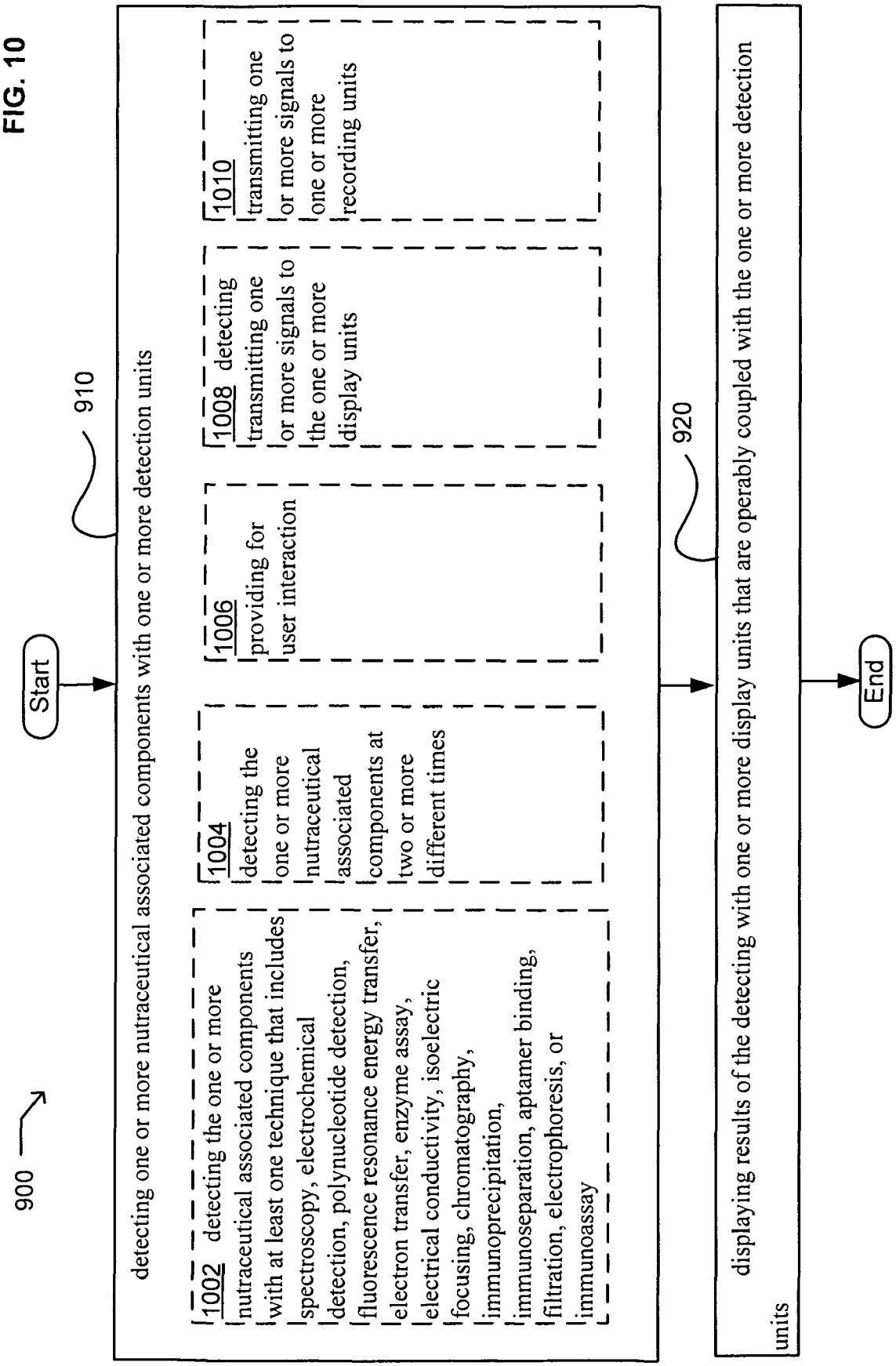
FIG. 10 illustrates alternate embodiments of the example operational flow of FIG. 9.

FIG. 10 illustrates alternative embodiments of the example operational flow 900 of FIG. 9. FIG. 10 illustrates example embodiments where the detecting operation 910 may include at least one additional operation. Additional operations may include an operation 1002, an operation 1004, an operation 1006, an operation 1008, and/or an operation 1010.

At operation 1002, the detecting operation 910 may include detecting the one or more nutraceutical associated components with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, or immunoassay. In some embodiments, one or more detection units 108 may detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, or immunoassay. Numerous spectroscopy based methods may be used by one or more detection units 108. Examples of such spectroscopic methods include, but are not limited to, mass spectroscopy, atomic absorption spectroscopy, nuclear magnetic resonance spectroscopy, fluorescence spectroscopy, light absorbance, light transmittance, infrared spectroscopy, raman spectroscopy, electron spin resonance, plasmon resonance spectroscopy, ultraviolet light spectroscopy, visible light spectroscopy, and the like. Electrochemical detection may be utilized by one or more detection units 108 in some embodiments. For example, in some embodiments, one or more detection units 108 may detect conductivity, electromotive force, oxidation potential, reduction potential, redox current, and the like (i.e., Xiao et al., Proc. Natl. Acad. Sci., 103:16677-16680 (2006) and Fan et al., Proc. Natl. Acad. Sci., 100:9134-9137 (2003)). In some embodiments, one or more microfluidic chips 106 may detect polynucleotide binding (Singh-Zocchi et al., Proc. Natl. Acad. Sci., 100:7605-7610 (2003) and Wang et al., Anal. Chem., 75:3941-3945 (2003)). Such polynucleotide binding may occur through hybridization of deoxyribonucleic acid, ribonucleic acid, and derivatives thereof. In some embodiments, one or more detection units 108 may detect fluorescent resonance energy transfer. For example, one or more microfluidic chips 106 may be configured for analysis of one or more nutraceutical associated components 104 through use of competition assays. Such competition assays may utilize a reaction mixture that may include a first fluorescently labeled component that binds to a second fluorescently labeled component. The presence of unlabeled component in the reaction mixture decreases the amount of labeled first component and labeled second component that bind to each other and thereby reduces fluorescence resonance energy transfer. Accordingly, detecting the level of fluorescence resonance energy transfer by a detection unit 108 allows the amount of a component in a sample 102 to be determined. Numerous other configurations may be prepared that utilize fluorescence resonance energy transfer by one or more detection units 108. Electron transfer may be utilized by one or more detection units 108 (Fan et al., Proc. Natl. Acad. Sci., 100:9134-9137 (2003)). One or more detection units 108 may detect numerous types of enzyme assays. For example, in some embodiments, such enzyme assays may be colorimetric assays. In some embodiments, one or more nutraceutical associated components 104 that stimulate or inhibit the activity of an enzyme may be detected. Accordingly, numerous types of enzyme assays may be adapted for detection of one or more nutraceutical associated components 104. Electrical conductivity may be detected by one or more detection units 108. Briefly, in some embodiments, electrodes may be directly coupled to a processor so that the processor may determine the electrical conductivity between electrodes of a particular sensor (U.S. Pat. Nos. 6,958,216 and 7,022,288; herein incorporated by reference). In some embodiments, isoelectric focusing may be used to detect one or more nutraceutical associated components 104 (i.e., U.S. Pat. Nos. 7,074,583; 7,046,357; 6,852,206; 6,849,396; and 7,074,311; herein incorporated by reference). Briefly, isoelectric focusing may be used to characterize nutraceutical associated components 104, such as proteins, based on differences in their isoelectric points. The nutraceutical associated components 104 may then be detected according to their position within a pH gradient. Numerous chromatographic methods may be used to detect one or more nutraceutical associated components 104. Examples of such chromatographic methods include, but are not limited to, gel filtration chromatography, ion-exchange chromatography, affinity chromatography, and the like. In some embodiments, immunoseparation may be used to detect one or more nutraceutical associated components 104. Briefly, one or more nutraceutical associated components 104 may be detected upon binding to an antibody or an antibody fragment. In some embodiments, aptamer binding may be used to detect one or more nutraceutical associated components 104. Briefly, one or more nutraceutical associated components 104 may be detected upon binding to an aptamer.

Numerous types of aptamers may be utilized to detect nutraceutical associated components 104. Examples of aptamers include, but are not limited to, peptide aptamers and polynucleotide aptamers. In some embodiments, filtration may be used to detect one or more nutraceutical associated components 104. For example, one or more nutraceutical associated components 104 may be detected based on their ability and/or inability to pass through a filter. Such filters may separate nutraceutical associated components 104 based on numerous properties. Examples of such properties include, but are not limited to, molecular weight, charge, hydrophobicity, hydrophilicity, and the like. In some embodiments, electrophoresis may be used to detect one or more nutraceutical associated components 104. Such methods are known in the art (Molecular Cloning: A Laboratory Manual, Cold Spring Harbor Laboratory Press; 3rd edition (Jan. 15, 2001)). In some embodiments, immunoassay may be used to detect one or more nutraceutical associated components 104. Such methods are known in the art (Molecular Cloning: A Laboratory Manual, Cold Spring Harbor Laboratory Press; 3rd edition (Jan. 15, 2001)). Combinations of numerous methods may be used to detect one or more nutraceutical associated components 104. For example, in some embodiments, electrophoresis may be combined with colorimetric methods.

At operation 1004, the detecting operation 910 may include detecting the one or more nutraceutical associated components at two or more different times. In some embodiments, one or more detection units 108 may be used to detect one or more nutraceutical associated components 104 at two or more different times. In some embodiments, two or more samples 102 that include one or more nutraceutical associated components 104 may be collected from an individual at two or more different times and analyzed. Accordingly, changes in the one or more nutraceutical associated components 104 may be followed relative to time. Such changes include, but are not limited to, changes in activity, concentration, and the like. In some embodiments, such changes may occur in response to an event. For example, in some embodiments, one or more nutraceutical associated components 104 may change in response to administration of one or more nutraceutical agents to an individual. In some embodiments, a nutraceutical associated component 104 is a nutraceutical agent. Accordingly, in some embodiments, system 100 may be used to determine the concentration of one or more nutraceutical associated components 104 following administration of one or more nutraceutical agents to an individual. In some embodiments, system 100 may be used to determine the concentration of one or more nutraceutical associated components 104 following an event or stimulus to which an individual is exposed. For example, the concentration and/or activity of one or more nutraceutical agents may be determined during and/or following exercise, food intake, pharmaceutical intake, or ingestion of other substances by an individual. Accordingly, in some embodiments, system 100 may be used to monitor nutraceutical associated components 104 that are affected by an individual's metabolism.

At operation 1006, the detecting operation 910 may include providing for user interaction. In some embodiments, one or more detection units 108 may provide for user interaction. In some embodiments, one or more detection units 108 may include one or more user interfaces 114. A detection unit 108 may include numerous types of user interfaces 114. Examples of such user interfaces 114 include, but are not limited to, user interfaces 114 that utilize hardwired methods, such as keyboards, touch screens, personal digital assistant interfaces, telephone interfaces, electronic writing pads, voice recognition interfaces, and the like. User interfaces 114 may also include, but are not limited to, user interfaces 114 that utilize numerous wireless methods, such as use of the internet, mobile telephones, personal digital assistants, and the like. In some embodiments, user interaction may include input of parameters associated with an individual. Examples of such parameters include, but are not limited to, one or more individual's height, weight, age, fat percentage, physical fitness level, known allergies, activities, schedule, pharmaceutical ingestion, nutraceutical ingestion, food ingestion, alcohol consumption, and the like.

At operation 1008, the detecting operation 910 may include transmitting one or more signals to the one or more display units. In some embodiments, one or more detection units 108 may transmit one or more signals 116 to one or more display units 110. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

At operation 1010, the detecting operation 910 may include transmitting one or more signals to one or more recording units. In some embodiments, one or more detection units 108 may transmit one or more signals 116 to one or more recording units 112. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 11:
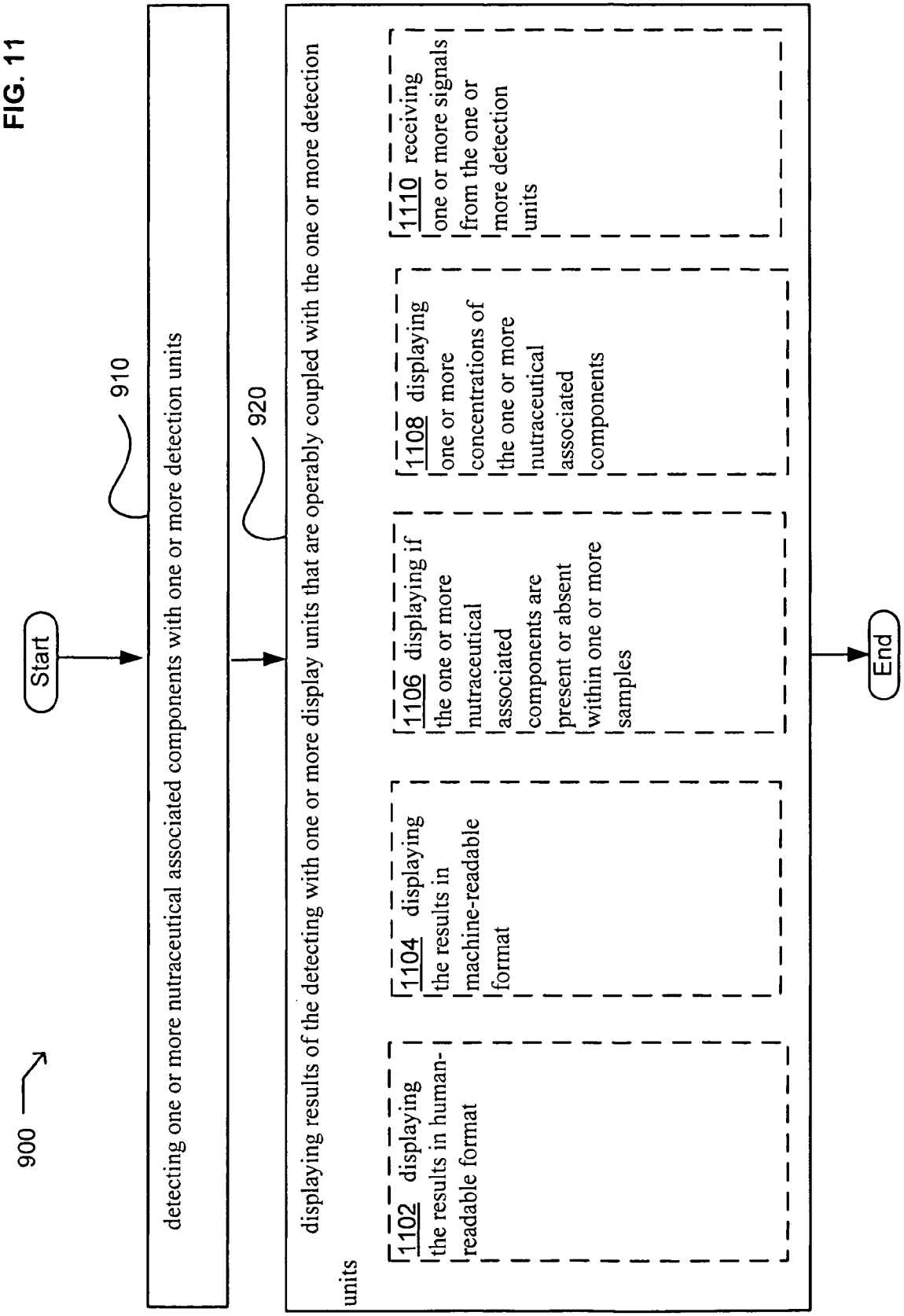
FIG. 11 illustrates alternate embodiments of the example operational flow of FIG. 9.

FIG. 11 illustrates alternative embodiments of the example operational flow 900 of FIG. 9. FIG. 11 illustrates example embodiments where the displaying operation 920 may include at least one additional operation. Additional operations may include an operation 1102, an operation 1104, an operation 1106, an operation 1108, and/or an operation 1110.

At operation 1102, the displaying operation 920 may include displaying the results in human-readable format. In some embodiments, one or more display units 110 may display one or more results in human-readable format. Examples of human-readable formats include, but are not limited to, written language, verbal communications, Braille output, pictographic output, graphical output, colorographic output, and the like.

At operation 1104, the displaying operation 920 may include displaying the results in machine-readable format. In some embodiments, one or more display units 110 may display one or more results in machine-readable format. Examples of machine-readable formats include, but are not limited to, electrical signals 116, bar codes, graphical patterns, punch cards, encoding on a computer-readable medium, magnetic encoding, digital coding, optical coding, and the like.

At operation 1106, the displaying operation 920 may include displaying if the one or more nutraceutical associated components are present or absent within one or more samples. In some embodiments, one or more display units 110 may display if one or more nutraceutical associated components 104 are present or absent within one or more samples 102. In some embodiments, one or more display units 110 may display the identity of one or more nutraceutical associated components 104 are present or absent within one or more samples 102. For example, in some embodiments, system 100 may be used to determine if one or more nutraceutical associated components 104, such as one or more nutraceutical agents, are present or absent from one or more food supplements, foods, bodily samples 102, and the like.

At operation 1108, the displaying operation 920 may include displaying one or more concentrations of the one or more nutraceutical associated components. In some embodiments, one or more display units 110 may display one or more concentrations of one or more nutraceutical associated components 104 that are present or absent within one or more samples 102. Concentrations of one or more nutraceutical associated components 104 may be displayed in numerous formats. For example, in some embodiments, concentration may be expressed in quantity terms that include, but are not limited to, grams, milligrams, nanograms, and the like. In some embodiments, concentrations may be expressed in quantity per volume of sample 102. For example, in some embodiments, concentration may be expressed as molarity, molality, grams per liter, milligrams per liter, milligrams per deciliter, and the like.

At operation 1110, the displaying operation 920 may include receiving one or more signals from the one or more detection units. In some embodiments, one or more display units 110 may receive one or more signals 116 from one or more detection units 108. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 12:
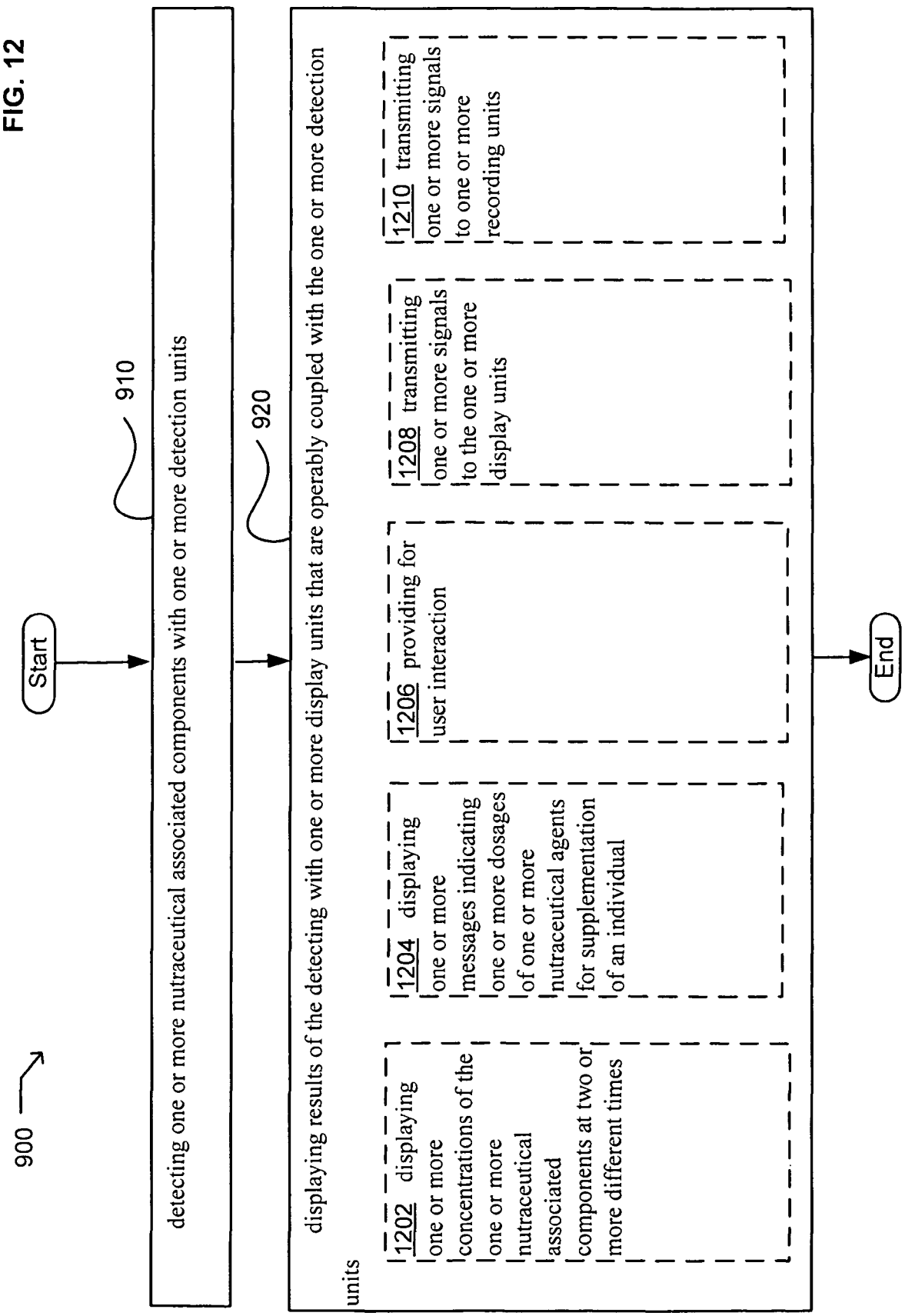
FIG. 12 illustrates alternate embodiments of the example operational flow of FIG. 9.

FIG. 12 illustrates alternative embodiments of the example operational flow 900 of FIG. 9. FIG. 12 illustrates example embodiments where the displaying operation 920 may include at least one additional operation. Additional operations may include an operation 1202, an operation 1204, an operation 1206, an operation 1208, and/or an operation 1210.

At operation 1202, the displaying operation 920 may include displaying one or more concentrations of the one or more nutraceutical associated components at two or more different times. In some embodiments, one or more display units 110 may display one or more concentrations of one or more nutraceutical associated components 104 at two or more different times. In some embodiments, one or more display units 110 may display one or more concentrations of one or more nutraceutical associated components 104 present within two or more samples 102 that were collected at two or more different times. In some embodiments, one or more display units 110 may display two or more concentrations of one or more nutraceutical associated components 104 in graphical form. For example, in some embodiments, concentrations may be displayed as a bar graph, a line graph, a pie chart, and the like. Accordingly, in some embodiments, a user 118 may plot two or more concentrations of one or more nutraceutical associated components 104. Numerous plot formats may be used. Examples of such formats include, but are not limited to, concentration versus time from ingestion of one or more nutraceutical agents, concentration versus time from an event, such as exercise, sleep, injury, and the like. Accordingly, in some embodiments, system 100 may be used to predict the concentration of one or more nutraceutical agents within a sample 102 obtained from an individual at one or more times. For example, in some embodiments, an individual can predict the concentration of one or more nutraceutical associated components 104 in blood samples 102 obtained from an individual following ingestion of one or more nutraceutical agents.

At operation 1204, the displaying operation 920 may include displaying one or more messages indicating one or more dosages of one or more nutraceutical agents for supplementation of an individual. In some embodiments, one or more display units 110 may display one or more messages indicating one or more dosages of one or more nutraceutical agents for supplementation of an individual. In some embodiments, system 100 may be used to determine one or more concentrations of one or more nutraceutical associated components 104 included within one or more samples 102 obtained from an individual and then display one or more concentrations of one or more nutraceutical agents for supplementation of the individual. For example, in some embodiments, the concentration of calcium may be determined to be low in a sample 102 obtained from an individual and the display unit 110 may indicate a dosage of a calcium supplement for administration to the individual. Accordingly, one or more display units 110 may display one or more dosages of numerous types of nutraceutical agents for administration to one or more individuals.

At operation 1206, the displaying operation 920 may include providing for user interaction. In some embodiments, one or more display units 110 may provide for user interaction. In some embodiments, one or more display units 110 may include one or more user interfaces 114. A display unit 110 may include numerous types of user interfaces 114. Examples of such user interfaces 114 include, but are not limited to, user interfaces 114 that utilize hardwired methods, such as keyboards, touch screens, personal digital assistant interfaces, telephone interfaces, electronic writing pads, voice recognition interfaces, and the like. User interfaces 114 may also include, but are not limited to, user interfaces 114 that utilize numerous wireless methods, such as use of the internet, mobile telephones, personal digital assistants, and the like. In some embodiments, user interaction may include input of parameters associated with an individual. Examples of such parameters include, but are not limited to, one or more individual's height, weight, age, fat percentage, physical fitness level, known allergies, activities, schedule, pharmaceutical ingestion, nutraceutical ingestion, food ingestion, alcohol consumption, and the like.

At operation 1208, the displaying operation 920 may include transmitting one or more signals to the one or more display units. In some embodiments, one or more display units 110 may transmit one or more signals 116 to one or more display units 110. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof. In some embodiments, one or more display units 110 may transmit one or more signals 116 to one or more remote display units 110. For example, in some embodiments, one or more display units 110 may transmit one or more signals 116 to one or more remote display units 110 that are located in the office of a physician, nurse, dietician, pharmacist, coach, personal trainer, clerk at a food supplement store, clerk at a grocery store, and the like.

At operation 1210, the displaying operation 920 may include transmitting one or more signals to one or more recording units. In some embodiments, one or more display units 110 may transmit one or more signals 116 to one or more recording units 112. In some embodiments, one or more display units 110 may transmit one or more signals 116 to one or more recording units 112. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 13:
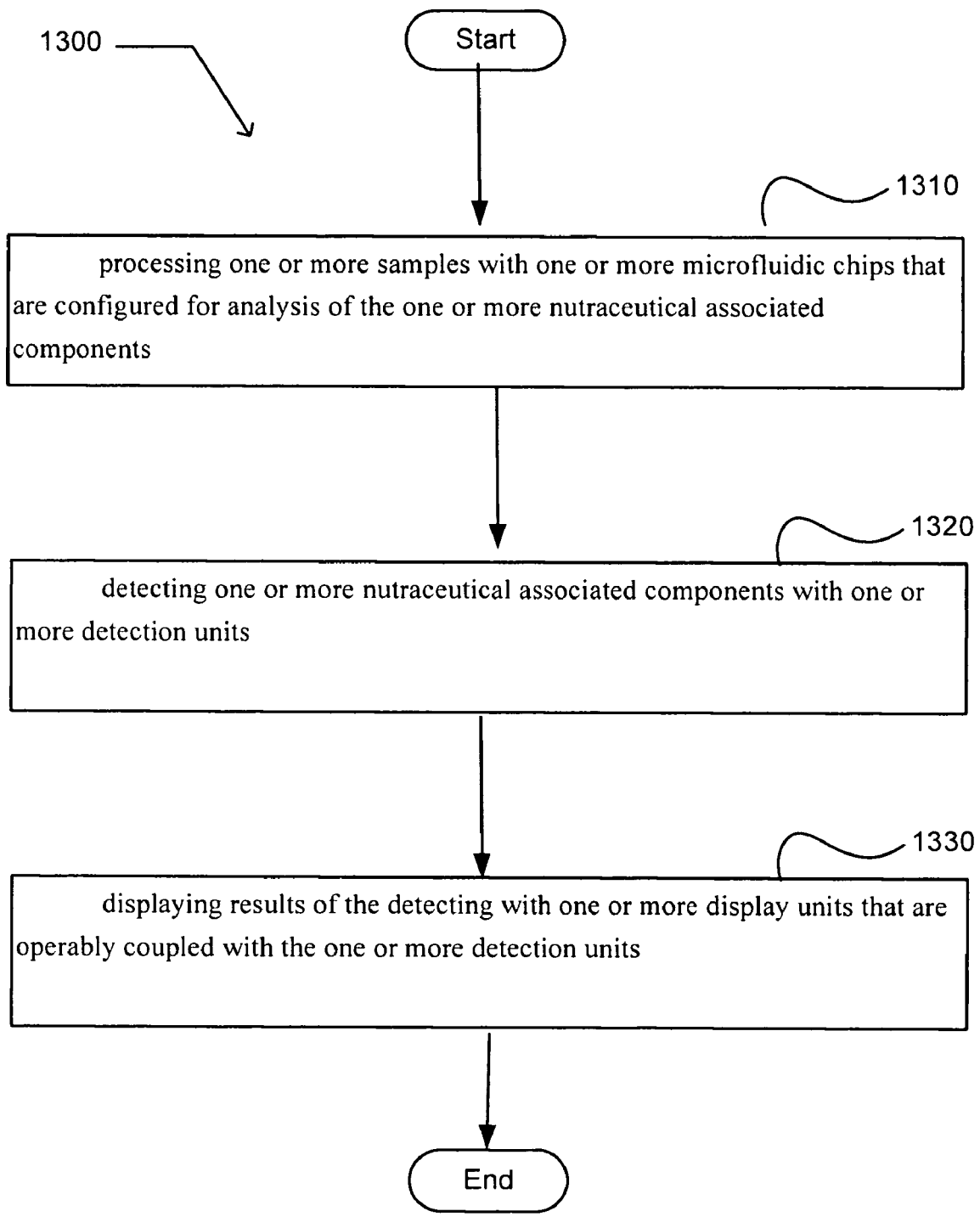
FIG. 13 illustrates an operational flow representing example operations related to methods and systems for analysis of nutraceutical associated components.

FIG. 13 illustrates an operational flow 1300 representing examples of operations that are related to the performance of a method for analysis of one or more nutraceutical associated components 104. In FIG. 13 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

The operational flow 1300 includes a processing operation 1310 involving processing one or more samples with one or more microfluidic chips that are configured for analysis of the one or more nutraceutical associated components. In some embodiments, one or more microfluidic chips 106 that are configured for analysis of one or more nutraceutical associated components 104 may be used to process one or more samples 102. In some embodiments, one or more microfluidic chips 106 may accept one or more samples 102. In some embodiments, one or more microfluidic chips 106 may accept one or more samples 102 acquired through use of one or more non-invasive techniques. In some embodiments, one or more microfluidic chips 106 may accept one or more samples 102 that include at least one of sweat, tears, urine, breath, skin, hair, saliva, excrement, mucus, or substantially any combination thereof. In some embodiments, one or more microfluidic chips 106 may accept one or more samples 102 that include blood. In some embodiments, one or more microfluidic chips 106 may be used to process one or more samples 102 utilizing polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, one or more microfluidic chips 106 may be used to process one or more samples 102 that include at least one of sweat, tears, urine, breath, skin, hair, saliva, excrement, blood, mucus, or substantially any combination thereof. In some embodiments, one or more microfluidic chips 106 may be used to process one or more samples 102 that include at least one hormone, prohormone, polynucleotide, enzyme, protein, vitamin, mineral, metal, antioxidant, or substantially any combination thereof. In some embodiments, one or more microfluidic chips 106 may be used to process two or more samples 102 that are collected at two or more different times. In some embodiments, one or more microfluidic chips 106 may be used to process one or more samples 102 that are configured for analysis of a single nutraceutical associated component 104. In some embodiments, one or more microfluidic chips 106 may provide for user interaction.

The operational flow 1300 includes a detecting operation 1320 involving detecting one or more nutraceutical associated components with one or more detection units. In some embodiments, one or more detection units 108 may be used to detect one or more nutraceutical associated components 104. In some embodiments, one or more detection units 108 may be used to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be used to detect one or more nutraceutical associated components 104 that are associated with two or more samples 102 that were collected at two or more different times. In some embodiments, one or more detection units 108 may provide for user interaction. In some embodiments, one or more detection units 108 may be used to transmit one or more signals 116 to one or more display units 110. In some embodiments, one or more detection units 108 may be used to transmit one or more signals 116 to one or more recording units 112.

The operational flow 1300 includes a displaying operation 1330 involving displaying results of the detecting with one or more display units that are operably coupled with the one or more detection units. In some embodiments, one or more display units 110 may be used to display the results of the detecting. In some embodiments, one or more display units 110 may be used to display results in human-readable format. In some embodiments, one or more display units 110 may be used to display results in machine-readable format. In some embodiments, one or more display units 110 may be used to display if one or more nutraceutical associated components are present or absent within one or more samples 102. In some embodiments, one or more display units 110 may be used to display one or more concentrations of one or more nutraceutical associated components 104. In some embodiments, one or more display units 110 may be used to receive one or more signals 116 from one or more detection units 108. In some embodiments, one or more display units 110 may be used to display one or more concentrations of one or more nutraceutical associated components 104 associated with two or more samples 102 that were collected at two or more different times. In some embodiments, one or more display units 110 may be used to display one or more messages indicating one or more dosages of one or more nutraceutical agents for supplementation of an individual. In some embodiments, one or more display units 110 may provide for user interaction. In some embodiments, one or more display units 110 may be used to transmit one or more signals 116 to one or more display units 110. In some embodiments, one or more display units 110 may be used to transmit one or more signals 116 to one or more recording units 112.

Figure 14:
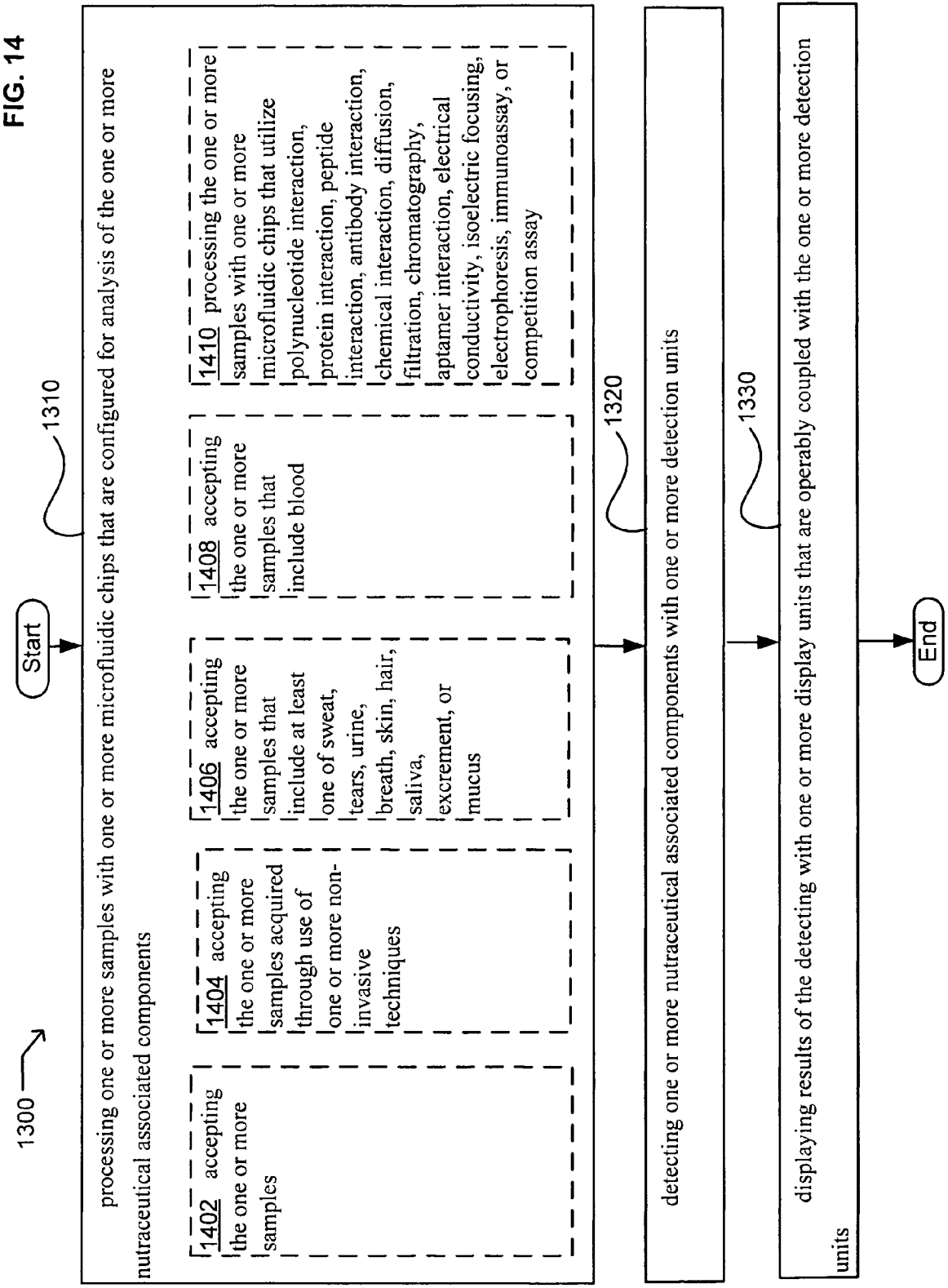
FIG. 14 illustrates alternate embodiments of the example operational flow of FIG. 13.

FIG. 14 illustrates alternative embodiments of the example operational flow 1300 of FIG. 13. FIG. 14 illustrates example embodiments where the processing operation 1310 may include at least one additional operation. Additional operations may include an operation 1402, an operation 1404, an operation 1406, an operation 1408, and/or an operation 1410.

At operation 1402, the processing operation 1310 may include accepting the one or more samples. In some embodiments, one or more microfluidic chips 106 may be configured to accept one or more samples 102. For example, in some embodiments, a microfluidic chip 106 may include a needle to accept one or more blood and/or tissue samples 102. In some embodiments, a microfluidic chip 106 may include a mouthpiece to accept one or more breath and/or saliva samples 102. In some embodiments, a microfluidic chip 106 may include a scraper to accept one or more skin and/or tissue samples 102. Accordingly, in some embodiments, one or more microfluidic chips 106 may accept one or more samples 102. In some embodiments, one or more microfluidic chips 106 may accept one or more samples 102 that are collected through use of invasive techniques. Such techniques include, but are not limited to, drawing blood, obtaining mucus, obtaining tissue samples 102, and the like. In some embodiments, one or more microfluidic chips 106 may accept one or more samples 102 that are collected through use of non-invasive techniques. Such techniques include, but are not limited to, collecting one or more samples 102 that include breath, saliva, hair, sweat, tears, and the like.

In some embodiments, individuals may collect one or more samples 102 from themselves. Accordingly, in some embodiments, system 100 may be used for point-of-care analysis by an individual. In some embodiments, one or more samples 102 may be processed by someone other than the individual from whom the one or more samples 102 were collected. For example, in some embodiments, individuals may collect one or more samples 102 from themselves and then send the one or more samples 102 for analysis by a person other than the individual from whom the samples 102 were collected. In other embodiments, one or more samples 102 may be collected from an individual and analyzed by a person other than the individual. For example, a physician, nurse, coach, nutritionist, personal trainer, or the like may collect one or more samples 102 from an individual and then analyze the one or more samples 102 through use of system 100.

At operation 1404, the processing operation 1310 may include accepting the one or more samples acquired through use of one or more non-invasive techniques. In some embodiments, one or more microfluidic chips 106 may be configured to accept one or more samples 102 that were collected through use of non-invasive techniques. Such techniques include, but are not limited to, collecting one or more samples 102 from an individual that include breath, saliva, hair, sweat, tears, excrement, and the like. For example, in some embodiments, a microfluidic chip 106 may include a mouthpiece to accept breath and/or saliva samples 102. In some embodiments, a microfluidic chip 106 may include a capillary tube to accept fluid samples 102, such as sweat, tears, urine, saliva, and the like. In some embodiments, individuals may collect one or more samples 102 from themselves. Accordingly, in some embodiments, system 100 may be used for point-of-care analysis by an individual. In some embodiments, one or more samples 102 may be analyzed by someone other than the individual from whom the one or more samples 102 were collected. For example, in some embodiments, individuals may collect one or more samples 102 from themselves and then send the one or more samples 102 for analysis by a person other than the individual from whom the samples 102 were collected. In other embodiments, one or more samples 102 may be collected from an individual and analyzed by a person other than the individual. For example, a physician, nurse, coach, nutritionist, personal trainer, or the like may collect one or more samples 102 from an individual and then analyze the one or more samples 102 through use of system 100.

At operation 1406, the processing operation 1310 may include accepting the one or more samples that include at least one of sweat, tears, urine, breath, skin, hair, saliva, excrement, or mucus. In some embodiments, one or more microfluidic chips 106 may accept one or more samples 102 that include at least one of sweat, tears, urine, breath, skin, hair, saliva, excrement, or mucus. In some embodiments, individuals may collect one or more samples 102 from themselves. Accordingly, in some embodiments, system 100 may be used for point-of-care analysis by an individual. In some embodiments, one or more samples 102 may be analyzed by someone other than the individual from whom the one or more samples 102 were collected. For example, in some embodiments, individuals may collect one or more samples 102 from themselves and then send the one or more samples 102 for analysis by a person other than the individual from whom the samples 102 were collected. In other embodiments, one or more samples 102 may be collected from an individual and analyzed by a person other than the individual. For example, a physician, nurse, coach, nutritionist, personal trainer, or the like may collect one or more samples 102 from an individual and then analyze the one or more samples 102 through use of system 100.

At operation 1408, the processing operation 1310 may include accepting the one or more samples that include blood. In some embodiments, one or more microfluidic chips 106 may be configured to accept one or more blood samples 102. For example, in some embodiments, a microfluidic chip 106 may include a needle that may be used to penetrate tissue to accept a blood sample 102. In some embodiments, a microfluidic chip 106 may include a capillary tube that may be used to accept blood for analysis. Such a capillary tube may be used to accept blood for analysis without having to pierce the skin or other tissue of an individual. For example, such a capillary tube may be used to accept a blood sample 102 for analysis by inserting the capillary tube into a blood sample 102 resulting from a finger stick with a lancet.

In some embodiments, individuals may collect one or more blood samples 102 from themselves. Accordingly, in some embodiments, system 100 may be used for point-of-care analysis by an individual. In some embodiments, one or more blood samples 102 may be processed by someone other than the individual from whom the one or more samples 102 were collected. For example, in some embodiments, individuals may collect one or more blood samples 102 from themselves and then send the one or more blood samples 102 for processing by a person other than the individual from whom the samples 102 were collected. In other embodiments, one or more blood samples 102 may be collected from an individual and analyzed by a person other than the individual. For example, a physician, nurse, coach, nutritionist, personal trainer, or the like may collect one or more blood samples 102 from an individual and then analyze the one or more blood samples 102 through use of system 100.

At operation 1410, the processing operation 1310 may include processing the one or more samples with one or more microfluidic chips that utilize polynucleotide interaction, protein interaction, peptide interaction, antibody interaction, chemical interaction, diffusion, filtration, chromatography, aptamer interaction, electrical conductivity, isoelectric focusing, electrophoresis, immunoassay, or competition assay. In some embodiments, one or more microfluidic chips 106 may process one or more samples 102 with at least one technique that includes processing the one or more samples 102 with one or more microfluidic chips 106 that utilize polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof.

In some embodiments, one or more microfluidic chips 106 may process one or more samples 102 utilizing polynucleotide interaction (Singh-Zocchi et al., Proc. Natl. Acad. Sci., 100:7605-7610 (2003) and Wang et al., Anal. Chem., 75:3941-3945 (2003)). Such polynucleotide interaction may occur through hybridization of deoxyribonucleic acid, ribonucleic acid, derivatives thereof, or substantially any combination thereof. In some embodiments, polynucleotides may be configured as polynucleotide arrays. Methods to construct polynucleotide arrays are known and have been used to construct various polynucleotide arrays (Affymetrix, Santa Clara, Calif.).

In some embodiments, one or more microfluidic chips 106 may be configured to process one or more samples 102 through use of competition assays. In some embodiments, a competition assay may utilize a reaction mixture that may include a first fluorescently labeled component that binds to a second fluorescently labeled component. The presence of one or more unlabeled nutraceutical associated components 104 in the reaction mixture decreases the amount of labeled first component and labeled second component that bind to each other and thereby reduces fluorescence resonance energy transfer. Accordingly, detecting the level of fluorescence resonance energy transfer by a detection unit 108 allows the amount of a nutraceutical associated component 104 in a sample 102 to be determined. Numerous other configurations may be prepared that utilize fluorescence resonance energy transfer by one or more detection units 108. In some embodiments, fluorescence quenching may be used within a competition assay. In some embodiments, one or more microfluidic chips 106 may be configured for competition assays where a sample 102 being tested for one or more nutraceutical associated components 104 is mixed with a reaction mixture that includes one or more labeled components that are being tested. The mixed reaction mixture is then passed over a field and/or array to which moieties that bind to the one or more nutraceutical associated components 104 and labeled components are immobilized. The one or more unlabeled nutraceutical associated components 104 in the sample 102 will compete with the one or more labeled components in the reaction mixture for binding and will thereby decrease the amount of label bound within the field and/or array. Accordingly, the amount of one or more nutraceutical associated components 104 being tested for in the sample 102 may be indicated by a decrease in bound label. In some embodiments, such microfluidic chips 106 may include a control field and/or array. In some embodiments, such microfluidic chips 106 may be calibrated prior to application of the sample 102 and therefore not include a control field and/or array. In some embodiments, such fields and/or arrays may include polynucleotides, proteins, peptides, nucleic acid aptamers, peptide aptamers, antibodies, chemicals, chromatographic media, and other materials that may be used to separate one or more nutraceutical associated components 104 from one or more samples 102. Accordingly, fields and/or arrays may include numerous types of moieties that may be used to detect numerous types of nutraceutical associated components 104. In some embodiments, a microfluidic chip 106 may be configured to process one or more samples 102 for one type of nutraceutical associated component 104. In some embodiments, a microfluidic chip 106 may be configured to process one or more samples 102 for one or more types of nutraceutical associated components 104.

In some embodiments, one or more microfluidic chips 106 may be configured to process one or more samples 102 through use of protein interaction. In some embodiments, such interaction may occur through binding interaction. In some embodiments, such interaction may include enzymatic activity. For example, a microfluidic chip 106 may include one or more enzymes that catalyze a reaction that includes nutraceutical associated components 104 as a substrate or as a product. In some embodiments, a nutraceutical associated component 104 may be assayed based on the ability to stimulate an enzyme. In some embodiments, a nutraceutical associated component 104 may be assayed based on the ability to inhibit an enzyme. In some embodiments, such enzyme assays may be colorimetric assays. Accordingly, numerous types of enzyme assays may be adapted for detection of one or more nutraceutical associated components 104.

One or more microfluidic chips 106 may be configured to utilize electrical conductivity to assay one or more nutraceutical associated components 104. Briefly, in some embodiments, one or more microfluidic chips 106 may include electrodes that may be directly coupled to a processor so that the processor may determine the electrical conductivity between electrodes of a particular sensor (U.S. Pat. Nos. 6,958,216 and 7,022,288; herein incorporated by reference).

In some embodiments, one or more microfluidic chips 106 may be configured to utilize isoelectric focusing to process one or more nutraceutical associated components 104 (i.e., U.S. Pat. Nos. 7,074,583; 7,046,357; 6,852,206; 6,849,396; and 7,074,311; herein incorporated by reference). Briefly, isoelectric focusing may be used to characterize nutraceutical associated components 104, such as proteins, based on differences in their isoelectric points. The nutraceutical associated components 104 may then be separated according to their position within a pH gradient.

Numerous chromatographic methods may be used to process one or more nutraceutical associated components 104. Examples of such chromatographic methods include, but are not limited to, gel filtration chromatography, ion-exchange chromatography, affinity chromatography, and the like.

In some embodiments, one or more microfluidic chips 106 may be configured to utilize filtration to process one or more nutraceutical associated components 104. For example, one or more nutraceutical associated components 104 may be processed based on their ability and/or inability to pass through a filter. Such filters may separate nutraceutical associated components 104 based on numerous properties. Examples of such properties include, but are not limited to, molecular weight, charge, hydrophobicity, hydrophilicity, and the like. In some embodiments, one or more microfluidic chips 106 may be configured to use an H-filter to separate one or more nutraceutical associated components 104. Such H-filters have been described (U.S. Pat. Nos. 6,221,677; 6,695,147; 6,541,213; herein incorporated by reference).

In some embodiments, one or more microfluidic chips 106 may be configured to utilize electrophoresis to process one or more nutraceutical associated components 104. Such methods are known in the art (Molecular Cloning: A Laboratory Manual, Cold Spring Harbor Laboratory Press; 3rd edition (Jan. 15, 2001)).

In some embodiments, one or more microfluidic chips 106 may be configured to utilize immunoassay to process one or more nutraceutical associated components 104. Such methods are known in the art (Molecular Cloning: A Laboratory Manual, Cold Spring Harbor Laboratory Press; 3rd edition (Jan. 15, 2001)). Combinations of numerous methods may be used to process one or more nutraceutical associated components 104.

Figure 15:
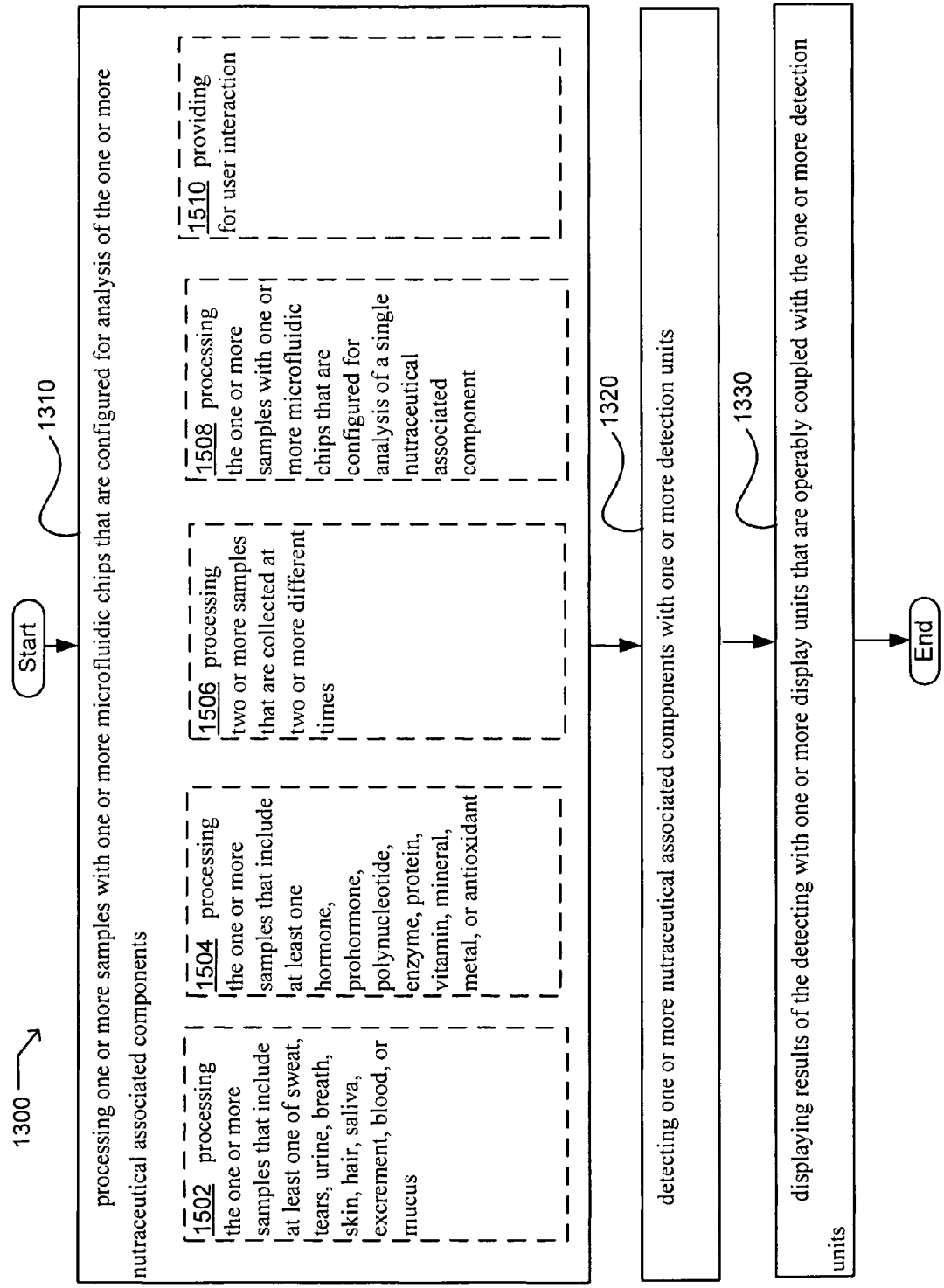
FIG. 15 illustrates alternate embodiments of the example operational flow of FIG. 13.

FIG. 15 illustrates alternative embodiments of the example operational flow 1300 of FIG. 13. FIG. 15 illustrates example embodiments where the processing operation 1310 may include at least one additional operation. Additional operations may include an operation 1502, an operation 1504, an operation 1506, an operation 1508, and/or an operation 1510.

At operation 1502, the processing operation 1310 may include processing the one or more samples that include at least one of sweat, tears, urine, breath, skin, hair, saliva, excrement, blood, or mucus. One or more microfluidic chips 106 may be used to process one or more samples 102 that include at least one of sweat, tears, urine, breath, skin, hair, saliva, excrement, blood, mucus, or substantially any combination thereof. In some embodiments, one or more samples 102 may be processed through use of extraction methods to provide for detection of one or more nutraceutical associated components 104. For example, in some embodiments, nucleic acid may be extracted from a sample 102. In other embodiments, one or more enzymes may be extracted from one or more samples 102. In some embodiments, one or more nutraceutical associated components 104 may be solvent extracted from one or more samples 102. Numerous methods may be used to process one or more samples 102.

At operation 1504, the processing operation 1310 may include processing the one or more samples that include at least one hormone, prohormone, polynucleotide, enzyme, protein, vitamin, mineral, metal, or antioxidant. In some embodiments, one or more microfluidic chips 106 may be used to process one or more samples 102 that include at least one hormone, prohormone, polynucleotide, enzyme, protein, vitamin, mineral, metal, antioxidant, or substantially any combination thereof.

Examples of hormones that may be processed through use of one or more microfluidic chips 106 include, but are not limited to, testosterone (free and/or bound), estrogen, androgens, estradiol, progesterone, melatonin, serotonin, follicle stimulating hormone, dehydroepiandrosterone (DHEA), 5-HTP, cortisol, thyroid stimulating hormone, human chorionic gonadotropin, prohormones thereof, or substantially any combination thereof.

Examples of polynucleotides that may be processed through use of one or more microfluidic chips 106 include, but are not limited to, those that encode hormones, enzymes involved in oxidative pathways, enzymes involved in metabolic pathways, and the like.

Examples of enzymes that may be processed through use of one or more microfluidic chips 106 include, but are not limited to, enzymes involved in oxidative pathways, enzymes involved in metabolic pathways, or substantially any combination thereof.

Examples of proteins that may be processed through use of one or more microfluidic chips 106 include, but are not limited to, proteins linked to urinary tract infection, prostate specific antigen, microalbumin, hemoglobin, or substantially any combination thereof.

Examples of vitamins that may be processed through use of one or more microfluidic chips 106 include, but are not limited to, vitamin A, B vitamins, C vitamins, vitamin D, E vitamins, vitamin K, or substantially any combination thereof.

Examples of minerals that may be processed through use of one or more microfluidic chips 106 include, but are not limited to, calcium, chromium, cobalt, copper, iodine, magnesium, manganese, selenium, strontium, sulfur, zinc, or substantially any combination thereof.

Examples of metals that may be processed through use of one or more microfluidic chips 106 include, but are not limited to, aluminum, antimony, arsenic, bismuth, cadmium, lead, mercury, nickel, tin, or substantially any combination thereof.

Examples of antioxidants that may be processed through use of one or more microfluidic chips 106 include, but are not limited to, vitamin A, vitamin C, vitamin E, alpha lipoic acid, coenzyme Q-10, or substantially any combination thereof.

At operation 1506, the processing operation 1310 may include processing two or more samples that are collected at two or more different times. In some embodiments, one or more microfluidic chips 106 may be used to process two or more samples 102 that are collected at two or more different times. For example, a first sample 102 may be processed that was collected at a first time and a second sample 102 may be processed that was collected at a second time. Numerous samples 102 and time points may be processed through use of microfluidic chips 106. Accordingly, in some embodiments, the presence or absence of one or more nutraceutical associated components 104 at two or more times may be determined. In some embodiments, an increase or decrease in a nutraceutical associated component 104 in a time relevant manner may be determined. Such an increase or decrease in a nutraceutical associated component 104 may be determined through detection of concentration, activity, and the like. Accordingly, system 100 may be used to determine dosages of one or more nutraceutical agents for administration to an individual or group of individuals. In some embodiments, system 100 may be used to determine one or more metabolic responses to one or more nutraceutical agents by an individual or group of individuals.

At operation 1508, the processing operation 1310 may include processing the one or more samples with one or more microfluidic chips that are configured for analysis of a single nutraceutical associated component. In some embodiments, a microfluidic chip 106 may be configured for analysis of a single nutraceutical associated component 104. For example, in some embodiments, a microfluidic chip 106 may be configured for analysis of testosterone in at least one sample 102. In some embodiments, such a microfluidic chip 106 may be configured for analysis of free versus bound testosterone. In some embodiments, a microfluidic chip 106 may be configured for analysis of estrogen in at least one sample 102. Accordingly, microfluidic chips 106 may be configured for analysis of numerous types of nutraceutical associated components 104.

At operation 1510, the processing operation 1310 may include providing for user interaction. In some embodiments, a microfluidic chip 106 may provide for user interaction. For example, in some embodiments, a microfluidic chip 106 may include a receiver that receives signals 116 that are transmitted in response to a user interface 114. Such signals 116 may direct the microfluidic chip 106 to act in accordance with commands input by a user 118. In some embodiments, a microfluidic chip 106 may include one or more user interfaces 114 that provide for direct interaction with a user 118. Examples of such user interfaces 114 include, but are not limited to, ports for accepting samples 102, ports for accepting reagents, electrical connections, couplings, and the like. In some embodiments, electrical connections may be configured for accepting various devices that may be used for numerous purposes, such as to control or monitor a microfluidic chip 106. In some embodiments, couplings may be configured for attachment to syringes, pumps, sample loops, needles, and the like.

Figure 16:
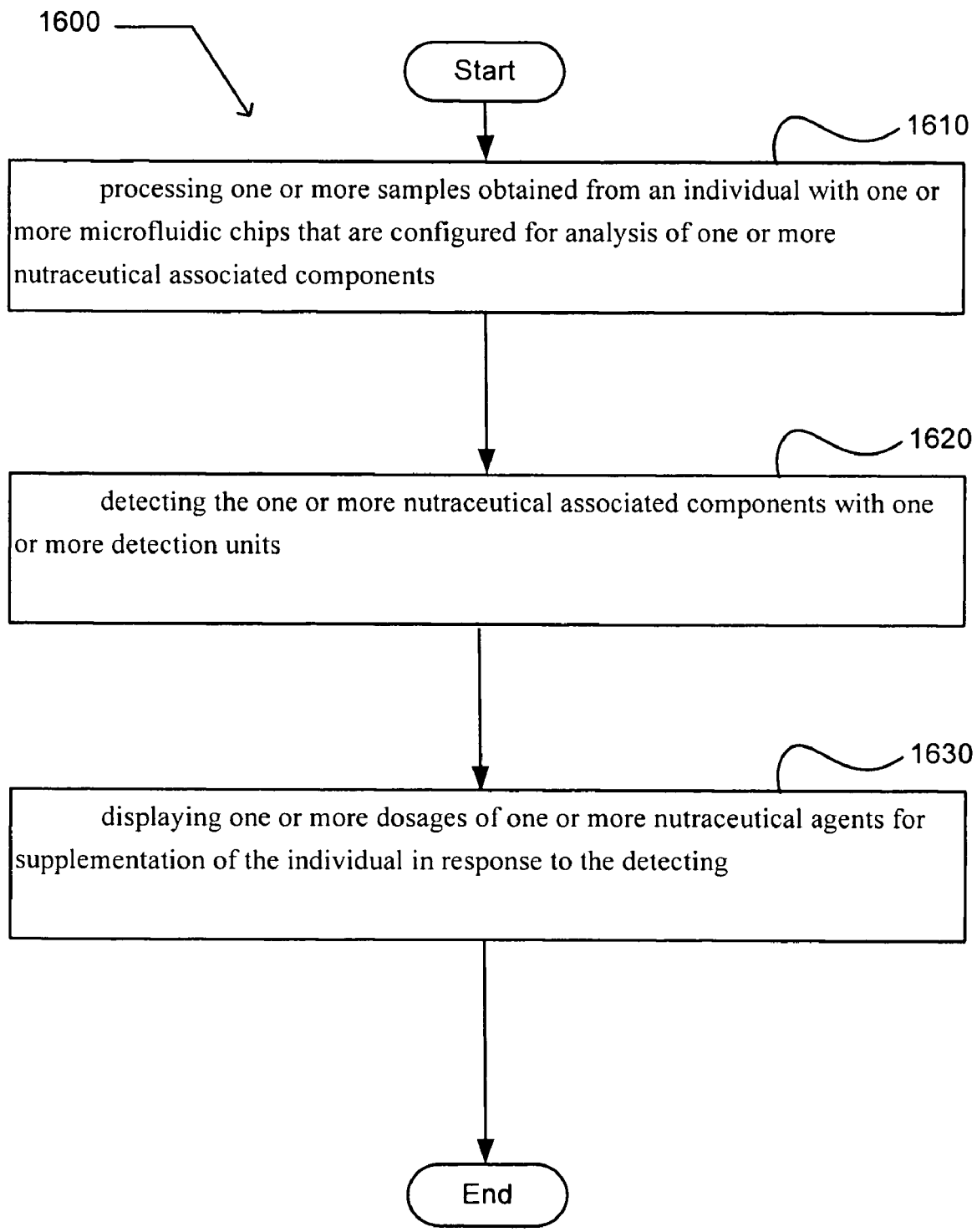
FIG. 16 illustrates an operational flow representing example operations related to methods and systems for analysis of nutraceutical associated components.

FIG. 16 illustrates an operational flow 1600 representing examples of operations that are related to the performance of a method for analysis of one or more nutraceutical associated components 104. In FIG. 16 and in following figures that include various examples of operations used during performance of the method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1600 includes a processing operation 1610 involving processing one or more samples obtained from an individual with one or more microfluidic chips that are configured for analysis of one or more nutraceutical associated components. In some embodiments, one or more microfluidic chips 106 that are configured for analysis of one or more nutraceutical associated components 104 may be used to process one or more samples 102. In some embodiments, one or more microfluidic chips 106 may accept one or more samples 102. In some embodiments, one or more microfluidic chips 106 may accept one or more samples 102 acquired through use of one or more non-invasive techniques. In some embodiments, one or more microfluidic chips 106 may accept one or more samples 102 that include at least one of sweat, tears, urine, breath, skin, hair, saliva, excrement, mucus, or substantially any combination thereof. In some embodiments, one or more microfluidic chips 106 may accept one or more samples 102 that include blood. In some embodiments, one or more microfluidic chips 106 may be used to process one or more samples 102 utilizing polynucleotide interaction, protein interaction, peptide interaction, antibody interaction, chemical interaction, diffusion, filtration, chromatography, aptamer interaction, electrical conductivity, isoelectric focusing, electrophoresis, immunoassay, competition assay, or substantially any combination thereof. In some embodiments, one or more microfluidic chips 106 may be used to process one or more samples 102 that include at least one of sweat, tears, urine, breath, skin, hair, saliva, excrement, blood, mucus, or substantially any combination thereof. In some embodiments, one or more microfluidic chips 106 may be used to process one or more samples 102 that include at least one hormone, prohormone, polynucleotide, enzyme, protein, vitamin, mineral, metal, antioxidant, or substantially any combination thereof. In some embodiments, one or more microfluidic chips 106 may be used to process two or more samples 102 that are collected at two or more different times. In some embodiments, one or more microfluidic chips 106 may be used to process one or more samples 102 that are configured for analysis of a single nutraceutical associated component 104. In some embodiments, one or more microfluidic chips 106 may provide for user interaction.

After a start operation, the operational flow 1600 includes a detecting operation 1620 involving detecting the one or more nutraceutical associated components with one or more detection units. In some embodiments, one or more detection units 108 may be used to detect one or more nutraceutical associated components 104. In some embodiments, one or more detection units 108 may be used to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be used to detect one or more nutraceutical associated components 104 that are associated with two or more samples 102 that were collected at two or more different times. In some embodiments, one or more detection units 108 may provide for user interaction. In some embodiments, one or more detection units 108 may be used to transmit one or more signals 116 to one or more display units 110. In some embodiments, one or more detection units 108 may be used to transmit one or more signals 116 to one or more recording units 112.

After a start operation, the operational flow 1600 includes a displaying operation 1630 involving displaying one or more dosages of one or more nutraceutical agents for supplementation of the individual in response to the detecting. In some embodiments, one or more display units 110 may be used to display one or more dosages of one or more nutraceutical agents for supplementation of the individual in response to the detecting. In some embodiments, one or more display units 110 may be used to display results in human-readable format. In some embodiments, one or more display units 110 may be used to display results in machine-readable format. In some embodiments, one or more display units 110 may be used to display if one or more nutraceutical associated components are present or absent within one or more samples 102. In some embodiments, one or more display units 110 may be used to display one or more concentrations of one or more nutraceutical associated components 104. In some embodiments, one or more display units 110 may be used to receive one or more signals 116 from one or more detection units 108. In some embodiments, one or more display units 110 may be used to display one or more concentrations of one or more nutraceutical associated components 104 associated with two or more samples 102 that were collected at two or more different times. In some embodiments, one or more display units 110 may be used to display one or more messages indicating one or more dosages of one or more nutraceutical agents for supplementation of an individual. In some embodiments, one or more display units 110 may provide for user interaction. In some embodiments, one or more display units 110 may be used to transmit one or more signals 116 to one or more display units 110. In some embodiments, one or more display units 110 may be used to transmit one or more signals 116 to one or more recording units 112.

Figure 17:
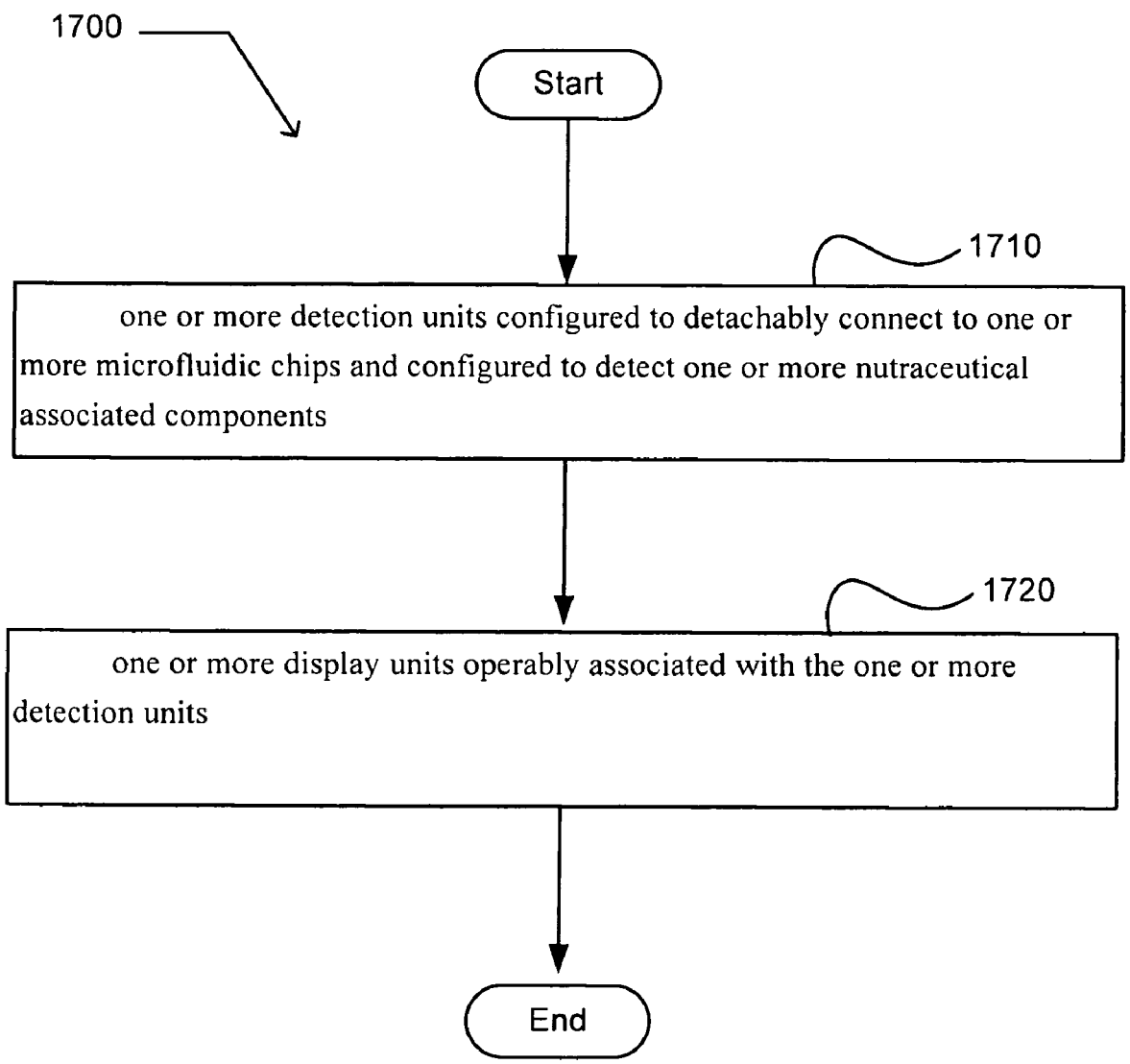
FIG. 17 illustrates an example system 1700 in which embodiments may be implemented.

FIG. 17 illustrates a system 1700 representing examples of modules that may be used to perform a method for analysis of one or more nutraceutical associated components 104. In FIG. 17, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various modules are presented in the sequence(s) illustrated, it should be understood that the various modules may be configured in numerous orientations.

The system 1700 includes module 1710 that includes one or more detection units configured to detachably connect to one or more microfluidic chips and configured to detect one or more nutraceutical associated components. In some embodiments, one or more detection units 108 may be configured to detachably connect to one or more microfluidic chips 106 and configured to detect one or more nutraceutical associated components 104. In some embodiments, one or more detection units 108 may be configured to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be configured to detect one or more nutraceutical associated components 104 associated with two or more samples 102 that were collected at two or more different times. In some embodiments, one or more detection units 108 may include one or more user interfaces 114. In some embodiments, one or more detection units 108 may be configured to transmit one or more signals 116 to one or more display units 110. In some embodiments, one or more detection units 108 may be configured to transmit one or more signals 116 to one or more recording units 112.

The system 1700 includes module 1720 that includes one or more display units operably associated with the one or more detection units. In some embodiments, one or more display units 110 may be configured to operably associate with one or more detection units 108. In some embodiments, one or more display units 110 may be configured to display information in human-readable format. In some embodiments, one or more display units 110 may be configured to display information in machine-readable format. In some embodiments, one or more display units 110 may be configured to display if one or more nutraceutical associated components 104 are present or absent in one or more samples 102. In some embodiments, one or more display units 110 may be configured to display one or more concentrations of the one or more nutraceutical associated components 104. In some embodiments, one or more display units 110 may be configured to receive one or more signals 116 from one or more detection units 108. In some embodiments, one or more display units 110 may be configured to display one or more concentrations of the one or more nutraceutical associated components 104 associated with two or more samples 102 that were collected at two or more different times. In some embodiments, one or more display units 110 may be configured to display one or more messages indicating one or more dosages of one or more nutraceutical agents to supplement an individual with whom the one or more nutraceutical associated components 104 are associated. In some embodiments, one or more display units 110 may include one or more user interfaces 114. In some embodiments, one or more display units 110 may include one or more recording units 112.

Figure 18:
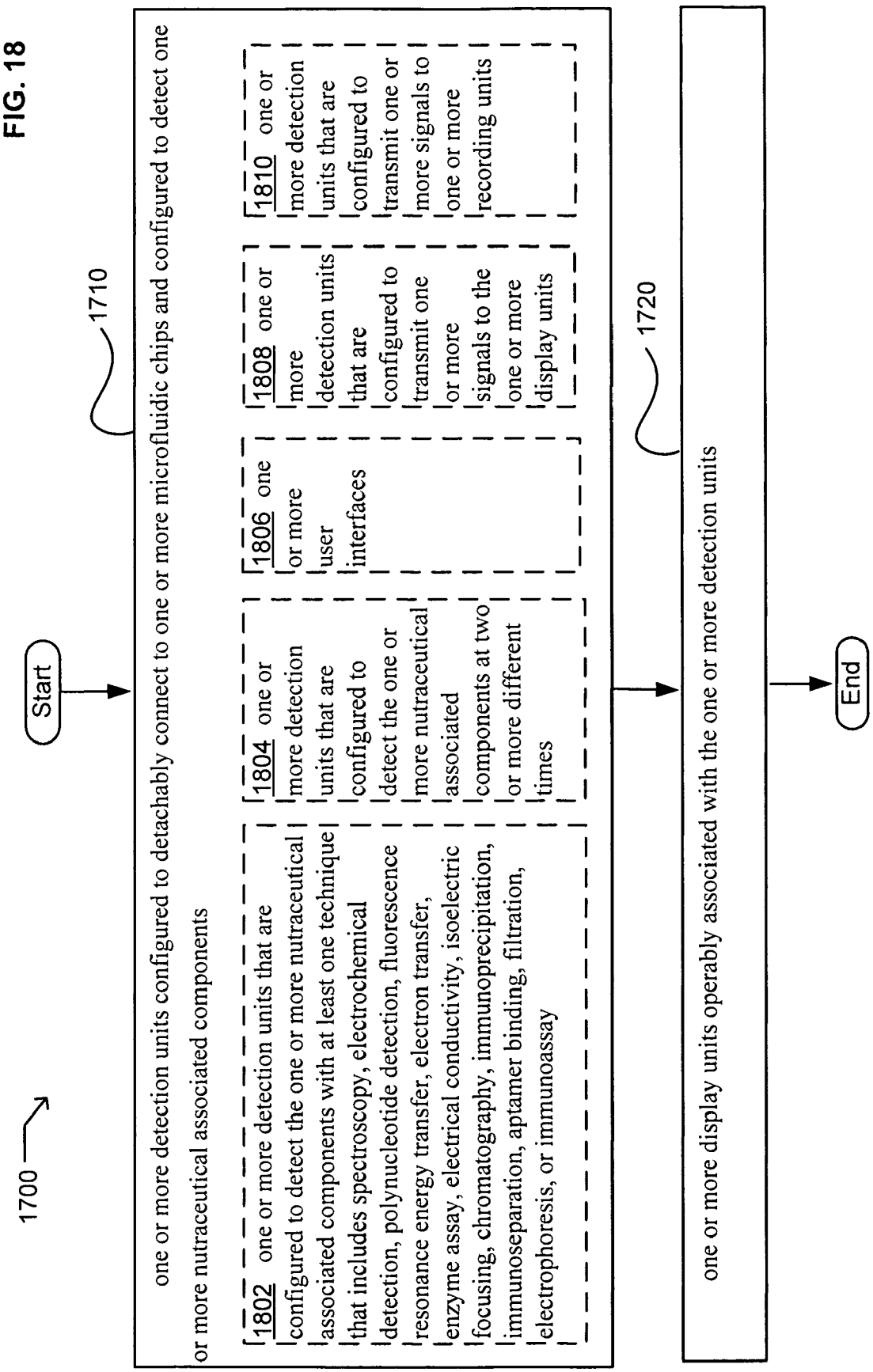
FIG. 18 illustrates alternate embodiments of the system of FIG. 17.

FIG. 18 illustrates alternative embodiments of the system of FIG. 17. FIG. 18 illustrates additional example embodiments of module 1710. Additional embodiments may include embodiment 1802, embodiment 1804, embodiment 1806, embodiment 1808, and/or embodiment 1810.

At embodiment 1802, module 1710 may include one or more detection units that are configured to detect the one or more nutraceutical associated components with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, or immunoassay. In some embodiments, one or more detection units 108 may be configured to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, or immunoassay.

In some embodiments, one or more detection units 108 may be configured to utilize numerous spectroscopic based methods. Examples of such spectroscopic methods include, but are not limited to, mass spectroscopy, atomic absorption spectroscopy, nuclear magnetic resonance spectroscopy, fluorescence spectroscopy, light absorbance, light transmittance, infrared spectroscopy, raman spectroscopy, electron spin resonance, plasmon resonance spectroscopy, ultraviolet light spectroscopy, visible light spectroscopy, and the like.

In some embodiments, one or more detection units 108 may be configured to utilize electrochemical detection. For example, in some embodiments, one or more detection units 108 may be configured to detect conductivity, electromotive force, oxidation potential, reduction potential, redox current, and the like (i.e., Xiao et al., Proc. Natl. Acad. Sci., 103: 16677-16680 (2006) and Fan et al., Proc. Natl. Acad. Sci., 100:9134-9137 (2003)).

In some embodiments, one or more detection units 108 may be configured to detect polynucleotide binding (Singh-Zocchi et al., Proc. Natl. Acad. Sci., 100:7605-7610 (2003) and Wang et al., Anal. Chem., 75:3941-3945 (2003)). Such polynucleotide binding may occur through hybridization of deoxyribonucleic acid, ribonucleic acid, and derivatives thereof.

In some embodiments, one or more detection units 108 may be configured to detect fluorescent resonance energy transfer. For example, one or more detection units 108 may be configured for analysis of one or more nutraceutical associated components 104 through use of competition assays. Such competition assays may utilize a reaction mixture that may include a first fluorescently labeled component that binds to a second fluorescently labeled component. The presence of unlabeled component in the reaction mixture decreases the amount of labeled first component and labeled second component that bind to each other and thereby reduces fluorescence resonance energy transfer. Accordingly, detecting the level of fluorescence resonance energy transfer by a detection unit 108 allows the amount of a component in a sample 102 to be determined. One or more detection units 108 may be prepared having numerous configurations that utilize fluorescence resonance energy transfer.

In some embodiments, one or more detection units 108 may be configured to utilize electron transfer to detect one or more nutraceutical associated components 104 (Fan et al., Proc. Natl. Acad. Sci., 100:9134-9137 (2003)).

One or more detection units 108 may be configured to utilize numerous types of enzyme assays to detect one or more nutraceutical associated components 104. For example, in some embodiments, such enzyme assays may be calorimetric assays. In some embodiments, one or more nutraceutical associated components 104 that stimulate or inhibit the activity of an enzyme may be detected. Accordingly, numerous types of enzyme assays may be adapted for detection of one or more nutraceutical associated components 104.

In some embodiments, one or more detection units 108 may be configured to utilize electrical conductivity to detect one or more nutraceutical associated components 104. Briefly, in some embodiments, electrodes may be directly coupled to a processor so that the processor may determine the electrical conductivity between electrodes of a particular sensor (U.S. Pat. Nos. 6,958,216 and 7,022,288; herein incorporated by reference).

In some embodiments, one or more detection units 108 may be configured to utilize isoelectric focusing to detect one or more nutraceutical associated components 104 (i.e., U.S. Pat. Nos. 7,074,583; 7,046,357; 6,852,206; 6,849,396; and 7,074,311; herein incorporated by reference). Briefly, isoelectric focusing may be used to characterize nutraceutical associated components 104, such as proteins, based on differences in their isoelectric points. The nutraceutical associated components 104 may then be detected according to their position within a pH gradient.

In some embodiments, one or more detection units 108 may be configured to utilize numerous chromatographic methods to detect one or more nutraceutical associated components 104. Examples of such chromatographic methods include, but are not limited to, gel filtration chromatography, ion-exchange chromatography, affinity chromatography, and the like.

In some embodiments, one or more detection units 108 may be configured to utilize immunoseparation to detect one or more nutraceutical associated components 104. Briefly, one or more nutraceutical associated components 104 may be detected upon binding to an antibody or an antibody fragment.

In some embodiments, one or more detection units 108 may be configured to utilize aptamer binding to detect one or more nutraceutical associated components 104. Briefly, one or more nutraceutical associated components 104 may be detected upon binding to an aptamer. Numerous types of aptamers may be utilized to detect nutraceutical associated components 104. Examples of aptamers include, but are not limited to, peptide aptamers and polynucleotide aptamers.

In some embodiments, one or more detection units 108 may be configured to utilize filtration to detect one or more nutraceutical associated components 104. For example, one or more nutraceutical associated components 104 may be detected based on their ability and/or inability to pass through a filter. Such filters may separate nutraceutical associated components 104 based on numerous properties. Examples of such properties include, but are not limited to, molecular weight, charge, hydrophobicity, hydrophilicity, and the like.

In some embodiments, one or more detection units 108 may be configured to utilize electrophoresis to detect one or more nutraceutical associated components 104. Such methods are known in the art (Molecular Cloning: A Laboratory Manual, Cold Spring Harbor Laboratory Press; 3rd edition (Jan. 15, 2001)).

In some embodiments, one or more detection units 108 may be configured to utilize one or more immunoassays to detect one or more nutraceutical associated components 104. Such methods are known in the art (Molecular Cloning: A Laboratory Manual, Cold Spring Harbor Laboratory Press; 3rd edition (Jan. 15, 2001)). In some embodiments, one or more detection units 108 may be configured to utilize combinations of numerous methods to detect one or more nutraceutical associated components 104.

At embodiment 1804, module 1710 may include one or more detection units that are configured to detect the one or more nutraceutical associated components at two or more different times. In some embodiments, one or more detection units 108 may be configured to detect one or more nutraceutical associated components 104 at two or more different times. In some embodiments, two or more samples 102 that include one or more nutraceutical associated components 104 may be collected from an individual at two or more different times and analyzed. Accordingly, changes in the one or more nutraceutical associated components 104 may be followed relative to time. Such changes include, but are not limited to, changes in activity, concentration, and the like. In some embodiments, such changes may occur in response to an event. For example, in some embodiments, one or more nutraceutical associated components 104 may change in response to administration of one or more nutraceutical agents to an individual. In some embodiments, a nutraceutical associated component 104 is a nutraceutical agent. Accordingly, in some embodiments, one or more detection units 108 may be configured to determine the concentration of one or more nutraceutical associated components 104 following administration of one or more nutraceutical agents to an individual. In some embodiments, one or more detection units 108 may be configured to determine the concentration of one or more nutraceutical associated components 104 following an event or stimulus to which an individual is exposed. For example, the concentration and/or activity of one or more nutraceutical agents may be determined during and/or following exercise, food intake, pharmaceutical intake, or ingestion of other substances by an individual. Accordingly, in some embodiments, one or more detection units 108 may be configured to monitor nutraceutical associated components 104 that are affected by an individual's metabolism.

At embodiment 1806, module 1710 may include one or more user interfaces. In some embodiments, one or more detection units 108 may be configured to include one or more user interfaces 114. A detection unit 108 may include numerous types of user interfaces 114. Examples of such user interfaces 114 include, but are not limited to, user interfaces 114 that utilize hardwired methods, such as keyboards, touch screens, personal digital assistant interfaces, telephone interfaces, electronic writing pads, voice recognition interfaces, and the like. User interfaces 114 may also include, but are not limited to, user interfaces 114 that utilize numerous wireless methods, such as use of the internet, mobile telephones, personal digital assistants, and the like. In some embodiments, user interaction may include input of parameters associated with an individual. Examples of such parameters include, but are not limited to, one or more individual's height, weight, age, fat percentage, physical fitness level, known allergies, activities, schedule, pharmaceutical ingestion, nutraceutical ingestion, food ingestion, alcohol consumption, and the like.

At embodiment 1808, module 1710 may include one or more detection units that are configured to transmit one or more signals to the one or more display units. In some embodiments, one or more detection units 108 may be configured to transmit one or more signals 116 to one or more display units 110. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

At embodiment 1810, module 1710 may include one or more detection units that are configured to transmit one or more signals to one or more recording units. In some embodiments, one or more detection units 108 may be configured to transmit one or more signals 116 to one or more recording units 112. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 19:
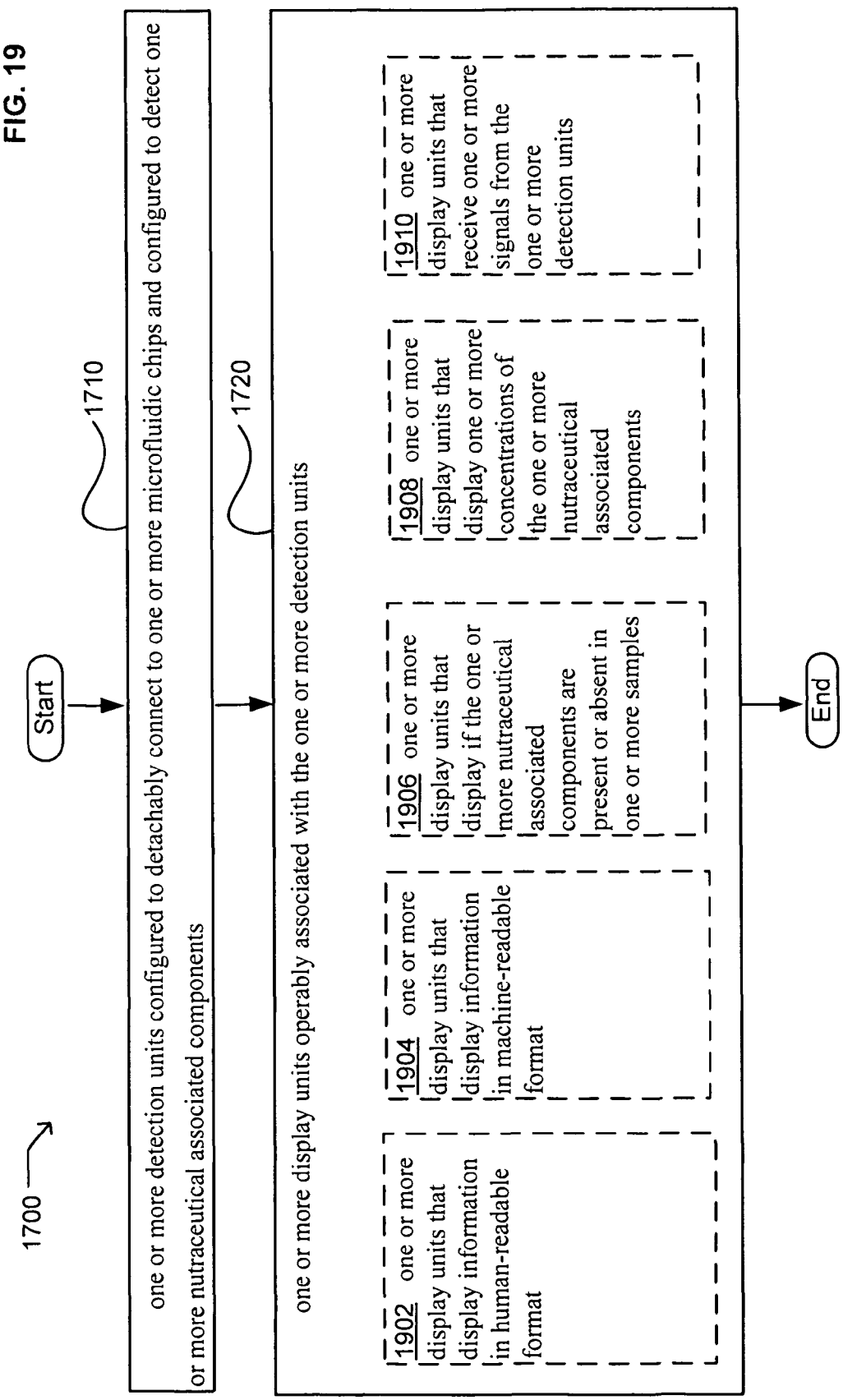
FIG. 19 illustrates alternate embodiments of the system of FIG. 17.

FIG. 19 illustrates alternative embodiments of the system of FIG. 17. FIG. 19 illustrates additional example embodiments of module 1720. Additional embodiments may include embodiment 1902, embodiment 1904, embodiment 1906, embodiment 1908, and/or embodiment 1910.

At embodiment 1902, module 1720 may include one or more display units that display information in human-readable format. In some embodiments, one or more display units 110 may be configured to display one or more results in human-readable format. Examples of human-readable formats include, but are not limited to, written language, verbal communications, Braille output, pictographic output, graphical output, colorographic output, and the like.

At embodiment 1904, module 1720 may include one or more display units that display information in machine-readable format. In some embodiments, one or more display units 110 may be configured to display one or more results in machine-readable format. Examples of machine-readable formats include, but are not limited to, electrical signals 116, bar codes, graphical patterns, punch cards, encoding on a computer-readable medium, magnetic encoding, digital coding, optical coding, and the like.

At embodiment 1906, module 1720 may include one or more display units that display if the one or more nutraceutical associated components are present or absent in one or more samples. In some embodiments, one or more display units 110 may be configured to display if one or more nutraceutical associated components 104 are present or absent within one or more samples 102. In some embodiments, one or more display units 110 may be configured to display the identity of one or more nutraceutical associated components 104 that are present or absent within one or more samples 102. For example, in some embodiments, one or more display units 110 may be configured to display if one or more nutraceutical associated components 104, such as one or more nutraceutical agents, are present or absent from one or more food supplements, foods, bodily samples 102, and the like.

At embodiment 1908, module 1720 may include one or more display units that display one or more concentrations of the one or more nutraceutical associated components. In some embodiments, one or more display units 110 may be configured to display one or more concentrations of one or more nutraceutical associated components 104 that are present or absent within one or more samples 102. Concentrations of one or more nutraceutical associated components 104 may be displayed in numerous formats. For example, in some embodiments, concentration may be expressed in quantity terms that include, but are not limited to, grams, milligrams, nanograms, and the like. In some embodiments, concentrations may be expressed in quantity per volume of sample 102. For example, in some embodiments, concentration may be expressed as molarity, molality, grams per liter, milligrams per liter, milligrams per deciliter, and the like.

At embodiment 1910, module 1720 may include one or more display units that receive one or more signals from the one or more detection units. In some embodiments, one or more display units 110 may be configured to receive one or more signals 116 from one or more detection units 108. Examples of such signals 116 include, but are not limited to, hardwired signals 116, wireless signals 116, infrared signals 116, optical signals 116, radiofrequency (RF) signals 116, audible signals 116, digital signals 116, analog signals 116, or substantially any combination thereof.

Figure 20:
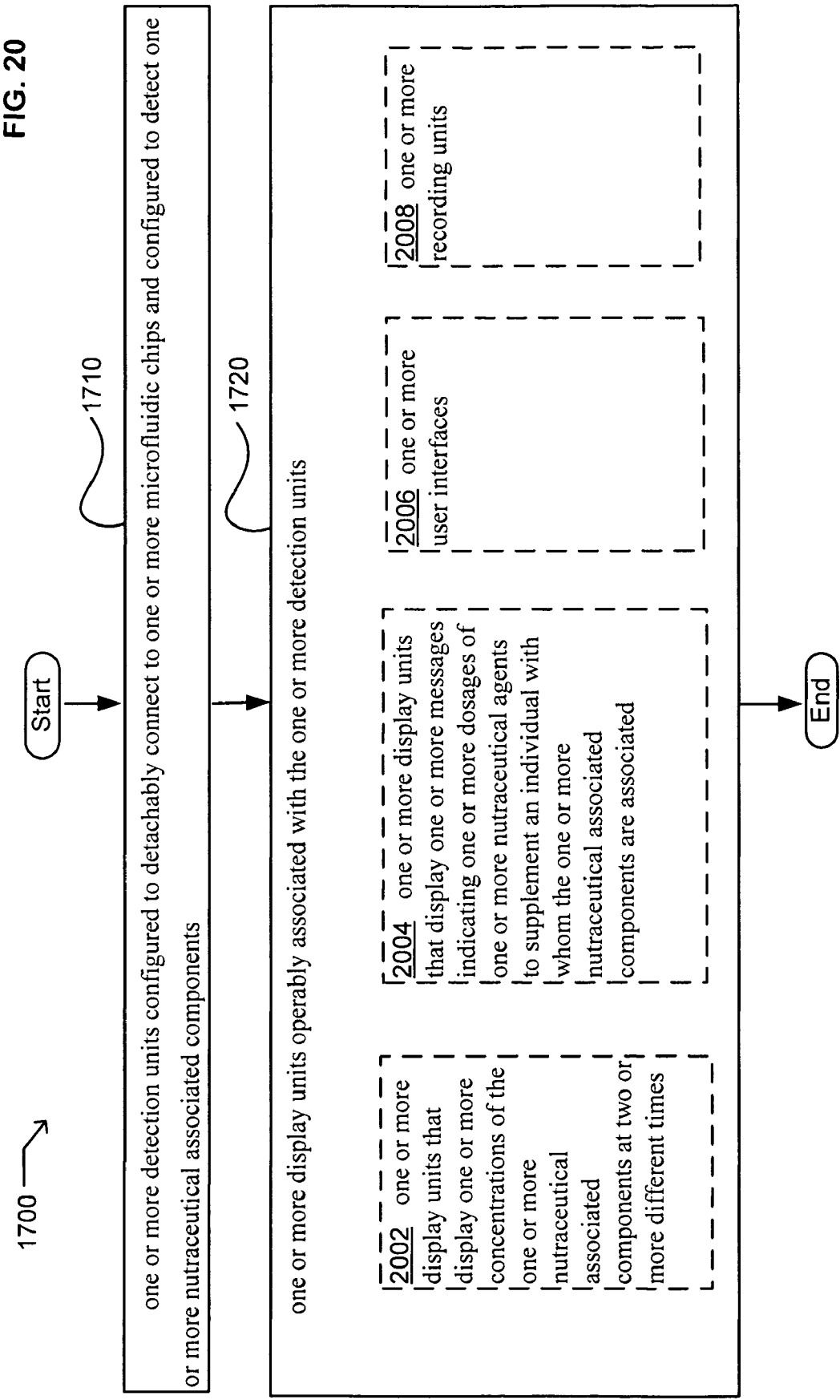
FIG. 20 illustrates alternate embodiments of the system of FIG. 17.

FIG. 20 illustrates alternative embodiments of the system of FIG. 17. FIG. 20 illustrates additional example embodiments of module 1720. Additional embodiments may include embodiment 2002, embodiment 2004, embodiment 2006, and/or embodiment 2008.

At embodiment 2002, module 1720 may include one or more display units that display one or more concentrations of the one or more nutraceutical associated components at two or more different times. In some embodiments, one or more display units 110 may be configured to display one or more concentrations of one or more nutraceutical associated components 104 at two or more different times. In some embodiments, one or more display units 110 may be configured to display one or more concentrations of one or more nutraceutical associated components 104 present within two or more samples 102 that were collected at two or more different times. In some embodiments, one or more display units 110 may be configured to display two or more concentrations of one or more nutraceutical associated components 104 in graphical form. For example, in some embodiments, concentrations may be displayed as a bar graph, a line graph, a pie chart, and the like. Accordingly, in some embodiments, one or more display units 110 may be configured to plot two or more concentrations of one or more nutraceutical associated components 104. Numerous plot formats may be used. Examples of such formats include, but are not limited to, concentration versus time from ingestion of one or more nutraceutical agents, concentration versus time from an event, such as exercise, sleep, injury, and the like. Accordingly, in some embodiments, one or more display units 110 may be configured to display one or more concentrations of one or more nutraceutical agents within a sample 102 obtained from an individual at one or more times. For example, in some embodiments, one or more display units 110 may display the concentration of one or more nutraceutical associated components 104 in blood samples 102 obtained from an individual following ingestion of one or more nutraceutical agents.

At embodiment 2004, module 1720 may include one or more display units that display one or more messages indicating one or more dosages of one or more nutraceutical agents to supplement an individual with whom the one or more nutraceutical associated components are associated. In some embodiments, one or more display units 110 may be configured to display one or more messages indicating one or more dosages of one or more nutraceutical agents for supplementation of an individual. In some embodiments, one or more display units 110 may be configured to display one or more concentrations of one or more nutraceutical associated components 104 included within one or more samples 102 obtained from an individual and then display one or more concentrations of one or more nutraceutical agents for supplementation of the individual. For example, in some embodiments, the concentration of calcium may be determined to be low in a sample 102 obtained from an individual and the display unit 110 may be configured to indicate a dosage of a calcium supplement for administration to the individual. Accordingly, one or more display units 110 may be configured to display one or more dosages of numerous types of nutraceutical agents for administration to one or more individuals.

At embodiment 2006, module 1720 may include one or more user interfaces. In some embodiments, one or more display units 110 may be configured to provide for user interaction. In some embodiments, one or more display units 110 may include one or more user interfaces 114. A display unit 110 may include numerous types of user interfaces 114. Examples of such user interfaces 114 include, but are not limited to, user interfaces 114 that utilize hardwired methods, such as keyboards, touch screens, personal digital assistant interfaces, telephone interfaces, electronic writing pads, voice recognition interfaces, and the like. User interfaces 114 may also include, but are not limited to, user interfaces 114 that utilize numerous wireless methods, such as use of the internet, mobile telephones, personal digital assistants, and the like. In some embodiments, user interaction may include input of parameters associated with an individual. Examples of such parameters include, but are not limited to, one or more individual's height, weight, age, fat percentage, physical fitness level, known allergies, activities, schedule, pharmaceutical ingestion, nutraceutical ingestion, food ingestion, alcohol consumption, and the like.

At embodiment 2008, module 1720 may include one or more recording units. In some embodiments, one or more display units 110 may be configured to include one or more recording units 112.

Figure 21:
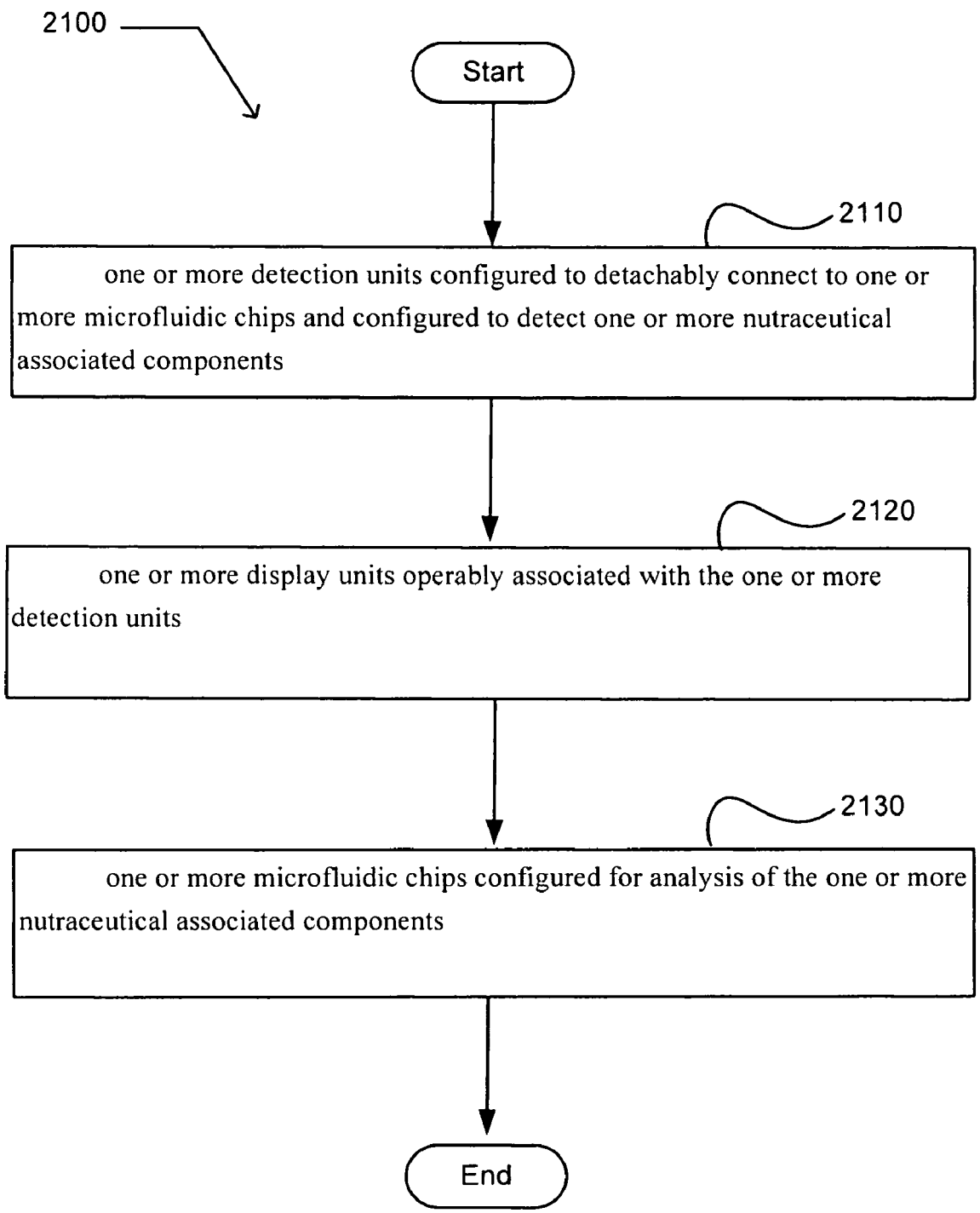
FIG. 21 illustrates an example system 2100 in which embodiments may be implemented.

FIG. 21 illustrates a system 2100 representing examples of modules that may be used to perform a method for analysis of one or more nutraceutical associated components 104. In FIG. 21, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various modules are presented in the sequence(s) illustrated, it should be understood that the various modules may be configured in numerous orientations.

The system 2100 includes module 2110 that includes one or more detection units configured to detachably connect to one or more microfluidic chips and configured to detect one or more nutraceutical associated components. In some embodiments, one or more detection units 108 may be configured to detachably connect to one or more microfluidic chips 106 and configured to detect one or more nutraceutical associated components 104. In some embodiments, one or more detection units 108 may be configured to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be configured to detect one or more nutraceutical associated components 104 associated with two or more samples 102 that were collected at two or more different times. In some embodiments, one or more detection units 108 may include one or more user interfaces 114. In some embodiments, one or more detection units 108 may be configured to transmit one or more signals 116 to one or more display units 110. In some embodiments, one or more detection units 108 may be configured to transmit one or more signals 116 to one or more recording units 112.

The system 2100 includes module 2120 that includes one or more display units operably associated with the one or more detection units. In some embodiments, one or more display units 110 may be configured to operably associate with one or more detection units 108. In some embodiments, one or more display units 110 may be configured to display information in human-readable format. In some embodiments, one or more display units 110 may be configured to display information in machine-readable format. In some embodiments, one or more display units 110 may be configured to display if one or more nutraceutical associated components 104 are present or absent in one or more samples 102. In some embodiments, one or more display units 110 may be configured to display one or more concentrations of the one or more nutraceutical associated components 104. In some embodiments, one or more display units 110 may be configured to receive one or more signals 116 from one or more detection units 108. In some embodiments, one or more display units 110 may be configured to display one or more concentrations of the one or more nutraceutical associated components 104 associated with two or more samples 102 that were collected at two or more different times. In some embodiments, one or more display units 110 may be configured to display one or more messages indicating one or more dosages of one or more nutraceutical agents to supplement an individual with whom the one or more nutraceutical associated components 104 are associated. In some embodiments, one or more display units 110 may include one or more user interfaces 114. In some embodiments, one or more display units 110 may include one or more recording units 112.

The system 2100 may optionally include module 2130 that includes one or more microfluidic chips configured for analysis of the one or more nutraceutical associated components. In some embodiments, one or more microfluidic chips 106 may be configured for analysis of one or more nutraceutical associated components 104. In some embodiments, one or more microfluidic chips 106 may be configured for accepting one or more samples 102. In some embodiments, one or more microfluidic chips 106 may be configured for accepting one or more samples 102 that include blood. In some embodiments, one or more microfluidic chips 106 may be configured for accepting one or more samples 102 that include at least one of sweat, tears, urine, breath, skin, hair, saliva, excrement, mucus, or substantially any combination thereof. In some embodiments, one or more microfluidic chips 106 may be configured for analysis of one or more samples 102 that include at least one of blood, sweat, tears, urine, breath, skin, hair, saliva, excrement, mucus, or substantially any combination thereof. In some embodiments, one or more microfluidic chips 106 may be configured for analysis of one or more nutraceutical associated components 104 that include at least one hormone, prohormone, polynucleotide, enzyme, protein, vitamin, mineral, metal, antioxidants, or substantially any combination thereof. In some embodiments, one or more microfluidic chips 106 may be configured for analysis of one or more nutraceutical associated components 104 associated with two or more samples 102 that were collected at two or more different times. In some embodiments, one or more microfluidic chips 106 may be configured for analysis of a single nutraceutical associated component 104.

Figure 22:
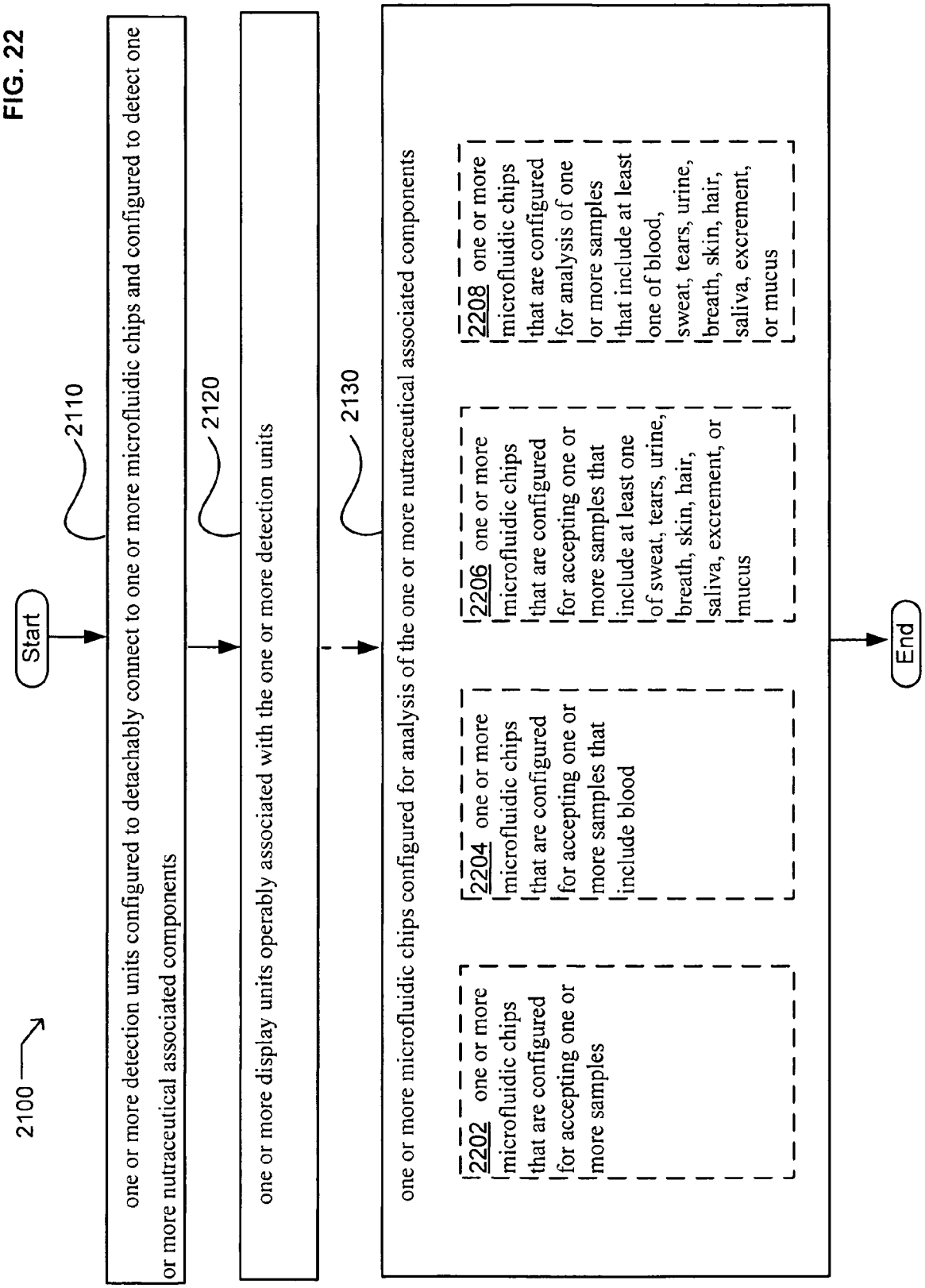
FIG. 22 illustrates alternate embodiments of the system of FIG. 21.

FIG. 22 illustrates alternative embodiments of the system of FIG. 21. FIG. 22 illustrates additional example embodiments of module 2130. Additional embodiments may include embodiment 2202, embodiment 2204, embodiment 2206, and/or embodiment 2208.

At embodiment 2202, module 2130 may include one or more microfluidic chips that are configured for accepting one or more samples. In some embodiments, one or more microfluidic chips 106 may be configured to accept one or more samples 102. For example, in some embodiments, a microfluidic chip 106 may include a needle to accept one or more blood and/or tissue samples 102 from an individual. In some embodiments, a microfluidic chip 106 may include a mouthpiece to accept one or more breath and/or saliva samples 102 from an individual. In some embodiments, a microfluidic chip 106 may include a scraper to accept one or more skin and/or tissue samples 102 from an individual. Accordingly, in some embodiments, one or more microfluidic chips 106 may be configured to accept one or more samples 102. In some embodiments, one or more microfluidic chips 106 may be configured to accept one or more samples 102 that are collected through use of invasive techniques. Such techniques include, but are not limited to, drawing blood, obtaining mucus, obtaining tissue samples 102, and the like. In some embodiments, one or more microfluidic chips 106 may be configured to accept one or more samples 102 that are collected through use of non-invasive techniques. Such techniques include, but are not limited to, collecting one or more samples 102 that include breath, saliva, hair, sweat, tears, and the like.

At embodiment 2204, module 2130 may include one or more microfluidic chips that are configured for accepting one or more samples that include blood. In some embodiments, one or more microfluidic chips 106 may be configured to accept one or more blood samples 102. For example, in some embodiments, a microfluidic chip 106 may include a needle that may be used to penetrate tissue to accept a blood sample 102. In some embodiments, a microfluidic chip 106 may include a capillary tube that may be used to accept blood for analysis. Such a capillary tube may be used to accept blood for analysis without having to pierce the skin or other tissue of an individual. For example, such a capillary tube may be used to accept a blood sample 102 for analysis by inserting the capillary tube into a blood sample 102 resulting from a finger stick with a lancet.

At embodiment 2206, module 2130 may include one or more microfluidic chips that are configured for accepting one or more samples that include at least one of sweat, tears, urine, breath, skin, hair, saliva, excrement, or mucus. In some embodiments, one or more microfluidic chips 106 may be configured to accept one or more samples 102 that include at least one of sweat, tears, urine, breath, skin, hair, saliva, excrement, or mucus. In some embodiments, one or more microfluidic chips 106 may be configured to allow individuals to collect one or more samples 102 from themselves. Accordingly, in some embodiments, a microfluidic chip 106 may be used for point-of-care analysis by an individual. In some embodiments, one or more microfluidic chips 106 may be configured to allow one or more samples 102 to be analyzed by someone other than the individual from whom the one or more samples 102 were collected. For example, in some embodiments, one or more microfluidic chips 106 may be configured so that individuals may collect one or more samples 102 from themselves and then send the one or more samples 102 for analysis by a person other than the individual from whom the samples 102 were collected. In other embodiments, one or more microfluidic chips 106 may be configured so that one or more samples 102 may be collected from an individual and analyzed by a person other than the individual. For example, a physician, nurse, coach, nutritionist, personal trainer, or the like may collect one or more samples 102 from an individual and then analyze the one or more samples 102.

At embodiment 2208, module 2130 may include one or more microfluidic chips that are configured for analysis of one or more samples that include at least one of blood, sweat, tears, urine, breath, skin, hair, saliva, excrement, or mucus. One or more microfluidic chips 106 may be configured for analysis of one or more samples 102 that include at least one of sweat, tears, urine, breath, skin, hair, saliva, excrement, blood, mucus, or substantially any combination thereof. In some embodiments, one or more samples 102 may be processed through use of extraction methods to provide for detection of one or more nutraceutical associated components 104. For example, in some embodiments, nucleic acid may be extracted from a sample 102. In other embodiments, one or more enzymes may be extracted from one or more samples 102. In some embodiments, one or more nutraceutical associated components 104 may be solvent extracted from one or more samples 102. Numerous methods may be used to process one or more samples 102.

Figure 23:
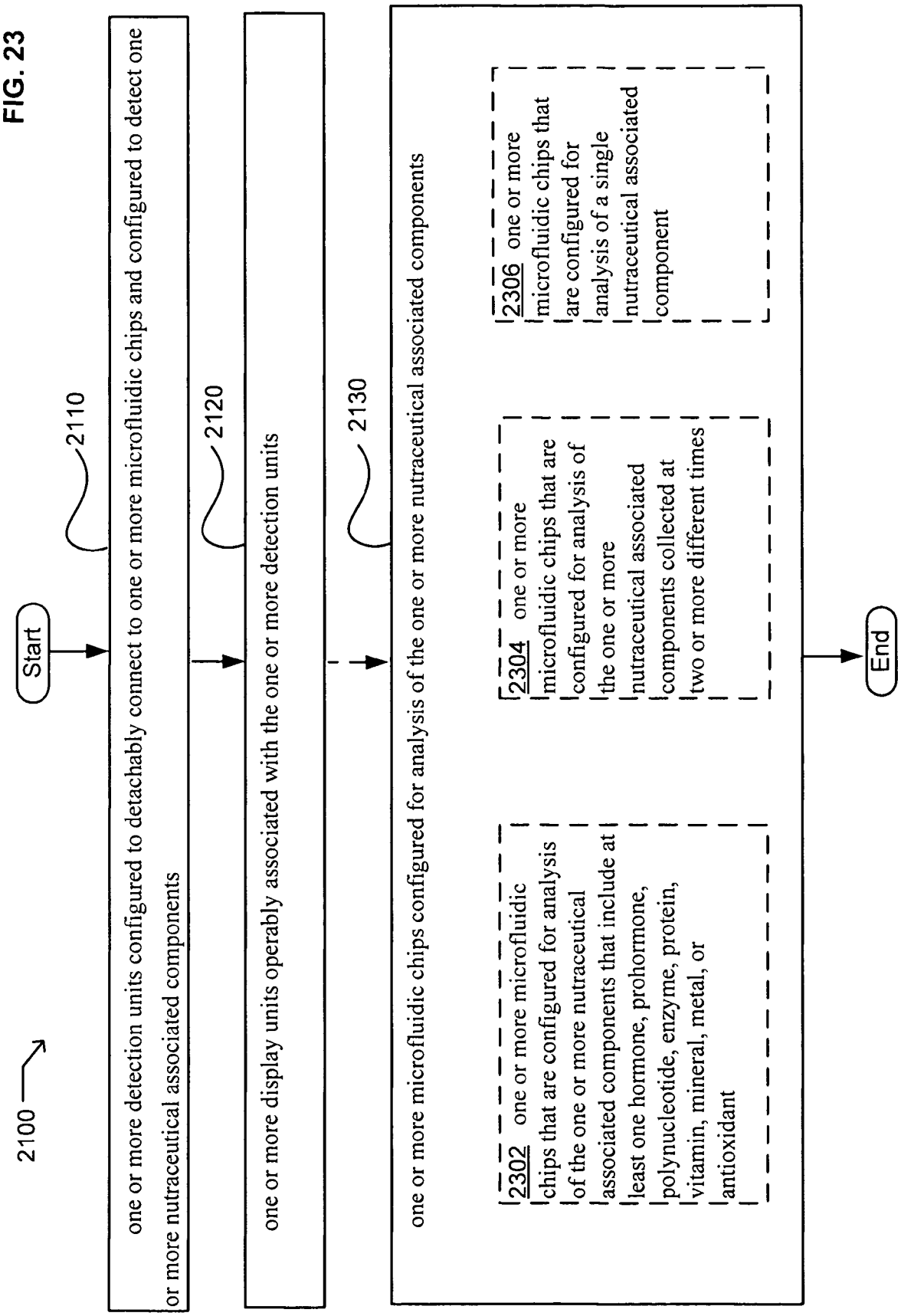
FIG. 23 illustrates alternate embodiments of the system of FIG. 21.

FIG. 23 illustrates alternative embodiments of the system of FIG. 21. FIG. 23 illustrates additional example embodiments of module 2130. Additional embodiments may include embodiment 2302, embodiment 2304, and/or embodiment 2306.

At embodiment 2302, module 2130 may include one or more microfluidic chips that are configured for analysis of the one or more nutraceutical associated components that include at least one hormone, prohormone, polynucleotide, enzyme, protein, vitamin, mineral, metal, or antioxidant. In some embodiments, one or more microfluidic chips 106 may be configured for analysis of one or more nutraceutical associated components 104 that include at least one hormone, prohormone, polynucleotide, enzyme, protein, vitamin, mineral, metal, or antioxidant.

Examples of hormones that may be processed through use of one or more microfluidic chips 106 include, but are not limited to, testosterone (free and/or bound), estrogen, androgens, estradiol, progesterone, melatonin, serotonin, follicle stimulating hormone, dehydroepiandrosterone (DHEA), 5-HTP, cortisol, thyroid stimulating hormone, human chorionic gonadotropin, prohormones thereof, or substantially any combination thereof.

Examples of polynucleotides that may be processed through use of one or more microfluidic chips 106 include, but are not limited to, those that encode hormones, enzymes involved in oxidative pathways, enzymes involved in metabolic pathways, and the like.

Examples of enzymes that may be processed through use of one or more microfluidic chips 106 include, but are not limited to, enzymes involved in oxidative pathways, enzymes involved in metabolic pathways, or substantially any combination thereof.

Examples of proteins that may be processed through use of one or more microfluidic chips 106 include, but are not limited to, proteins linked to urinary tract infection, prostate specific antigen, microalbumin, hemoglobin, or substantially any combination thereof.

Examples of vitamins that may be processed through use of one or more microfluidic chips 106 include, but are not limited to, vitamin A, B vitamins, C vitamins, vitamin D, E vitamins, vitamin K, or substantially any combination thereof.

Examples of minerals that may be processed through use of one or more microfluidic chips 106 include, but are not limited to, calcium, chromium, cobalt, copper, iodine, magnesium, manganese, selenium, strontium, sulfur, zinc, or substantially any combination thereof.

Examples of metals that may be processed through use of one or more microfluidic chips 106 include, but are not limited to, aluminum, antimony, arsenic, bismuth, cadmium, lead, mercury, nickel, tin, or substantially any combination thereof.

Examples of antioxidants that may be processed through use of one or more microfluidic chips 106 include, but are not limited to, vitamin A, vitamin C, vitamin E, alpha lipoic acid, coenzyme Q-10, or substantially any combination thereof.

At embodiment 2304, module 2130 may include one or more microfluidic chips that are configured for analysis of the one or more nutraceutical associated components collected at two or more different times. In some embodiments, one or more microfluidic chips 106 may be configured for analysis of two or more samples 102 that are collected at two or more different times. For example, a first sample 102 may be analyzed that was collected at a first time and a second sample 102 may be analyzed that was collected at a second time. Numerous samples 102 and time points may be analyzed through use of microfluidic chips 106. Accordingly, in some embodiments, the presence or absence of one or more nutraceutical associated components 104 at two or more times may be determined. In some embodiments, an increase or decrease in a nutraceutical associated component 104 in a time relevant manner may be determined. Such an increase or decrease in a nutraceutical associated component 104 may be determined through detection of concentration, activity, and the like.

At embodiment 2306, module 2130 may include one or more microfluidic chips that are configured for analysis of a single nutraceutical associated component. In some embodiments, a microfluidic chip 106 may be configured for analysis of a single nutraceutical associated component 104. For example, in some embodiments, a microfluidic chip 106 may be configured for analysis of testosterone in at least one sample 102. In some embodiments, such a microfluidic chip 106 may be configured for analysis of free versus bound testosterone. In some embodiments, a microfluidic chip 106 may be configured for analysis of estrogen in at least one sample 102. Accordingly, microfluidic chips 106 may be configured for analysis of numerous types of nutraceutical associated components 104.

Figure 24:
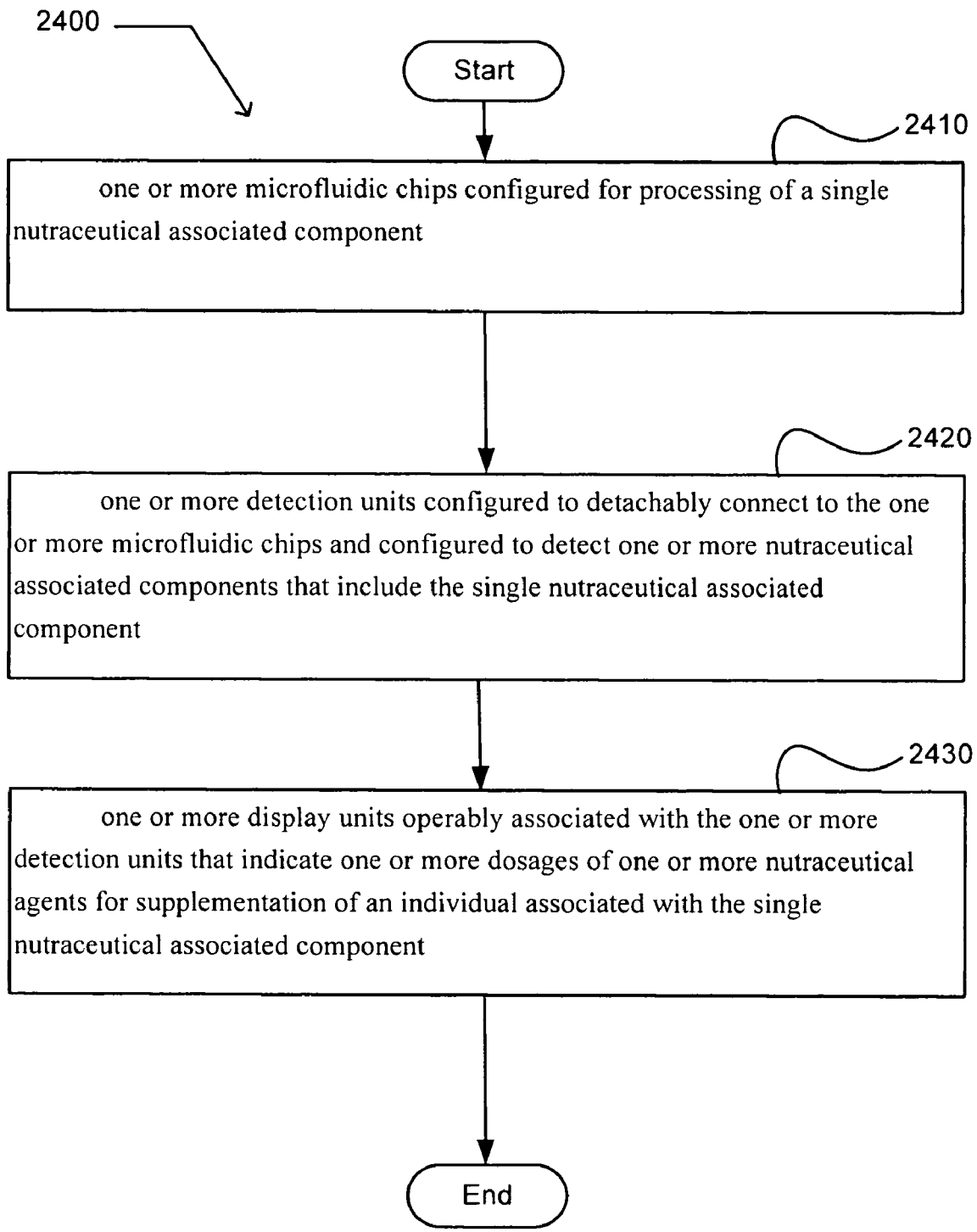
FIG. 24 illustrates an example system 2400 in which embodiments may be implemented.

FIG. 24 illustrates a system 2400 representing examples of modules that may be used to perform a method for analysis of one or more nutraceutical associated components 104. In FIG. 24, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various modules are presented in the sequence(s) illustrated, it should be understood that the various modules may be configured in numerous orientations.

The system 2400 includes module 2410 that includes one or more microfluidic chips configured for processing of a single nutraceutical associated component. In some embodiments, one or more microfluidic chips 106 may be configured for processing of a single nutraceutical associated component 104. In some embodiments, one or more microfluidic chips 106 may be configured for accepting one or more samples 102. In some embodiments, one or more microfluidic chips 106 may be configured for accepting one or more samples 102 that include blood. In some embodiments, one or more microfluidic chips 106 may be configured for accepting one or more samples 102 that include at least one of sweat, tears, urine, breath, skin, hair, saliva, excrement, mucus, or substantially any combination thereof. In some embodiments, one or more microfluidic chips 106 may be configured for analysis of one or more samples 102 that include at least one of blood, sweat, tears, urine, breath, skin, hair, saliva, excrement, mucus, or substantially any combination thereof. In some embodiments, one or more microfluidic chips 106 may be configured for analysis of a single nutraceutical associated component 104 that may include a hormone, prohormone, polynucleotide, enzyme, protein, vitamin, mineral, metal, or antioxidant. In some embodiments, one or more microfluidic chips 106 may be configured for analysis of a single nutraceutical associated component 104 associated with two or more samples 102 that were collected at two or more different times.

The system 2400 includes module 2420 that includes one or more detection units configured to detachably connect to the one or more microfluidic chips and configured to detect one or more nutraceutical associated components that include the single nutraceutical associated component. In some embodiments, one or more detection units 108 may be configured to detachably connect to one or more microfluidic chips 106 and configured to detect one or more nutraceutical associated components 104 that include the single nutraceutical associated component 104. In some embodiments, one or more detection units 108 may be configured to detect one or more nutraceutical associated components 104 with at least one technique that includes spectroscopy, electrochemical detection, polynucleotide detection, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or substantially any combination thereof. In some embodiments, one or more detection units 108 may be configured to detect one or more nutraceutical associated components 104 associated with two or more samples 102 that were collected at two or more different times. In some embodiments, one or more detection units 108 may include one or more user interfaces 114. In some embodiments, one or more detection units 108 may be configured to transmit one or more signals 116 to one or more display units 110. In some embodiments, one or more detection units 108 may be configured to transmit one or more signals 116 to one or more recording units 112.

The system 2400 includes module 2430 that includes one or more display units operably associated with the one or more detection units that indicate one or more dosages of one or more nutraceutical agents for supplementation of an individual associated with the single nutraceutical associated component. In some embodiments, one or more display units 110 may be configured to operably associate with one or more detection units 108 that indicate one or more dosages of one or more nutraceutical agents for supplementation of an individual associated with the single nutraceutical associated component 104. In some embodiments, one or more display units 110 may be configured to display information in human-readable format. In some embodiments, one or more display units 110 may be configured to display information in machine-readable format. In some embodiments, one or more display units 110 may be configured to display if one or more nutraceutical associated components 104 are present or absent in one or more samples 102. In some embodiments, one or more display units 110 may be configured to display one or more concentrations of the one or more nutraceutical associated components 104. In some embodiments, one or more display units 110 may be configured to receive one or more signals 116 from one or more detection units 108. In some embodiments, one or more display units 110 may be configured to display one or more concentrations of one or more nutraceutical associated components 104 associated with two or more samples 102 that were collected at two or more different times. In some embodiments, one or more display units 110 may be configured to display one or more messages indicating one or more dosages of one or more nutraceutical agents to supplement an individual with whom the single nutraceutical associated component 104 is associated. In some embodiments, one or more display units 110 may include one or more user interfaces 114. In some embodiments, one or more display units 110 may include one or more recording units 112.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity. While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include, but are not limited to, a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof. Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

Although a user 118 is shown/described herein as a single illustrated figure, those skilled in the art will appreciate that a user 118 may be representative of a human user 118, a robotic user 118 (e.g., computational entity), and/or substantially any combination thereof (e.g., a user 118 may be assisted by one or more robotic agents). In addition, a user 118 as set forth herein, although shown as a single entity may in fact be composed of two or more entities. Those skilled in the art will appreciate that, in general, the same may be said of "sender" and/or other entity-oriented terms as such terms are used herein. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to, physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A method comprising:
   receiving one or more parameters of an individual including at least one behavioral, characteristic, and/or appearance related parameter;
   receiving two or more samples of the individual collected at two or more different times, the two or more samples including at least one of urine, saliva, and/or blood;
   assaying using one or more microfluidic chips the two or more samples to detect at least one amount of testosterone of each sample;
   determining one or more testosterone amount changes over time using the at least one amount of testosterone of each sample; and
   identifying, based upon one or more potential relationships of the one or more testosterone amount changes and the one or more parameters, one or more dosages and/or one or more dosage modifications of one or more non-pharmaceutically regulated nutraceutical agents for supplementation of the individual.

2. The method of claim 1, wherein the receiving one or more parameters of an individual including at least one behavioral, characteristic, and/or appearance related parameter comprises:
   receiving via one or more user interfaces one or more parameters of an individual including at least one behavioral, characteristic, and/or appearance related parameter.

3. The method of claim 1, wherein the receiving two or more samples of the individual collected at two or more different times, the two or more samples including at least one of urine, saliva, and/or blood comprises:
   receiving two or more samples of the individual collected at two or more different times, the two or more samples including at least one of urine, saliva, blood, sweat, tears, breath, skin, hair, excrement, and/or mucus.

4. The method of claim 1, wherein the receiving two or more samples of the individual collected at two or more different times, the two or more samples including at least one of urine, saliva, and/or blood comprises:
   receiving two or more samples of the individual collected at two or more different times, the two or more samples including at least one hormone, prohormone, polynucleotide, enzyme, protein, vitamin, mineral, metal, and/or antioxidant.

5. The method of claim 1, wherein the assaying using one or more microfluidic chips the two or more samples to detect at least one amount of testosterone of each sample comprises:
assaying at different times and using one or more microfluidic chips the two or more samples to detect at least one amount of testosterone of each sample.

6. The method of claim 1, wherein the assaying using one or more microfluidic chips the two or more samples to detect at least one amount of testosterone of each sample comprises:
assaying using one or more detection units detachably associatable with one or more microfluidic chips the two or more samples to detect at least one amount of testosterone of each sample.

7. The method of claim 1, wherein one or more operations of the method are performed using one or more hand-held portable devices.

8. The method of claim 1, wherein one or more operations of the method are performed using two or more devices.

9. The method of claim 1, further comprising:
displaying at least one of the one or more dosages and/or one or more dosage modifications.

10. The method of claim 1, further comprising:
displaying at least one of the one or more dosages and/or one or more dosage modifications with one or more operably coupled display units.

11. The method of claim 1, further comprising:
displaying at least one of the one or more dosages and/or one or more dosage modifications in human-readable format.

12. The method of claim 1, further comprising:
displaying at least one of the one or more dosages and/or one or more dosage modifications in machine-readable format.

13. The method of claim 1, further comprising:
displaying one or more amounts and/or concentrations of testosterone.

14. The method of claim 1, further comprising:
transmitting one or more signals.

15. The method of claim 1, further comprising:
transmitting one or more signals to one or more display units.

16. The method of claim 1, further comprising:
transmitting one or more signals to one or more recording units.

17. The method of claim 1, further comprising:
transmitting one or more signals to one or more supplement suppliers.

18. The method of claim 1, further comprising:
receiving one or more signals.

19. The method of claim 1, further comprising:
providing for user interaction.

20. The method of claim 1, further comprising:
determining one or more predictions associated with testosterone.

21. A system comprising:
circuitry programmed to receive one or more parameters of an individual including at least one behavioral, characteristic, and/or appearance related parameter;
circuitry programmed to operate one or more devices for receiving two or more samples of the individual collected at two or more different times, the two or more samples including at least one of urine, saliva, and/or blood;
circuitry programmed to operate one or more microfluidic chips for assaying the two or more samples to detect at least one amount of testosterone of each sample;
circuitry programmed to determine one or more testosterone amount changes over time using the at least one amount of testosterone of each sample; and
circuitry programmed to identify, based upon one or more potential relationships of the one or more testosterone amount changes and the one or more parameters, one or more dosages and/or one or more dosage modifications of one or more non- pharmaceutically regulated nutraceutical agents for supplementation of the individual.

22. The system of claim 21, wherein the circuitry programmed to receive one or more parameters of an individual including at least one behavioral, characteristic, and/or appearance related parameter comprises:
circuitry programmed to receive via one or more user interfaces one or more parameters of an individual including at least one behavioral, characteristic, and/or appearance related parameter.

23. The system of claim 21, wherein the circuitry programmed to operate one or more devices for receiving two or more samples of the individual collected at two or more different times, the two or more samples including at least one of urine, saliva, and/or blood comprises:
circuitry programmed to operate one or more devices for receiving two or more samples of the individual collected at two or more different times, the two or more samples including at least one of urine, saliva, blood, sweat, tears, breath, skin, hair, excrement, and/or mucus.

24. The system of claim 21, wherein the circuitry programmed to operate one or more devices for receiving two or more samples of the individual collected at two or more different times, the two or more samples including at least one of urine, saliva, and/or blood comprises:
circuitry programmed to operate one or more devices for receiving two or more samples of the individual collected at two or more different times, the two or more samples including at least one hormone, prohormone, polynucleotide, enzyme, protein, vitamin, mineral, metal, and/or antioxidant.

25. The system of claim 21, wherein the circuitry programmed to operate one or more microfluidic chips for assaying the two or more samples to detect at least one amount of testosterone of each sample comprises:
circuitry programmed to operate one or more microfluidic chips for assaying at different times the two or more samples to detect at least one amount of testosterone of each sample.

26. The system of claim 21, wherein the circuitry programmed to operate one or more microfluidic chips for assaying the two or more samples to detect at least one amount of testosterone of each sample comprises:
circuitry programmed to operate one or more detection units detachably associatable with one or more microfluidic chips for assaying the two or more samples to detect at least one amount of testosterone of each sample.

27. The system of claim 21, wherein one or more circuitry of the system is included in one or more hand-held portable devices.

28. The system of claim 21, wherein one or more circuitry of the system is included in two or more devices.

29. The system of claim 21, further comprising:
circuitry programmed to operate one or more devices for displaying at least one of the one or more dosages and/or one or more dosage modifications.

30. The system of claim 21, further comprising:
circuitry programmed to operate one or more devices for displaying at least one of the one or more dosages and/or one or more dosage modifications with one or more operably coupled display units.

31. The system of claim 21, further comprising:
circuitry programmed to operate one or more devices for displaying at least one of the one or more dosages and/or one or more dosage modifications in human-readable format.

32. The system of claim 21, further comprising:
circuitry programmed to operate one or more devices for displaying at least one of the one or more dosages and/or one or more dosage modifications in machine-readable format.

33. The system of claim 21, further comprising:
circuitry programmed to operate one or more devices for displaying one or more amounts and/or concentrations of testosterone.

34. The system of claim 21, further comprising:
circuitry programmed to operate one or more devices for transmitting one or more signals.

35. The system of claim 21, further comprising:
circuitry programmed to operate one or more devices for transmitting one or more signals to one or more display units.

36. The system of claim 21, further comprising:
circuitry programmed to operate one or more devices for transmitting one or more signals to one or more recording units.

37. The system of claim 21, further comprising:
circuitry programmed to operate one or more devices for transmitting one or more signals to one or more supplement suppliers.

38. The system of claim 21, further comprising:
circuitry programmed to receive one or more signals.

39. The system of claim 21, further comprising:
circuitry programmed to operate one or more devices for providing for user interaction.

40. The system of claim 21, further comprising:
circuitry programmed to determine one or more predictions associated with testosterone.

41. Non-transitory computer readable media embodying device detectable instructions for facilitating operations comprising:
receiving one or more parameters of an individual including at least one behavioral, characteristic, and/or appearance related parameter;
receiving two or more samples of the individual collected at two or more different times, the two or more samples including at least one of urine, saliva, and/or blood;
assaying using one or more microfluidic chips the two or more samples to detect at least one amount of testosterone of each sample;
determining one or more testosterone amount changes over time using the at least one amount of testosterone of each sample; and
identifying, based upon one or more potential relationships of the one or more testosterone amount changes and the one or more parameters, one or more dosages and/or one or more dosage modifications of one or more non-pharmaceutically regulated nutraceutical agents for supplementation of the individual.

42. The device detectable instructions for facilitating operations of claim 41, wherein the receiving one or more parameters of an individual including at least one behavioral, characteristic, and/or appearance related parameter comprises:
receiving via one or more user interfaces one or more parameters of an individual including at least one behavioral, characteristic, and/or appearance related parameter.

43. The device detectable instructions for facilitating operations of claim 41, wherein the receiving two or more samples of the individual collected at two or more different times, the two or more samples including at least one of urine, saliva, and/or blood comprises:
receiving two or more samples of the individual collected at two or more different times, the two or more samples including at least one of urine, saliva, blood, sweat, tears, breath, skin, hair, excrement, and/or mucus.

44. The device detectable instructions for facilitating operations of claim 41, wherein the receiving two or more samples of the individual collected at two or more different times, the two or more samples including at least one of urine, saliva, and/or blood comprises:
receiving two or more samples of the individual collected at two or more different times, the two or more samples including at least one hormone, prohormone, polynucleotide, enzyme, protein, vitamin, mineral, metal, and/or antioxidant.

45. The device detectable instructions for facilitating operations of claim 41, wherein the assaying using one or more microfluidic chips the two or more samples to detect at least one amount of testosterone of each sample comprises:
assaying at different times and using one or more microfluidic chips the two or more samples to detect at least one amount of testosterone of each sample.

46. The device detectable instructions for facilitating operations of claim 41, wherein the assaying using one or more microfluidic chips the two or more samples to detect at least one amount of testosterone of each sample comprises:
assaying using one or more detection units detachably associatable with one or more microfluidic chips the two or more samples to detect at least one amount of testosterone of each sample.

47. The device detectable instructions for facilitating operations of claim 41, wherein one or more operations are performed using one or more hand-held portable devices.

48. The device detectable instructions for facilitating operations of claim 41, wherein one or more operations are performed using two or more devices.

49. The device detectable instructions for facilitating operations of claim 41, further comprising:
displaying at least one of the one or more dosages and/or one or more dosage modifications.

50. The device detectable instructions for facilitating operations of claim 41, further comprising:
displaying at least one of the one or more dosages and/or one or more dosage modifications with one or more operably coupled display units.

51. The device detectable instructions for facilitating operations of claim 41, further comprising:
displaying at least one of the one or more dosages and/or one or more dosage modifications in human-readable format.

52. The device detectable instructions for facilitating operations of claim 41, further comprising:
displaying at least one of the one or more dosages and/or one or more dosage modifications in machine-readable format.

53. The device detectable instructions for facilitating operations of claim 41, further comprising:
  displaying one or more amounts and/or concentrations of testosterone.

54. The device detectable instructions for facilitating operations of claim 41, further comprising:
  transmitting one or more signals.

55. The device detectable instructions for facilitating operations of claim 41, further comprising:
  transmitting one or more signals to one or more display units.

56. The device detectable instructions for facilitating operations of claim 41, further comprising:
  transmitting one or more signals to one or more recording units.

57. The device detectable instructions for facilitating operations of claim 41, further comprising:
  transmitting one or more signals to one or more supplement suppliers.

58. The device detectable instructions for facilitating operations of claim 41, further comprising:
  receiving one or more signals.

59. The device detectable instructions for facilitating operations of claim 41, further comprising:
  providing for user interaction.

60. The device detectable instructions for facilitating operations of claim 41, further comprising:
  determining one or more predictions associated with testosterone.

* * * * *